(12) United States Patent
Flock et al.

(10) Patent No.: US 7,967,839 B2
(45) Date of Patent: Jun. 28, 2011

(54) ELECTROMAGNETIC TREATMENT OF TISSUES AND CELLS

(75) Inventors: Stephen T. Flock, Arvada, CO (US); Kevin S. Marchitto, Golden, CO (US)

(73) Assignee: Rocky Mountain Biosystems, Inc., Golden, CO (US)

( * ) Notice: Subject to any disclaimer, the term of this patent is extended or adjusted under 35 U.S.C. 154(b) by 652 days.

(21) Appl. No.: 10/815,084

(22) Filed: Mar. 31, 2004

(65) Prior Publication Data

US 2004/0210282 A1    Oct. 21, 2004

Related U.S. Application Data

(63) Continuation-in-part of application No. 10/736,113, filed on Dec. 15, 2003, now Pat. No. 7,446,803, which is a continuation-in-part of application No. 10/441,341, filed on May 20, 2003.

(60) Provisional application No. 60/381,948, filed on May 20, 2002.

(51) Int. Cl.
*A61B 17/02* (2006.01)

(52) U.S. Cl. ........ 606/213; 606/214; 606/218; 606/220; 128/898

(58) Field of Classification Search ............... 607/96, 607/98–103; 606/32, 34, 41; 600/2, 8; 128/898
See application file for complete search history.

(56) References Cited

U.S. PATENT DOCUMENTS

| | | | | | |
|---|---|---|---|---|---|
| 4,889,120 | A | * | 12/1989 | Gordon | 606/216 |
| 5,057,106 | A | * | 10/1991 | Kasevich et al. | 606/33 |
| 5,366,443 | A | * | 11/1994 | Eggers et al. | 604/114 |
| 5,429,583 | A | * | 7/1995 | Paulus et al. | 600/2 |
| 5,824,015 | A | * | 10/1998 | Sawyer | 606/214 |
| 5,897,495 | A | * | 4/1999 | Aida et al. | 600/411 |
| 6,148,236 | A | * | 11/2000 | Dann | 607/101 |
| 6,171,321 | B1 | * | 1/2001 | Gifford et al. | 606/153 |
| 6,350,274 | B1 | * | 2/2002 | Li | 606/213 |
| 6,451,044 | B1 | * | 9/2002 | Naghavi et al. | 607/96 |
| 6,458,109 | B1 | * | 10/2002 | Henley et al. | 604/304 |
| 6,656,174 | B1 | * | 12/2003 | Hegde et al. | 606/41 |
| 6,814,712 | B1 | * | 11/2004 | Edwards et al. | 604/22 |

* cited by examiner

*Primary Examiner* — Henry M Johnson, III
*Assistant Examiner* — Aaron Roane
(74) *Attorney, Agent, or Firm* — Benjamin Aaron Adler

(57) ABSTRACT

Provided herein are methods, devices and compositions to conductively or to inductively fix substrates, including tissues, using electromagnetic energy. Also provided is a method of controlling the fixing process via feedback monitoring of a property of the composition and/or of the electromagnetic energy used.

17 Claims, 46 Drawing Sheets

ELECTROMAGNETIC TREATMENT OF TISSUES AND CELLS

CROSS-REFERENCE TO RELATED APPLICATIONS

This application is a continuation-in-part of U.S. Ser. No. 10/736,133, filed Dec. 15, 2003, now U.S. Pat. No. 7,446,803 which is a continuation-in-part of non-provisional U.S. Ser. No. 10/441,341, filed May 20, 2003, which claims benefit of provisional U.S. Ser. No. 60/381,948, filed May 20, 2002, now abandoned.

BACKGROUND OF THE INVENTION

1. Field of the Invention

The present invention relates generally to the fields of biomedical engineering, biochemistry and medical treatment and surgical procedures. More specifically, the present invention provides methods, devices and compositions for inducing changes in biomolecules and bioactive molecules useful for accelerating or enabling certain reactions, fixing or fusing tissues and implants, dressing, sealing or closing a wound to reduce the loss of internal fluids, for enhancing wound healing and for delivery of active agents to tissues.

2. Description of the Related Art

Effective closure of surgical wounds, including incisions, tears and leaks in the patient's organs is critical to the success of the surgical procedure. This success is based on restoration of the physical integrity and function of injured or diseased tissue. Failure to close surgical wounds optimally can also result in serious and excessive scarring. A variety of devices have been developed to assist the surgeon with surgical closure of tissue, including sutures, staples and fibrin glues.

Historically, wound dressings consist of some type of bandage or adhesive. More recently, wound sealing methods whereby energy is directed to the tissue have been tested and occasionally are used clinically. Traditional techniques of managing the wound include cleansing and debriding, treating with antibiotics and applying a dressing. Modern wound care products often seek to provide moisture, pH balance and nutrition in an effort to improve the potential for healing. The healing process may also complicate the status of the patient through formation of scar tissue. This scarring helps to close the wound, but its formation is accompanied by contraction and buildup of tissue which can lead to a loss in flexibility at the wound site and, in severe cases, may result in loss of mobility to the patient.

Conventional methods of wound closure following surgery consist of applying sutures or staples to join two or more tissues that have been dissected. While these methods are generally successful, at times complications arise due to inadequate closure of the wound that could result in the tissues separating or in "leakiness." In particular, the quality of suturing depends on manual dexterity of the surgeon and adequate access to the wound. Current designs of surgical clips can slip if applied incorrectly or accidentally disturbed. Surgical clips can also cause damage to the vessels or structures to which they are applied if the surgeon applies excessive compression force. With the increasing use of minimally invasive surgical methods, such as endoscopy, wound access and the efficient closure of wounds has become a significant issue in medicine.

A surgeon's skill is less of a factor where surgical staples are employed and, as a result, less invasive devices have been developed for effective delivery of staples through endoscopic trocars. This has led to greater acceptance for stapling devices over suturing during less invasive surgical procedures. Nonetheless, conventional stapling is limited in that it usually requires an anvil be placed behind the tissues to be joined, and that enough space is available to produce the necessary force to form the staple against the anvil.

Various methods have been employed to fasten tissues together without the use of a conventional staple or suture. These devices often employ springs or another compression mechanism to pull the tissues together. Shape memory alloys have been employed in U.S. Pat. Nos. 4,485,816, 5,002,562 and 6,113,611 and, in at least one case, using electronic heating of the fastener to make it close. U.S. Pat. No. 5,725,522 discloses the employment of lasers to effect suture "fusion" whereby two ends of the suture are fused together in place of the traditional knot.

A trend toward the use of minimally invasive surgical techniques has created a demand for wound closure methodology that can be used through a small incision in the patient. Sutures cannot easily be secured by traditional methods through an endoscope and current stapling methods generally require an anvil be placed behind the tissue thereby limiting their use. U.S. Pat. No. 6,358,271 describes the use of sutures composed of a fused loop of filamentous material which is ultrasonically welded. This application has the advantage of a low profile of suture closure as compared to the traditional knot and may ultimately be applied endoscopically, however the technology still requires the use of a fairly large securing device including an anvil. U.S. Pat. Nos. 6,409,743 and 6,423,088 discuss c-shaped collars that are made out of a material that fuses to itself upon the application of energy in the form of heat, light, radiofrequency waves, electricity or ultrasound.

More recently, wound sealing approaches, which employ methods of directing energy to the tissue which as a consequence adheres to proximal tissue, have been tested and used clinically. Commercial electrosurgery and electrocautery devices commonly are used for sealing internal wounds, such as those arising through surgical intervention. Inventions for sealing vessels using other forms of electromagnetic energy have been published. U.S. Pat. No. 6,033,401 describes a device to deliver adhesive and apply microwave energy to effect sealing of a vessel. U.S. Pat. No. 6,179,834 discloses a vascular sealing device to provide a clamping force, while radiofrequency energy is applied, until a particular temperature or impedance is reached. U.S. Pat. No. 6,132,429 describes using a radiofrequency device to weld blood vessels closed and monitoring the process by changes in tissue temperature or impedance. Nevertheless, these devices are generally unsuitable for the purpose of occluding a wound thereby enhancing long-term healing.

Over the past fifteen years, a significant amount of scientific research has focused on using laser heated "solder" for "welding" tissues such as blood vessels (1-2). Research has been done on laser tissue welding with albumin solders which are an improvement over conventional suture closure because it offers an immediate watertight tissue closure, decreased operative time, especially in microsurgical or laparoscopic applications, reduced trauma, and elimination of foreign body reaction to sutures, collagen-based plugs and clips. The procedure has been enhanced with the use of advanced solders, strengthening structures, concurrent cooling, and added growth factors as disclosed, for example, in U.S. Pat. No. 6,221,068.

Use of lasers for tissue welding appeared very promising, however, over the years the techniques have been shown to present certain limitations. The laser energy must be manually directed by the surgeon which leads to operator variability. Additionally, the radiant energy is not dispersed evenly throughout the tissue. The high energy at the focal point may result in local burns and the heating effect drops off rapidly at a small distance from the focal point. Finally, lasers are expensive and currently cannot be miniaturized easily.

A number of patents describe using electromagnetic energy, often in the form of laser or other radiant energy, to heat tissue or a biocompatible "solder" to effect tissue sealing or fusion. U.S. Patent Publication Nos. 2003/019862 and 2003/0195499, for example, describe microwave antennae suitable for cutting or ablating tissue. U.S. Pat. No. 5,925,078 describes using a form of energy, such as microwaves or radiofrequency, to fuse endogenous collagen fibrils in tissue, whereupon the strength of the fusion is enhanced by subsequent chemically-induced protein cross-linking. U.S. Pat. No. 6,669,694 uses a different application of energy, in the form of a vaporized biocompatible material, which exits an applicator to impinge on tissue in order to effect a beneficial tissue effect. Neither Anderson nor Shadduck describe using an additional adhesive during the described processes.

Menovsky and co-workers (Effect of $CO_2$-milliwatt laser on peripheral nerves: Part II. A histological and functional study, Microsurgery 20, pp 150-155, 2000) showed that by using an albumin solder applied to a sciatic nerve and cured with the radiant energy produced by a CO2 laser, it was possible to elicit nerve repair without causing unacceptable thermal side-effects. Lauto et al. (Laser-activated solid protein bands for peripheral nerve repair: an vivo study. Lasers in Surgery & Medicine. 21, pp 134-41, 1997) and McNally-Heintzelman et al. (Scaffold-enhanced albumin and n-butyl-cyanoacrylate adhesives for tissue repair: ex vivo evaluation in a porcine model. Biomedical Sciences Instrumentation. 39, pp 312-7, 2003) found beneficial results of laser-nerve welding using other laser radiant energy and differing adhesive compositions. Nevertheless, the lack of control and the inability to induce uniform heating in the nerve as a result of laser irradiation restricts the utility of laser-nerve welding to the laboratory. Becasue of this, the procedure is not used in the clinic on human patients.

There has been an effort recently to identify biocompatible molecules which can be used as a "tissue solder". Biomolecules such as fibrin, elastin, and albumin have been or are used to "glue" tissue to tissue. A number of patents describe the "activation" of these biomolecules to form "welds" through irradiation, often in the form of laser radiant energy, but sometimes in the form of ultrasound or radiofrequency waves. The applied energy is believed to denature the molecules, which then adhere to one another or cross-link to one-another and to protein in tissues, thereby effecting a union between the tissues.

Over the past fifteen years, a significant amount of scientific research has focused on using laser heated "solder" for "welding" tissues such as blood vessels (1-2). Research has been done on laser tissue welding with albumin solders which is an improvement over conventional suture closure because it offers an immediate watertight tissue closure, decreased operative time, especially in microsurgical or laparoscopic applications, reduced trauma, and elimination of foreign body reaction to sutures, collagen-based plugs and clips. The procedure has been enhanced with the use of advanced solders, strengthening structures, concurrent cooling, and added growth factors, e.g., as disclosed in U.S. Pat. Ser. No. 6,221,068.

Use of lasers for tissue welding appeared very promising, however, the techniques have certain limitations. The laser energy must be manually directed by the surgeon, which leads to operator variability. Additionally, the radiant energy is not dispersed evenly through the tissue. The high energy at the focal point may result in local burns and the heating effect drops off rapidly at a small distance from the focal point. Finally, lasers are expensive and currently cannot be easily miniaturized.

U.S. Pat. No. 5,669,934 describes a method for joining or restructuring tissue consisting of providing a preformed film or sheet of a collagen and/or gelatin material which fuses to tissue upon the application of continuous inert gas beam radiofrequency energy. Similarly, U.S. Pat. No. 5,569,239 describes laying down a layer of energy reactive adhesive material along the incision and closing the incision by applying energy, either optical or radiofrequency energy, to the adhesive and surrounding tissue. Furthermore, U.S. Pat. Nos. 5,209,776 and 5,292,362 describe a tissue adhesive that is principally intended to be used in conjunction with laser radiant energy to weld severed tissues and/or prosthetic material together.

U.S. Pat. No. 6,110,212 describes the use of elastin and elastin-based materials which are biocompatible and can be used to effect anastomoses and tissue structure sealing upon the application of laser radiant energy. The stated benefits, inter alia, are the biocompatible and ubiquitous nature of elastin. U.S. patent application Ser. No. 20020198517 discloses the use of laser tissue-welding employing an adhesive consisting mostly of gelatin which effects tissue attachment.

Furthermore, U.S. Pat. No. 6,302,898 describes a device to deliver a sealant and energy to effect tissue closure. The tissue is pre-treated with energy in order to make the subsequently applied sealant adhere better. In International Publication WO 99/65536 pre-treatment of a substantially solid biomolecular solder prior to tissue repair use is taught.

U.S. Pat. No. 5,713,891 describes the addition of bioactive compounds to the tissue solder in order to enhance the weld strength or to reduce post-procedure hemorrhage. U.S. Pat. No. 6,221,068 discloses the importance of minimizing thermal damage to the tissue to be welded. By using pulsed laser radiation and allowing the tissue to cool to nearly the initial temperature between each heating cycle, the damage is minimized.

U.S. Pat. No. 6,323,037 describes the addition of an "energy converter" to the solder mixture such that incident optical energy will be efficiently and preferentially absorbed by the solder which subsequently effects a tissue weld. Similarly U.S. Pat. No. 6,348,679 describes using a radiofrequency "susceptor", i.e., a compound that absorbs RF energy and converts it to heat.

U.S. Pat. No. 5,749,895 describes using a tissue adhesive which is heated in proximity to a mechanical support with radiofrequency heated inert gas. U.S. Pat. No. 6,547,794 describes using a bony material implant, to which a tissue adhesive is applied, inserted between the surfaces of bones to be fused, and to which energy is applied to achieve the weld. U.S. Pat. No. 5,749,895 and U.S. Pat. publication No. 2003/019866 disclose a device and method for sealing tissue punctures with a fluent closure composition precursor heated with the energy emitted from a microwave antenna. None of these aforementioned inventions describe the use of a material within the adhesive which serves to enhance the absorption of the incident energy relative to the surrounding tissue. Materials to enhance the absorption of optical radiation during tissue welding have been described in numerous patents and patent applications, e.g. U.S. Patent Publication 2002/0198517; these inventions generally focus on optical means of tissue sealing and welding. The prior art fails to describe adequate means for delivering compositions that may be activated using radiofrequency energy sources.

Common problems exist throughout the prior art. These include, for example, tissue damage due to uneven heating, unknown and/or uncontrollable thermal history, i.e., time-temperature profile, and relatively high cost. It is notable that a consistent means of treatment and control are desirable. The Code of Federal Regulations, 21 CFR 860.7(e)(1), establishes that there is "reasonable assurance that a device is effective when it can be determined, based upon valid scientific evidence, that in a significant portion of the target population, the use of the device will provide clinically significant results." Devices that cannot be shown to provide consistent results between patients, or even within a patient upon multiple use, will have minimal utility and may not be approvable for broad use. Beyond devices, it is generally desirable to develop medical products with critical controls that can deliver precise results.

Inductive heating (3) is a non-contact process whereby electrical currents are induced in electrically conductive materials (susceptors) by a time-varying magnetic field. Generally, induction heating is an industrial process often used to weld, harden or braze metal-containing parts in manufacturing where control over the heating process and minimized contact with the workpiece are critical. Basically, radiofrequency power is coupled to a conducting element, such as a coil of wire, which serves to set up a magnetic field of a particular magnitude and spatial extent. As a result, induced currents or Eddy currents flow in the conductive materials in a layer referred to as the skin depth $\delta$, given by:

$$\delta = \sqrt{(2\rho/\mu\omega)}$$

where $\omega$ is frequency (rads/s), $\rho$ is resistivity (ohm-m) and $\mu$ is the permeability (Webers/amp/m) which is the product of $\mu_o$ the permeability of free space and $\mu_r$ the relative permeability of the material.

The magnetic permeability of a material is quantification of the degree to which it can concentrate magnetic field lines. Note, however, that the permeability is not constant in ferromagnetic substances like iron, but depends on the magnetic flux and temperature. The skin depth at room temperature at 1 MHz electromagnetic radiation in copper is 0.066 mm and in 99.9% iron is 0.016 mm.

The consequence of current flowing is Joule heating. The skin-depth formula leads to the conclusion that, with increased frequency, the skin depth becomes smaller. Thus, higher frequencies favor efficient and uniform heating of smaller components.

In certain situations, localized heat can also be generated through hysteresis losses or frictional heating as the susceptor moves against physical resistance in the surrounding material. Consideration of Joule heating alone results in a formula for the power-density $P(W/cm^3)$ in the inductively-heated material:

$$P = 4\pi H^2 \mu_o \mu_r f M$$

where H is the root means square (RMS) magnetic field intensity (A/m), f is frequency (Hz), M is a power density transmission factor (unitless) which depends on the physical shape of the heated material and skin depth and diameter of the part to be heated (4-5).

M, which is equal to the product of F and $d/\delta$, where F is a transmission factor and d is the diameter of the part, can be shown to be maximally about 0.2 when the object diameter is 3.5 times the skin depth, and when certain other assumptions are made. Thus, for a given frequency, there is a diameter for which the power density is a maximum or, equivalently, there is a maximum frequency for heating a part of a certain diameter below which heating efficiency drops dramatically and above which little or no improvement of heating efficiency occurs. It also can be shown that the power density of inductively heated spheres is much higher than solid spheres of the same material.

There are only a few examples of the use of inductive heating in the medical literature. The oldest example of use of therapeutic inductive heating is in hyperthermia of cancer, whereby large metallic "seeds" are inductively heated using a coil external to the body (6). Smaller seeds were used where small biocompatible dextran magnetite particles in magnetic fluid was used to treat mouse mammary carcinoma by hyperthermia (7). U.S. patent application Ser. No. 2002/0183829 describes inductively heating stents made of alloys with a high magnetic permeability and low curie temperature for the purpose of destroying smooth muscle cells in restenosing blood vessels. A more recent report described the diagnostic use of induction heating to heat nanocrystals coupled to DNA in order to locally denature DNA for the purpose of hybridization (8).

The literature is deficient in descriptions whereby biomolecules are heated through induction. U.S. Pat. No. 6,348,679 discloses compositions used in bonding two or more conventional materials where the interposed composition consists of a carrier and a susceptor, which may be at least in part composed of certain proteins. However the applications apply to conventional substrates such as films or wood. The effects of induction in tissue are not limited to tissue fusion. U.S. Pat. No. 6,573,491 and International Publications WO 00/69515 and WO 00/77045 describe specific formulations, methods and devices where electromagnetic energy absorption is maximized relative to the surrounding medium, resulting in effects such as accelerated reaction rates and molecular mobility. One method of accomplishing this energy absorption is through inductive heating.

Many surgeries would benefit from the use of sutureless wound closure methods and improved methods of sealing tissues. Surgery of the colon or rectum is often performed in patients with colorectal cancer and inflammatory bowel disease. The surgery involves removal of the diseased tissue and an anastomosis of the juxtaposed ends. In 2000, approximately 162,000 intestinal anastomoses were performed in the U.S. While advances in surgical techniques have improved outcomes, one of the most severe and life-threatening complications is anastomotic leakage, which occurs in 0-20% of cases, with a mortality rate ranging between 6 and 22%. The cost of colorectal cancer in the U.S. was estimated at $5.4 B in 2000. Small anastomotic leaks can be treated with percutaneous drainage, antibiotics, bowel rest and total parenteral nutrition to promote spontaneous closure. A large, free leak requires prompt laparotomy with stoma creation. Treatment protocols for these complications increase morbidity, mortality, hospital time and expense. Clearly a way to improve colonic anastomoses could have a profound positive effect on patient care and the health-care financial burden.

Tens of millions of venous access and puncture wounds are created each year as a result of catheterization procedures, biopsies, hemodialysis treatments and other procedures. Manual compression has been the standard of care for closure after percutaneous coronary interventions, but it requires prolonged bed rest, e.g. 4-12 hours, leading to delayed ambulation, significant medical staff time and associated higher costs. The routine administration of anticoagulant medication to prevent blood clots and stroke during the diagnostic or interventional procedure can further delay sealing the vessel and postpone ambulation. Complication rates as high as 12.5% for extraction atherectomy, and 11% for balloon angioplasty have been reported.

In recent years, several closure devices have been introduced to the market. Suture-mediated closure (SMC) devices push a shaft into the artery and use stitches to suture and close the puncture. When compared to manual compression, the advantages of SMCs are a quicker time to hemostasis, 5 minutes vs. 25 minutes, and ambulation, 1 hour vs. 4-6 hours. However, these devices generally require a trained physician to insert the sutures, while most other closure devices can be managed by non-physicians. Reported complications include an increase in the number of access site infections, as well as pain and discomfort for the patient.

Some collagen-based closure devices use a biodegradable bovine collagen plug to form a coagulum at the access site. The two primary types are a plug, e.g. VasoSeal™ and a collagen plug with an anchor, such as Angio-Seal™. Hemostasis success rates range from 88%-100%, with an average success of 97%. When compared to manual compression, most studies show results similar to those for SMCs, i.e., a decrease in time to ambulation, 1 hour vs. 4-6 hours and time to hemostasis, 5 minutes vs. 25 minutes, and, furthermore, a 1 day reduction in hospital stay. Data on complications is mixed, with several studies showing minor complications comparable to compression, but an increase in major complications that require surgical repair. Other studies show an increase in minor complications. Collagen-based devices seal the vessel, but fail to seal the tract. In addition, manufacturers recommend that healthcare professionals not use the sealed vessel for a period of 3-6 weeks while the collagen plug is absorbed.

Manual pressure is the current standard of care for stopping post-dialysis bleeding as well. Limitations to manual pressure include: (1) the 10 to 20 minutes it typically takes to stop bleeding, occasionally taking up to an hour for difficult cases; (2) patients routinely receiving anticoagulant agents during their treatment thus lengthening the time required to stop the bleeding and leave the clinic; (3) applying too little pressure doesn't stop the bleeding, resulting in excess blood loss; (4) applying too much pressure causing the access to thrombose which requires additional interventions; and (5) manual pressure is labor intensive for the dialysis staff when patients are unable to hold their own site following needle removal. Success in rapidly and completely stopping the bleeding and sealing the tissue following the treatment can reduce complications such as infection and post-dialysis bleeding, as well as preserving the access.

Of the hundreds of thousands of Americans living with end stage renal disease, more than half undergo hemodialysis treatments 2-3 times each week. One challenge associated with successful hemodialysis is vascular access, the method used to access a patient's blood supply. Complications related to vascular access include thrombosis, stenosis, infection, pseudoanuerysm, limb ischemia and post-dialysis bleeding. The complications lead to loss of vascular access and the need for corrective surgery in the vast majority of patients twice per year. These corrective surgeries normally involve replacing an arteriovenous fistula or synthetic graft which provides access to the patient's blood supply.

The inventors recognize a need in the art for a precision device and improved methods of joining tissues which have been separated through surgery or through trauma, particularly during minimally invasive procedures. The prior art is particularly deficient in devices and methods for minimally-invasive methods that use electromagnetic energy to controllably alter a biocompatible structure thereby making it adhere to tissue through molecular alterations and/or mechanical shrinkage. The present invention fulfills this longstanding need and desire in the art.

SUMMARY OF THE INVENTION

The present invention is directed to a method of treatment for one or more substrates in an individual. A means of securing the substrate(s) is positioned proximally thereto where the securing means is a susceptor or comprises a susceptor. Energy is applied to the substrate(s) or to the susceptor or to a combination thereof to generate heat therein. The substrate(s) are fixed via the heat which effects treatment. Furthermore, the fixing process may be controlled by feedback monitoring of a property of the susceptor(s) and/or the energy.

The present invention also is directed to a fusion composition to secure a substrate. The fusion composition comprises a susceptor and an adherend. The fusion composition may comprise a surgical fastener, a laminate or a surgical fitting.

The present invention is directed further to a device for fixing tissues. The device comprises a means to provide energy, the fusion composition described herein, an applicator comprising the fusion composition; a means of applying the energy to the fusion composition and a means to control a property of the fusion composition and/or the energy applied.

The present invention is directed further still to a method of monitoring electrical conductivity in a biological sample. An electromagnetic field is generated proximate to the sample to heat the sample and the eddy currents in the sample generated via the electromagnetic field are monitored. Eddy current density is correlated with electrical conductivity in the biological sample thereby monitoring it.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
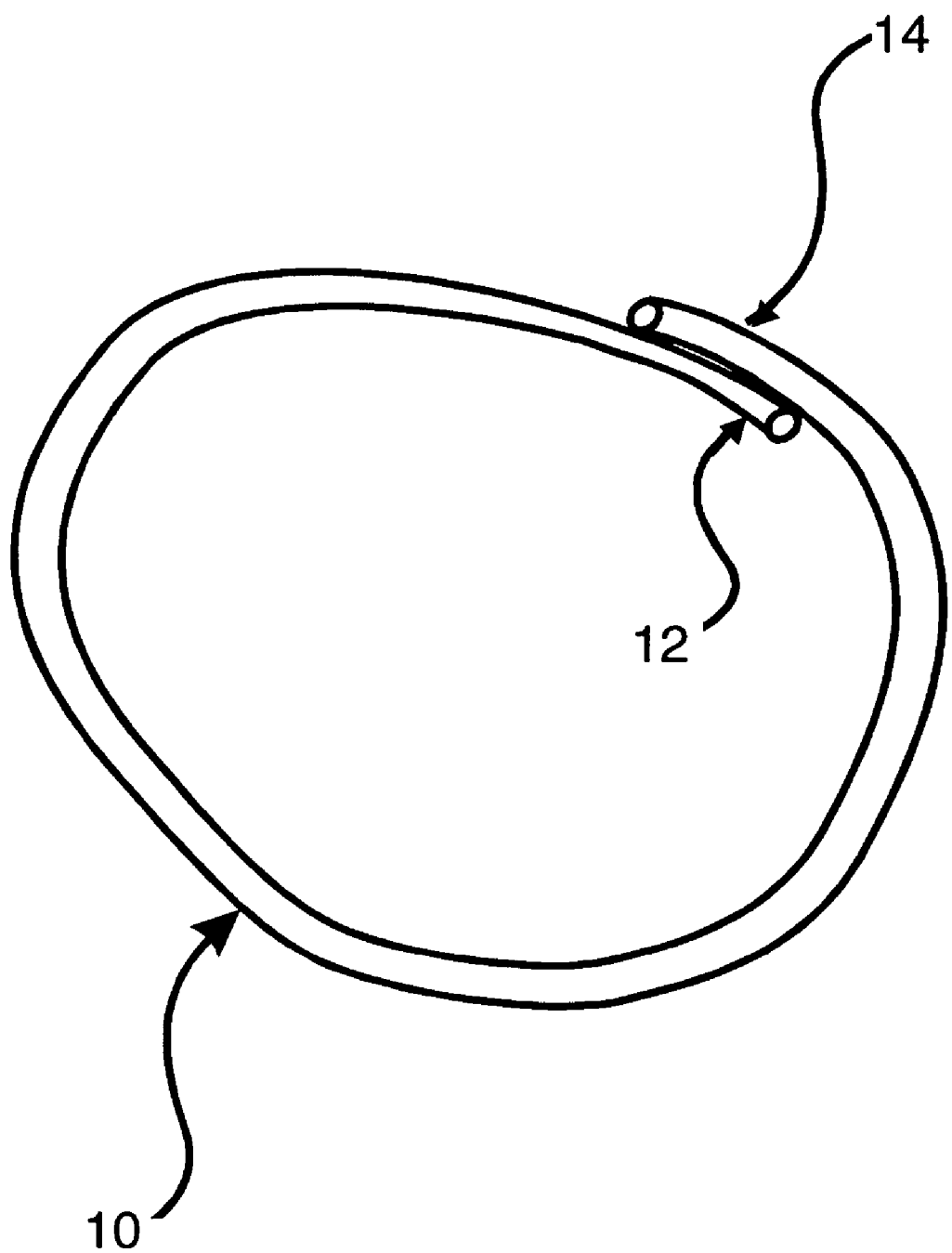
FIG. 1 depicts a closed loop surgical suture composed of filamentous material and a metal.

One embodiment of the present invention provides a method treatment for one or more substrates in an individual, comprising positioning a means of securing said substrate(s) proximally thereto wherein the securing means is a susceptor or comprises a susceptor; applying energy to the substrate(s) or to the susceptor or to a combination thereof to generate heat therein; and fixing said substrate(s) via said heat thereby effecting treatment.

In this embodiment the method further comprises controlling the fixing of the substrate(s) via feedback monitoring of a property of the susceptor, the energy or a combination thereof. Examples of such properties are heat, an electrical property, eddy currents, conductivity, or frequency changes or a combination thereof. Furthermore, heat may be monitored via optical detection. A representative example of optical detection is infrared.

In all aspects of this embodiment the substrates may be a tissue, an implant or a bandage. The susceptor may be a metal, a liposome encapsulating a metal, a dye, an ion or a mixture of ions or an ultrasound contrasting agent. Further the susceptor may comprise matter with non-zero electrical conductivity. The susceptor may be diamagnetic, paramagnetic or ferromagnetic.

Again in all aspects the securing means may be a fastener, a laminate or a fitting. Examples of a fastener are a staple, a clip or a suture. Additionally, the securing means may comprise an adherend. Examples of an adherend are a protein or a polymer.

In aspects of this embodiment the energy may be inductively or conductively applied. Additionally, the energy may be pulsed. Examples of applied energy are radiofrequency energy, radiant energy or vibrational energy. The radiofrequency energy may have a frequency from about 20 kHz to about 40 GHz.

In one aspect the energy may generate an electromagnetic field. Such electromagnetic field may be generated via an antenna. The antenna may comprise at least one coil of electrical conductor. Examples of an electrical conductor are a solid wire or hollow tubing. Representative examples of an antenna are a single coil antenna, a double coil antenna or a solenoid.

In this embodiment fixing the substrate(s) forms a scaffold or a lattice structure within the substrate or between substrates. Additionally, fixing the substrate(s) may seal a tissue, fill a tissue defect or bonds tissues together.

Another embodiment of the present invention provides a fusion composition to secure a substrate comprising a susceptor and an adherend. Further to this embodiment the fusion composition may comprise a heat-sensitive material. Representative examples of a heat-sensitive material are a dye, a ferromagnetic material or a liposome. In this embodiment the adherend may be a protein or a polymer. The substrates are as described supra. Further to this embodiment the fusion composition may comprise a fastener, a laminate or a fitting. Examples of a fastener are a staple, a clip or a suture.

Yet another embodiment of the present invention provides a device for fixing tissues comprising a means to provide energy; the fusion composition described supra; an applicator comprising the fusion composition; a means of applying the energy to the fusion composition; and a means to control a property of the fusion composition or said energy or a combination thereof.

In all aspects of this embodiment the energy is as described supra. The means of applying energy may be inductive or conductive. The means of inductively applying energy may comprise an antenna as described supra. The means of conductively applying energy may comprise an electrode, an electrode pair or an electrode array. The means of controlling a property of the fusion compound and/or the energy are as described supra. Additionally, the means of controlling a property of the fusion compound may be self-limiting. Examples of self-limiting control means are a heat-sensitive dye a liposome or a ferromagnetic material.

Still another embodiment of the present invention provides a method of monitoring electrical conductivity in a biological sample, comprising inductively generating an electromagnetic field proximally to the sample to heat the sample; monitoring eddy currents in the sample generated via the electromagnetic field; and correlating eddy current density with electrical conductivity in the biological sample thereby monitoring said electrical conductivity.

In all aspects of this embodiment the biological sample may be in vivo or in vitro. The biological sample may be a tissue, a fusion composition or a combination thereof. Additionally, the biological sample may comprise a diagnostic assay.

As used herein, the term "weld" or, "fusion", may be used interchangeably to represent bonding or attachment of one or more materials including sections of tissue to another section of tissue, to a fusion composition, to a dressing, or to a fastening device such as a clip, pin or staple.

As used herein, the term "curing" may be used to describe a process whereby applying energy to a substrate or substance changes the rheologic nature of the substrate or substance.

Provided herein are methods, compositions and devices for bonding or fusing, curing, molding, sealing and/or fixing and separating at least two materials where at least one material is a tissue. The device comprises an adherend, which can be a biocompatible material, a means of applying radiofrequency energy or electrical energy to generate heat within the adherend, and a means of controlling output of the heat generated within the adherend conducted to the materials to be bonded or fused. The device may be of a particular form such that it can be beneficially used in particular surgical procedures, such as colonic anastomoses.

Devices are described for general use in anastomosis, not limited to tubular structures, as well as sealing, and filling of tissue defects using a fusion composition comprising an adherend, which can be a biocompatible material and a means of applying radiofrequency energy or electrical energy to generate heat within the adherend. The adherend material can beneficially act as a mechanical support for tissue or can easily be applied to a variety of tissue geometries. Adherence of the biocompatible material to the tissues or adherence of the tissues results from molecular changes in the biocompatible material and said tissues.

Furthermore, the present invention generally provides devices, methods and compositions for heating or inducing conformational changes in substrates placed in or found in organisms and cells. The substrates themselves may consist of biomolecules or bioactive molecules, tissues or individual cells, compositions applied to induce a certain effect and certain components of those compositions. Alternatively, the substrates may be molecules and structures that change conformation upon exposure to electromagnetic energy. The substrates may exist in a reaction vessel, in an organism or in tissue or cells present in or derived from an organism. The composition generally is a fusion composition substantially comprising a biomolecule or bioactive molecule, but additionally may comprise a non-biological material.

The conformational change(s) in these substrates, compositions, biomolecules and/or bioactive molecules is such that they may react in a unique manner or such that the rate of reaction is accelerated. The enhanced reactions are useful in a range of biological applications, including, but not limited to, wound healing and tissue fusion, deposition of pharmaceutical agents, fixation of implants and tissues, development of multi-laminate and multi-vessicular delivery agents, and cosmetic alteration of tissues.

Generally, biomolecules, including otherwise bioactive molecules, which are naturally occurring in a living organism or those which can have an influence on molecules in a living organism may be used in the formulations and compositions described herein. Typically, such molecules may be found in or around cells and tissues or may be supplied to living organisms, cells and tissues to achieve a desired effect or response.

Examples of biomolecules include proteins, carbohydrates or lipids found in cells or tissues. The biomolecules may be, although not limited to, structural, such as tissue structures composed of elastin or collagen or structural cellular components such as actin, myosin, or ribonucleoprotein particles. The biomolecules may be involved in catalysis, e.g. enzymes, or may be reactants, e.g., protease susceptible proteins or metabolized lipids. Examples of other bioactive molecules include, but are not limited to, biological response modifiers, antigens, protease inhibitors, other enzymes, and metabolic inhibitors.

The device may comprise a source of radiofrequency (RF) energy coupled to an applicator that then produces an oscillating magnetic field, and the substrates, with or without the compositions, which inductively couple with the magnetic field resulting in the transient production of heat and/or kinetic energy substantially within the substrate and/or the composition which may be liquid, solid or semi-solid. The device comprises these components: activator, applicator, and, optionally, surgical fasteners and/or a fusion composition. The surgical fasteners may comprise completely or partially the fusion composition. Furthermore, the device may be incorporated within a patch.

The heating process may be used to heat substrates such as, but not limited to, tissue components or cells, molecular entities, e.g., proteins, lipids, carbohydrates, organic molecules such as pharmaceuticals, and non-tissue components or inorganic materials, e.g. electro- and magnetically sensitive materials such as shape memory alloys such that they may be altered in structure, adhere to one another, or where it is desirous that they be separated from one another. The heating process also may heat a liquid, solid or semi-solid fusion composition which may comprise the substrate or may be other than the substrate. The consequence of heat or other increased energy is molecular changes in the composition resulting in, for example, fusion with the adjacent tissue or changes in molecular conformations. The adjacent tissue may take part in the fusion process by also being altered by the transient presence of heat.

Applications include bonding or fusing, coagulating, molding, fixing, sealing and separating tissue components. For example applications may be fixing or curing a biological or bioactive material in place or may be fixing or curing substrates to adhere to structures. Additionally, applications may be used for bonding tissues or for filling defects in tissues, collectively referred to as fixing tissues.

Sealing or welding a wound also is contemplated. A material or fusion composition that promotes the formation of a strong weld may be placed between layers of tissue, or between a tissue and a dressing that are to be welded. A dressing or other fastener containing such material may be applied to the wound site and welded in place. A composition may be a sealing agent used to effect a sealing of a sinus, tract, abscess, fistula or other cavity when placed therein. Heating the materials and/or tissues conductively or inductively effects the weld or seal.

Activator

The power supply used may be a constant current or a constant voltage power supply or may be a modulated current or a modulated voltage power supply. The power-supply is able to produce radiofrequency energy with a power in the range 10-10,000 W and, depending on the application, may be more preferably in the range of about 100 to about 1000 W. The power-supply may typically operate at frequencies of 100 kHz to 40 GHz. Preferably the frequency range is about 100 kHz to about 5.8 GHz and, more preferably, the frequency range is between 415 KHz to 4 MHz, 13.56 MHz, 90 MHz, 915 MHz, 2.4 GHz, 5.8 GHz.

The best operating frequency depends, inter alia, on the nature of the fusion composition to be heated, the geometry and chemical composition of the material to be heated, tissue to be fused, or the cavity to be filled. Regulatory issues also may be a factor in the choice of frequency. The output impedance of the power-supply is preferably matched to the input impedance of the applicator, described below.

The power-supply has several safety features incorporated therein. For example, the output is optionally of low or moderate voltage, such as <240V, preferably no more than 50V, which is traditionally considered a safe voltage, however some applications require higher voltage. The device is shielded for emitted or received electromagnetic interference. Thermal switches are incorporated within the device to shut it down if overheating occurs. Fast breakers quickly cut off the output if a power-output transient occurs. Multiple interlocks are incorporated within the device which prevents running the device with the cover removed. A foot pedal optionally is incorporated in order to minimize the possibility of unintentional activation of the device.

The RF device may provide for a continuously delivered magnetic field, such as is delivered through conventional induction heating and RF surgical devices. Alternatively, a pulsed field may be provided as, for example, is generated by diathermy devices. Pulsed fields may alternatively be generated using capacitors in a cyclic manner to successively charge and release current to the respective RF generating devices. In this manner, large currents may be generated over brief amounts of time, with successive pulses.

Pulsing the device in this manner also serves to minimize the effects of heat diffusion to surrounding tissue, over relatively long periods of time, by minimizing the duration of exposure to heating. Pulsing with a chaotic duty cycle can also reduce the time required to achieve the desired effect in the fusion composition.

Surgical Fasteners

Surgical fasteners comprise materials or a fusion composition that, upon activation, e.g., heating, will fuse with substrates such as tissues in order to produce a strong, uniform attachment or bond or weld. The surgical fasteners may take the form of sutures or of fasteners such as staples, pins, or clips. The fasteners optionally may comprise one or more spines or ridges whereby such fasteners may be inserted into the tissues surrounding the wound. The spine may be one or more microneedles.

The fasteners may fasten two or more substrates such as a tissue, dressing, or graft, to a tissue whereby a conductive element is integrated within the fastener or in an applied fusion composition material. The conductive element is capable of transmitting energy for the purpose of connecting the substrates together. The element optionally may be removed after the tissue fixation treatment through physically withdrawing the element or through dissolving and absorption as a result of physiological processes.

The fastening means may contain a mechanism for fastening tissues together that compresses the tissues upon activation. Such a mechanism of compression may include, for example, a hinge-like mechanism for clamping, an elastic material that shrinks upon activation and a shape memory alloy. At least one component of the mechanism has a different elasticity, changes configuration upon activation, or reacts to the applied energy with different characteristics than a second component in the device so that the tissues are compressed to each other.

The surgical fasteners may be activated by electromagnetic energy, preferably in the radiofrequency range, but optionally in the optical or microwave range, to fuse with the tissues thus resulting in a weld. Upon activation the fusion composition will form a connection between two substrates, such as a folded tissue, a plurality of tissues, a graft or non-biological element with tissue. Providing localized heating of surgical fasteners results in contraction of surrounding tissues around the fastener, which may improve the seal between tissues and fastener. For example, in the case where surgical staples are applied to seal a colorectal resection, leakage often occurs around the staples. Heating of the staples through an inductive or conductive process may result in heat transfer to the tissues surrounding the staples and contraction of the tissue around the staple, thereby improving the seal.

The surgical fasteners may comprise one or more proteins, such as elastin or collagen, or an ionic species, such as saline in a hydrogel, or a ferromagnetic material. These are activated in the presence of electromagnetic energy such that the materials will bond or fuse to tissues thereby effecting a connection between the tissues. The fastening means may also be or comprise a conductive element. The conductive element may be a fusion composition material, or integrated within a fusion composition, whereby the conductive element is inductively or conductively heated in order to activate it, i.e. generate heat in the system used for welding substrates together. Preferentially, the fasteners comprise a biocompatible material.

These fasteners optionally may be formed of laminates or comprise mixtures of varying compositions of susceptor and substrate or solely may comprise a susceptor. For example, a surgical staple may comprise titanium, stainless steel or a salt such as calcium phosphate or magnesium chloride or, alternatively, may comprise a core of stainless steel, with protein or other substrates laminated around the core. Additionally, the surgical fasteners may comprise at least one material that changes configuration upon the application of energy thereto. Examples of the material are a shape-memory polymer or a shape-memory metal. The material may shrink upon heating.

A surgical fastener may be a suture comprising a filamentous material such as a plastic, a protein, a fiber, or a combination thereof. A suture further may comprise a fusion composition. The surgical sutures optionally may have substantially pointed ends and may comprise ridges. The surgical fasteners optionally may have spines or projections, such as serrations, ridges or raised edges. Such ridges or spines serve to increase friction between the fastener and the substrate thus temporarily holding the fastener in place while the welding process is taking place. The spines may be placed at angles relative to the substrate in order to achieve greater friction or locking of materials due to forces in opposing directions. The ends of the suture may form a closed loop which upon the application of electromagnetic energy thereto effect a bond or weld with the tissue.

The activated fastening means may take advantage of the "skin effect" of induction heating and comprise different materials. The materials in the core may be somewhat shielded from heating occurring on the surface of the device. For example, it may be desirous to shield the interior of a fastener or suture that contains a pharmaceutical compound. By choosing the appropriate materials, frequency and power, the surface of these fastening means may be preferentially heated, with little or no heating occurring in the core of the device, thereby providing some protection to the inner core which contains the pharmaceutical.

The above embodiments should not be limited to the aforementioned fasteners, but should also include solid or semi-solid supports, anchors sealers, shields and spacers, collectively termed fittings. In this further embodiment are materials that may be placed in, on, or between tissues in order to fill gaps or defects, to seal gaps or spaces, or to provide support for structures. For example, supports and anchors composed of a fusion composition may be used to hold tissues or implants in a particular location. This type of support or anchor may limit movement or provide support to a structure to limit the effects of gravity.

Sealers, shields or spacers composed of varying fusion compositions may be placed at the junction of apposing tissues, or at a tissue interface to limit space between tissues, or to limit leakage from or into tissues. For example, in the case of anastomotic stapling during colorectal resection, a solid or semi-solid annular fusion composition structure may be placed in between the two separated lengths of colon prior to stapling. Upon stapling, the fusion composition may seal and act as a fitting between the two stapled sections, which, upon curing, provides a seal around the staples. A further embodiment of the invention therefore provides for solid or semi-solid fusion compositions that can serve as fittings between two substrates, either to seal where the substrates are already secured, as in the case of sealing over anastomotic staple lines, or to secure the substrates themselves, with no prior means of securing.

Ferroelectric and shape memory alloys may be incorporated into the design of the fasteners and fittings as well. In the case of ferroelectric materials operating above their Curie point, free positioning may be possible. Below a Curie point, actuation is possible, and may be achieved through direct excitation, or through inductive excitation while coupled to a susceptor.

Applicator

Applicator geometry greatly affects the distribution of the resultant electromagnetic field. There are several different possible designs for the applicator. The most efficacious design depends on the procedure for which it is used.

Applicators may be used to position and hold surgical fasteners. The applicator may be used to hold the suture ends in proximity to one another and in proximity to a conductive element and may incorporate a coil for inductive heating. Such an applicator may also be used endoscopically. The applicator has a means of holding two ends of a suture in place while fastening the substrates. The suture also may have ridges and a tubular component for locking of the suture in place. An applicator may comprise a ridged structure to complement a ridged suture to more firmly position and attach the suture to the substrates. The applicator may comprise means of applying pressure to position the surgical fastener. Pressure may be created with a spring mechanism or with a gas.

The ends of the sutures are juxtaposed to one another in opposite directions so that the welded area has a low and compact profile with respect to a surface to which they are attached. A tensioning and activation device may be applied to the suture ends in such manner as to secure the welds while positioned against the surface of the tissue to be secured. This aspect provides for a low-profile, high tension weld whereby it is not necessary to lift the suture above the tissue while applying tension and activation energy.

An applicator may comprise a forceps-like instrument to position and hold a suture to subsequently deliver energy to the suture to effect the weld. Furthermore, an applicator may hold the suture ends in place such that they are in proximity to an induction coil or conductive element. An energy generating mechanism present in the applicator, for example, an induction coil and an energy source, may be employed to weld or "activate" the suture once positioned by the applicator.

Furthermore, an applicator may load one or more fasteners such that pressure may be exerted to the fastener, either manually or by a pressure generating mechanism in the applicator, such that the fastener is made to attach to one or more substrates. An energy generating mechanism present in the applicator, for example, an induction coil and energy source, may be employed to activate the fasteners once in place. The applicator may preferably contain a mechanism to "load" additional fasteners automatically, allowing fasteners to be applied in succession.

For conductive heating an electrically conductive element may be used. The electrically conductive element may terminate in exposed terminals and may be incorporated into a material. The conducting element may be coupled to a current source or high frequency voltage source through the terminals. The conducting element may be linear, coiled, or consist of small three-dimensional conducting nodes connected by fine linear elements. The conducting element is arranged within the material in a particular geometry to result in a non-uniform heat and, thus, weld across the area of the material. The conducting element may be or comprise a metal, a protein, a ferromagnetic material, a pharmaceutical, a conducting polymer, or an ionic solution. Additionally, the conducting element may be embedded within a fusion composition or may be separate from but proximal to the fusion composition.

The electrical energy, i.e., a high frequency voltage or current, applied to the conducting element may be provided by at least one active terminal, a battery or an active electrode and a ground electrode. The active terminal may be an electrode array having a plurality of isolated electrode terminals. Both the active and ground electrodes may be embedded within a fusion composition. An active electrode may be embedded within a fusion composition and the ground electrode may be located distal to and external to the fusion composition. Optionally, the electrical energy may be modulated by a switch. Alternatively, the conducting element may have a geometry, e.g. a coiled configuration, that efficiently inductively absorbs ambient radiofrequency energy.

Additionally, a heating element with impedance greater than tissue may be used. The heating element is electrically positioned in series with a tissue, a conductive element and a second conductive element of lower resistance so that current flows through the tissue and the first element resulting in preferential heating of the element. A second conductive element with impedance less than tissue is in electrical series and grounds the current. Alternatively, a heating element with an impedance less than tissue is positioned electrically parallel with a tissue. Current flows through the tissue and heating element preferentially heating the element; a further conductive element with an impedance less than the tissue and the heating element taken together is in electrical series and grounds the current.

In the case of induction heating, a probe comprising an electrically conducting material, such as copper wound in the shape of a solenoid or of a coil, can be connected to the activator, e.g., a source of RF energy, in order to produce a strong and uniform magnetic field along the long-axis of the coil. Other probe shapes, for example antennas, may prove more suitable for particular applications. The coil or conducting material sets up an oscillating magnetic field, which inductively couples to a conductive material, i.e., conductive absorbers or susceptors, in the fusion composition or to the fusion composition itself. The induction coil may be located proximally to or at a distance from the fusion composition. Fusion compositions used internally in tissues may be activated by a coil located externally to the body.

Heat is produced through physical movement of the conducting material and/or the establishment of eddy currents within the conducting material or the tissue and/or composition and/or hysteresis losses and/or viscous, i.e., frictional, heating. The heat diffuses into the surrounding fusion composition and adjacent tissue thereby causing the composition to cure, such as via protein denaturation, with subsequent molecular bonding thus effecting adhesion. Change in conformation upon exposure to an electromagnetic radiation is not limited to protein. Electo- and magneto-responsive materials, shape memory alloys and polymers are examples of other substrates that may be utilized in organisms in order to achieve a desired effect. The adjacent tissue also may take part in the fusion process by being altered by the transient presence of heat. For example, the adjacent tissue (or the fusion composition) may mechanically shrink upon the production of heat, and this shrinking can lead to mechanical fusion of tissues with tissues or with other biocompatible materials.

Such a coil is most suitable for inductively heating materials positioned within the turns of the coil. The coil can be made in such a way that it can be opened up thus allowing a tissue, such as a blood vessel, to be positioned within the coil which then closes and completes the circuit. Alternatively, the magnetic field can be externalized from the interior of the coil with the use of a core material, such as is used in transformers. The core material may be of a magnetic material or, optionally, a powdered magnetic material, so that heat production in the core is minimized.

If required, the coil can be cooled by encapsulating it in a liquid-tight envelope, e.g., glass, through which a cooling fluid of low electrical permitivity, such as low viscosity mineral oil, can be circulated. Other means of enhancing cooling may be achieved by using hollow tubing for the electrically conducting material, such as copper wound in the shape of a solenoid or coil, through which a cooling fluid, e.g., water, can be circulated. The advantage of such a scheme is that the dielectric property of the cooling fluid is irrelevant because it is contained within the conducting coils and not on the outside where it would be inductively coupled to the produced magnetic field. Optionally, the tubing material may be coated in a smooth biocompatible non-adhering material, such as Teflon, titanium or gold, or a decomposible material such as pullulan, so that heated tissue will not adhere to the applicator.

Other applicator designs allow for a relatively strong magnetic field to be produced exterior to the wire or tubing. For example, applicators may be designed such that the field is produced above or below the plane of the conductor. Depending on the design, the strongest field may be produced below each separate coil or the strongest field may be produced in a single position below the coil. Optionally, the applicator can be bent into a particular shape whereupon the distance between the material to be heated and the conductor that makes up the applicator is minimized. This provides for an efficient use of energy. Additionally, the applicator may be shaped to be symmetric around an axis and is designed for use inside a hollow anatomical structure, such as a blood vessel.

A ferromagnetic material, e.g. pole-piece, may be positioned partially in the magnetic field produced by the applicator, thereby allowing the field to be skewed or transferred to the end of the pole-piece, thus producing concentration of the field lines and providing greater accessibility to the field. At high frequencies, it may be beneficial for this pole piece to be made substantially from powdered ferromagnetic materials or thin laminates in order to minimize undesirable heating in the pole piece itself.

The applicator may be a clamp-like instrument having two arms pivotally connected at the center for scissors-like action. The first ends of the arms are attached to two induction coils, or to a coil which is separated into two parts. The second ends of the arms function as a handle with which to manipulate and position the induction coils proximally to a position of interest. The coils may be coated in a smooth non-adhering material which comprises, for example, teflon, titanium or gold.

Using the scissors-like action of the clamp, the instrument is positioned around and proximal to the biocompatible fusion material such as around the tubular configuration used for vascular anastomoses. The coils can be attached to a radiofrequency power supply or activator that produces the oscillating magnetic field within the coils. Alternatively, a single coil may be made in such a way that it can be opened up thus allowing a tissue, such as a blood vessel, to be positioned within the coil which then closes and completes the circuit. In some aspects of this embodiment the activated surgical fastening means is positioned in relation to the substrates by the applicator. An example of an applicator utilizes pressure to position the surgical fastening means. In such an applicator, the pressure may be created with a spring mechanism or with a gas.

Additionally, the applicator may be used endoscopically to apply, position and cure fusion compositions. Applicators and coils must be sufficiently small to fit through the shaft of a trocar or through a small incision at a vantage point such that the applicator may be viewed through an endoscope. Also provided are endoscopic devices that are not affected by the alternating magnetic fields generated from power supplies used in this invention. For example, sensors, cameras, wires and fibers placed inside a trocar would have to be shielded from the field. Further, trocar materials must be non-conductive or of sufficiently low magnetic permeability to not be heated during use.

Alternatively, an applicator may be used to deliver the fusion composition simultaneously, before or after the curing process begins. The fusion composition may be delivered through the shaft of a tube which travels down the center of the coil, or which is juxtaposed to the coil or to a conductive heating element. The material may be delivered through the center of a coil such that the composition is exposed to the magnetic field and heated. Optionally, heating is via conductive elements in contact with the fusion composition as it moves through an applicator. Heating optionally may occur through direct heating of susceptors in the fusion composition. Furthermore, for conductive heating, a coil may be present to maintain the fusion composition at a particular temperature.

Fusion Composition

The fusion composition may comprise formulations that may be used to secure tissues, cells, and other biological materials in place, or to one another. A component of the fusion composition acts as an adherend which forms a bond between substrates, or is used to fill defects or seal leaks. The fusion composition may be in a liquid, solid or semi-solid state and may comprise proteins and/or polymers dissolved or suspended in a biocompatible material such as water. The materials that make up the fusion composition are preferably biocompatible biological material when working with tissues, although the material may be non-biocompatible. The fusion compositions may be inductively or conductively heated and are able to produce a fusion in biomaterials. The biocompatible proteins may be a protein, preferably e.g., elastin, albumin or collagen, and are typically present at concentrations of 0.1-100%, more preferably 50-75%. The fusion composition may serve as the substrate.

Generally, the fusion composition may comprise wholly or partially, for example, a biocompatible polymer, a protein, a polymeric substance or a combination thereof. The protein may be albumin, elastin, fibrin, collagen, or a glycoprotein, e.g., cellulose, starch, chitosan, alginate, emulsan, pectin. The polymeric substance may be hydrogel, agar or sol-gel. Examples of biodegradable polymers are polylactide (PLA), polyglycolide (PGA), lactide-glycolide copolymers (PLG), polycaprolactone, lactide-caprolactone copolymers, polyhydroxybutyrate, polyalkylcyanoacrylates, polyanhydrides, and polyorthoesters. Examples of biocompatible polymers are acrylate polymers and copolymers, such as methyl methacrylate, methacrylic acid, hydroxyalkyl acrylates and methacrylates, ethylene glycol dimethacrylate, acrylamide, bisacrylamide or cellulose-based polymers, ethylene glycol polymers and copolymersm, oxyethylene and oxypropylene polymers, poly(vinyl alcohol), polyvinylacetate, polyvinylpyrrolidone and polyvinylpyridine. Optionally, protein primers, which are substances that exhibit groups that can cross-link upon the application of heat, can be added.

Furthermore the biocompatible material may comprise a pharmaceutical. The pharmaceutical may be an anti-coagulant, an anti-thrombotic, an antibiotic, a hormone, a steroidal anti-inflammatory agent, a non-steroidal anti-inflammatory agent, an anti-viral agent or an anti-fungal agent.

The protein may be a component of the fusion composition. Proteins are particularly attractive in tissue bonding applications in that they typically denature at temperatures less than 100° C. Denaturation can lead to cross-linking with other molecules, particularly other proteins, in the immediate environment while the proteins are either in the denatured state or upon their renaturation. Additionally, it is well know that many biomolecules and tissues often shrink upon the application and subsequent removal of heat (9) Heating fusion compositions that result in shrinkage or contraction of tissues surrounding the composition may result in an improved seal. Additional materials added to the composition formulations may result in greater flexibility, and tensile strength as well as optimum treatment times and temperatures.

The formulations will utilize commonly occurring tissue and proteins, such as albumin, collagen, elastin, but may also contain silk, lignin, dextran, or soy-derivatives, poly-γ-glutamic acid, combined with additives such as polyethylene glycol, glycerol, wax or hydrogel to improve the rheologic nature of the adhesive. Optionally, an additive, such as hyaluronic acid, can be added to the composition to enhance the mechanical strength of adhesives, such as sometimes done in laser tissue welding, or pre-denaturation may take place before application of the composition at the treatment site.

Cross-linked polymers are quite insoluble, but they can be swollen to different degrees depending on their cross-linking. Swelling can be initiated by changes in temperature, pH, solvent type, ionic strength, light intensity, pressure, and electromagnetic fields. Hydrogels can be made biologically inert or biodegradable and are easily derivatized, particularly with enzymes. They can be grafted or bonded onto other materials, even living tissue.

The equilibrium swelling degree or sorption capacity, i.e., swollen volume/dry volume, is one defining property of a hydrogel. Depending upon the formulation, the swelling degree can be widely varied as can the sorption rate, which is roughly proportional to the equilibrium swelling degree. Permeability to water, drugs, proteins, and other biomolecules can be varied over wide ranges depending upon the swelling degree or water content. Hydrogels may be a useful optional addition to the fusion formulation as they give it different thermal and mechanical properties and also allow for the incorporation of a pharmaceutical which can ultimately diffuse out of the fusion composition.

Electively, other materials such as fibrinogen or chitin or chitosan may be added to the composition to provide hemostasis and/or some degree of immediate adhesion. Materials such as calcium phosphate or polymethylmethacrylate also may be used, most beneficially, when bony material is the tissue to be treated. Finally, pharmaceuticals such as an antibiotic, may be beneficially added to the composition in order to provide some desirable pharmacologic event.

Optionally, destabilizing/stabilizing agents, e.g. alcohol, can be added as they have been shown to alter the denaturation temperature of the protein. For example, an increase in the concentration of NaCl in a protein solution, which is referred to as "salting-in" proteins, can increase the denaturation temperature of beta-lactoglobulin, while an increase in the concentraion of NaClO4, or "salting-out", reduces the denaturation temperature (10).

When proteins are exposed to either liquid-air or liquid-liquid interfaces, denaturation can occur because the protein comes into contact with a hydrophobic environment. If allowed to remain at this interface for a period of time, proteins tend to unfold and to position hydrophobic groups in the hydrophobic layer while maintaining as much charge as possible in the aqueous layer. Thus, by creating bubbles in the composition will serve to lower the denaturation point of the mixture. One method of creating bubbles is through the use of ultrasonic transducers.

Sucsceptors generally fall into the class of materials called enhancers, which generally increase the rate at which a certain reaction takes place upon exposure to an energy source. In some applicatons, susceptors may be used in electromagnetic sensitive applications whereby they may behave as transducers, converting electromagnetic energy to vibrational and heat energy that may drive binding reactions. Materials undergoing hysteresis losses or physical movement, such as via friction, may be susceptors. Conductive materials may be referred to as susceptors. Susceptors also may be substrates. The susceptor may additionally play a role as a transducer, whereby the energy transferred by induction is converted to heat or kinetic, e.g. vibrational, energy that results in a change in a particular target material. The susceptor material may be directly bound to the target or may be associated in the surrounding medium. The susceptor may form a dipole. Alternatively, the electromagnetic energy absorbing species may be a dye.

Another form of transducer may be used to convert vibrational energy from an ultrasonic transducer to heat energy in a sample containing ultrasound contrast agents. These ultrasound contrast agents are typically micro-bubbles used to enhance an ultrasound image by virtual of providing contrast against tissues with different densities. Such microbubbles also may be added to the fusion compositions of the present invention, with or without other susceptors. Upon exposure to ultrasound, these microbubbles may vibrate within the fusion composition to produce heat, which in turn can be used to cure the composition. Thus, micobubble contrast agents may be used as enhancers to effect tissue fusion as described by the invention. Thus, fusion compositions may contain enhancers to cure a material upon exposure to high frequency vibration such as generated by ultrasonic transducers. Susceptors may generally encompass metal particles, enhancers and ions.

The conductive materials can be inductively or conductively heated and are added to the composition in amounts typically in concentrations of about 0.1 to about 25%. Higher concentrations may be used under circumstances where effects of the conductive materials on living systems are not a factor. The material may be composed of salts or other ionic substances or metals of variable size depending on the operational frequencies.

The fusion composition may be charged, by virtue of not being at its isoelectric point, or may have charged molecular species present which serve to interact with the electromagnetic field described supra. Alternatively, a metallic material may be added to the composition. The metallic material may be an alloy with a curie point in the range of 42-99° C. The metallic material is preferably biocompatible when working in a living system.

The conductive materials that can be inductively heated are added to the composition in amounts typically of about 10% by weight, although other concentrations can be used, but not limited to 0.1-25%. The material may include biocompatible ionic species such as salts, e.g., sodium chloride, or other ionic species, biocompatible nonionic compounds with high dipole moments or metals of variable size. For example, nanometer sized particles to macroscopic sized particles up to 1 mm in size can serve as effective susceptors. Alternatively, the conductive material may take of the form of a fine conductive lattice or mesh, such as available from Alfa Aesar Inc (Ward Hill, Mass.).

Example of materials that may be useful by themselves, or in alloys, in the present method and composition are tantalum, niobium, zirconium, titanium, platinum, Phynox, which is an alloy of cobalt, chromium, iron, nickel, and molybdenum, palladium/cobalt alloy, magnetite, nitinol, nitinol-titanium alloy, titanium, which optionally may be alloyed with aluminum and vanadium at 6% Al and 4% V, tantalum, zirconium, aluminum oxide, nitinol (shape memory alloy), cobalt (optionally alloyed with chromium, molybdenum and nickel, or optionally 96% Co/28% Cr/6% Mo alloy), iron, nickel, gold, palladium, and stainless steel (optionally biocompatible type 316L).

The conductive materials may take the shape of a mesh, fibers, macroscopic and solid materials, flakes or powder. The conductive materials may be anodized and may further be encapsulated in materials such as liposomes, compounds such as calcium phosphate, polystyrene microspheres, pharmaceuticals, hydrogels, or teflon. The conductive materials may also be complexed with glass and ceramics. These complexes and encapsulating materials may minimize immune responses or toxic reactions to the conductor, could induct a desirable pharmacologic event, or could enhance the inductive coupling to the activating magnetic field. Salts, such as calcium chloride, lithium chloride or sodium chloride are also conductive.

The rheology of the fusion composition can be important. For example, producing the composition in a low-viscosity liquid form would allow injection through a cylindrical pathway such as a trocar or working-channel of an endoscope. A higher viscosity or semi-solid material can be applied to a tissue and will stay in place prior to activation and provide mechanical support after activation. A solid formulation could be shaped, for example, as a tube, which then could be positioned in a tubular anatomical structure, e.g. blood vessel or ureter, again providing mechanical support prior to and/or after activation.

Other shapes may be more appropriate for different procedures. For example, a flat-sheet of composition would be suitable for sealing a large area of skin or soft-tissue, while a solid cylinder could be most appropriate for placement in the cavity left behind after a cannula is extracted. The material alternatively may be molded into a tape, which can be applied to conform to the surface of planar and irregular-shaped objects. A pourous structure of the fusion formulation might be beneficial for the subsequent in growth of cells. It is contemplated that the conductive material itself, when distributed throughout the treatment area, would employ the endogenous proteins in production adhesion, thus precluding the use of an external protein in the formulation.

For use in vascular anastomoses a preferable shape for the biocompatible fusion material may be tubular, or curved. The shaped fusion composition may further comprise a conductive material or conductive element, such as a metal wire, that is helically shaped and uniformly coiled within the biocompatible material. Alternatively, the conductive element may be distributed asymmetrically within the biocompatible fusion material so that the element is positioned where heat distribution is preferable.

The conductive element may optionally be positioned on the inside surface, the outside surface or on both surfaces of the tubular device for heat transfer to the tissue that is in contact with the biocompatible material in order to effect a bond. Application of electrical energy to each end of the helical conductive element by, for example, an electrode or induction of an alternating magnetic field around the device heats the conductive element to a critical temperature whereby the physical changes in the biocompatible material take place.

The shaped fusion composition of the present invention may also contain an energy-absorbing material in addition to the biocompatible material that efficiently, as compared to human tissue, absorbs electromagnetic energy. Such energy-absorbing material is analogous to the conductive elements but are more particulate, i.e., not as macroscopic in structure as the conductive elements may be. The distribution of the energy-absorbing material may be such that more incident electromagnetic energy is absorbed where it is desired to produce more heat. This distribution is similar to the asymmetrical distribution of the conducting elements. The energy-absorbing material may be, for example, conducting polystyrene microbeads, magnetic or metal-containing microbeads or nano-particles, colloidal metals, conducting polymers, or strongly ionic or polar molecules.

The composition optionally may have different additives depending on the material to which adhesion is required. For example, vascular graft materials composed of polytetrafluoethylene (PTFE) or Dacron may complex with denatured albumin. Alternatively, gelatinized PTFE, when used as one of the components of the fusion composition, could adhere to the PTFE in situ, thus effecting the desired result. Furthermore, heat-curable adhesives are included in the fusion composition. For example, heat-curable polymethylmethacrylate (PMMA) may be used to fuse bone components to one another, or to fill defects.

The fusion composition may incorporate a support lattice, such as can be made from, for example, porous calcium phosphate, polylactides, silk, PTFE or dacron, or a conductive material such as fine stainless steel mesh. The support material would allow for the fusion composition to be formed into a particular shape suitable for application to a particular anatomical structure. A conductive lattice would allow for inductive heating as well as mechanical support. Also, the efficiency of heating the fusion composition may be improved through the addition of ions in sufficient concentration to result in dielectric heating whereby ionic conductivity serves as a "bridge" between small particle conductive materials in the fusion composition.

The fusion composition may be in a formulation effective for membrane barrier function disruption. Specific formulations are chosen such that electromagnetic energy absorption is maximized relative to the surrounding medium. This may be accomplished through the addition of electromagnetic energy absorbers to the formulation. Further, many pharmaceutical or diagnostic compounds can be modified by either the addition of such energy absorbing groups or by selecting those that minimize absorption to maximize the effects of the electromagnetic energy on a particular formulation relative to the surrounding medium or tissue. Therefore, a new class of compounds is defined that have unique permeability, migration and deposition characteristics as a result of the addition of electromagnetic energy absorbing groups that function in the presence of, or following a treatment of electromagnetic energy as described herein.

These molecules possess different characteristics by virtue of the addition of groups or structures that absorb energy in a characteristic way. One result is that energy may impart momentum to the altered molecule causing it to move relative to the medium which contains it or applied energy may result in excitation of the molecule to cause a further change in that molecule. For example, rapid heating of a molecule, which preferentially absorbs energy relative to its environment, by radiofrequency energy or by microwave energy, could result in direct activation of a specific activity or cleavage of a heat-sensitive linkage thereby releasing an active moiety.

The compounds and formulations are designed to include both physiologically active groups and molecular groups which maximize the absorbance or reflectance of energy to achieve the desired effect. This is analogous to pro-drugs that release an active drug upon cleavage, usually enzymatic cleavage. Another analogy is found in photodynamic therapy whereby molecules absorb photons resulting in a transition from ground to an excited singlet state. This is followed by the transfer of energy to ground state oxygen in the nearby environment, whereupon the oxygen is excited to the singlet state, commonly known as ozone, which is toxic to cells.

Formulations may be chosen to effect deposition of a drug or a pool of drugs in a desired region of tissue or of cells. Modified molecules, such as pharmaceuticals with peptide or protein extensions, can be allowed to migrate to the region of interest, and may be activated to cross-link with the proteins in the target tissue. Alternatively, the complex may be allowed to be taken up by the cell, and then activated, preventing it from exiting the cell.

Pharmaceutically active compounds may be modified by the addition of groups that readily form a dipole or serve as energy "sinks" such that localized currents are induced when exposed to appropriate electromagnetic energy, such as radiofrequencies or microwaves. The addition of such groups would result in enhanced molecular vibration and/or migration of intramolecule electrons that may further weaken bonds in the modified molecule, or may result in a structural change to that molecule.

The carriers selected act as "sinks" for the energy whereby the energy is absorbed preferentially to the sink to limit exposure to the functional groups. Alternatively, molecules may be developed that have functional groups attached to a backbone molecule that is susceptible to cleavage when exposed to electromagnetic energy as described herein. Specifically, radiofrequency waves may result in excess vibration of groups as they absorb the energy. Using a linker that is susceptible to cleavage when its atoms vibrate in this way will result in the release of the functional group of interest which could be a pharmaceutically active substance. Also, magnetic fields alone may propel molecules through a medium or tissue based on intrinsic magnetic properties or by the addition of, inter alia, magnetic groups or metals which may be susceptors.

Fusion compositions that cure based on heat-influenced changes in molecular structure may behave differently when the energy is pulsed. This is evident when protein samples are successively heated and cooled over short periods of time, which can result in variability in the cross-linking achieved following denaturation. Protein strands often unfold when heated, and re-fold as they cool. Successive cycles of heating and cooling could result in an increase in cross-linking events as the proteins fold upon and tangle with one-another. This in turn results in greater bond strength.

Alternatively, the fusion composition is optional or simply may comprise a conductive material. For example, tissue fusion may be accomplished by applying metal particles to the interface between two tissue faces, or between tissue and another material, and, upon application of an alternating magnetic field via induction, the heat generated in the metal will diffuse to the surrounding tissues to create a weld.

Patch

The device may be in a patch to be used externally or a small patch to be used endoscopically. Many different arrangements of the conducting elements, as described for the applicator, within the patch are possible and each arrangement would have a particular feature beneficial in certain circumstances. The conducting element may be arranged within the patch in a particular geometry to result in a uniform or non-uniform heat and, thus, weld across the area of the patch.

Electrical energy may be applied to the conducting element(s) within the patch via a battery incorporated into the patch. Given that the temperature rise necessary to cause the beneficial thermal alterations in the fusion composition are no more than about 60° C., and more likely only about 30° C., the energy available in the battery can be low enough that only a very small battery is required. This results in a convenient to use and yet disposable patch. A coil may be attached to a radiofrequency power-source external to and superimposed proximally to the patch will produce a magnetic field around the patch.

Upon being exposed to electromagnetic energy or to the heat generated thereby, the molecules in the material containing the electrically conductive element change in conformation, altering their interaction with each other or with molecules in the surrounding environment. For example, upon heating, protein may become more fluid, and flow into a second material, whereupon the molecules assume a different conformation upon cooling, thus enabling them to cross-link with molecules in the second material to form a weld or bond.

The second material may be composed of tissue, or may comprise, for example, a semi-permeable structure of carbon, of ceramic or of a polymer lattice such as a sol-gel or hydrogel. Additionally this second material may be an electrically conducting fluid or medicament that provides a pathway for electrical energy to reach the skin and effect tissue alteration, e.g., denaturation, thereby effecting a tissue-weld. Change in conformation upon exposure to an electromagnetic radiation is not limited to protein. Electo- and magneto-responsive materials, shape memory alloys and polymers are examples of other substrates that may be utilized in organisms in order to achieve a desired effect.

The patch may comprise the fusion composition. The fusion composition may be heated conductively or inductively via the conducting elements comprising the patch. The fusion composition itself may be the conducting element and is heated directly. For example, tissue fusion may be accomplished by applying metal particles to the interface between two tissue faces, or between tissue and another material, and, upon application of an alternating magnetic field, e.g., induction, the heat generated in the metal will diffuse to the surrounding tissues to create a weld. Alternatively, the fusion composition may comprise conductive absorbers or inductive transducers or susceptors, as described herein. Medicaments may also be incorporated within the fusion composition.

The conductive element is heated leading to thermal alterations of the fusion composition material which then effects a tissue-weld at the surface of the skin or of other tissue for endoscopic applications. The conducting element also may provide a means of measuring the heat generated in the system allowing for monitoring at a distal location. The conducting element may optionally be removed after the tissue fixation treatment, through physically withdrawing the element or through dissolving and absorption as a result of physiological processes. This may be accomplished, for example, through the use of conductive metals and polymers that are either solid or mixed in a semi-solid matrix.

The fusion composition may be heated by applying radiofrequency energy to a coil positioned around it or near it, thus causing a strong and alternating magnetic field within the fusion composition. For example, using a ferromagnetic material within the fusion composition, the fusion composition is heated by the external magnetic field until it reaches the Curie temperature of the ferromagnetic material. At this point the heating ceases until the material cools below its Curie temperature whereupon the heating cycle can be repeated.

Laminates, such as bandages or tape, may also be comprised of reactants that provide radiant energy in the form of heat directly to the adherend through an exothermic reaction. For example, laminates may include a layer of adhesive, a protective coating and an additional reservoir housing chemicals that, when activated, results in an exothermic reaction, thereby generating sufficient heat to radiate into the fusion composition nearby, to result in curing and fixing. Such a reservoir may be similar to those used in hand warmers.

It is additionally contemplated that the weld that holds the patch in place may take the form of an annulus. Positioned within the annulus is a material or medicament that is beneficial to wound healing. Examples of this material or medicament are a hydrogel or antibiotic ointment. Alternatively, the fusion composition may have an arbitrary shape and may or may not contain a medicament.

The fusion composition may incorporate an array of fine conducting elements such as, for example, metal or magnetic particles that may be heated by induction or a series of metal wires or mesh that may be heated conductively. The fusion composition may be cut with a scissors and placed over the wound to be treated. A second part of the patch is placed over the fusion composition and is used to inductively or to conductively heat the fusion composition through the application of radiofrequency energy via the terminals in the patch thereby effecting the tissue weld.

In order to effect a strong weld, it may be beneficial to pre-treat the skin surface before altering the fusion composition and tissue whereby the weld takes place. The patch may contain an array of microneedles within a fusion composition surrounded by an annular electrode which incorporates electrically conductive fluid. Upon the application of radiofrequency energy or a brief, e.g., a few microseconds, pulse or bipolar pulse of direct-current, tissue alterations take place in the skin concomitant with thermal changes to the fusion composition.

Additionally, electrodes incorporated within the patch can be excited by radiofrequency energy or a pulse or bipolar pulse of direct-current, whereupon a plasma is formed between the active and the ground electrodes. This creates alteration to the stratum corneum as well as beneficial changes to the fusion composition while leaving the epidermis unharmed. The plasma may also lead to the formation of transient cavitation bubbles that can also induce beneficial changes in the stratum corneum and/or fusion composition.

A safety interlock may be integrated into the patch such that the device cannot be utilized unless the interlock is engaged, and only under proper use. For example, the interlock could be mechanical, electrical or optical. In the "on" position or engaged, the device may be operational. In the "off" position or disengaged, the device would fail to be operational. This could prevent unauthorized use and would prevent the device from being used twice which would be unsanitary.

It is contemplated that inductive coupling most simply results in heating through the magnetization of particles or other ionic species, either with non-zero conductivity and magnetic permeability, e.g., a ferromagnetic magnetic, a diamagnetic magnetic or a paramagnetic materials, and typically impregnated in a biocompatible fusion composition or adhesive. Alternatively, coupling may occur with particles in a tissue, or associated with biomolecules or bioactive molecules in a reaction vessel. Representatively, the composition may largely comprise a protein, such as serum albumin, with the addition of a metal such as 300 mesh nickel flakes, 150 mesh stainless steel particles or salts such as 15% NaCl. The metal or ions act as a susceptor. The induced electrical currents produced in the particles and composition results in heat which then conducts into the area immediately surrounding the susceptor, resulting in a "melting" of the adhesive and perhaps the adjacent tissue. This melting can result in denaturation of proteins present in and around the fusion composition. Generally, the adhesive cools and forms a bond with the tissue. Mechanical shrinkage of the tissue and/or the adhesive may also result in a beneficial mechanical bonding, filling or sealing.

The adhesion effect may be a consequence of the proteins in the fusion formulation bonding, perhaps by cross-linking, with other molecules in the protein formulation, as well as the proteins in the adhered tissue, which may generally result from denaturation and renaturation. This bonding may be result in a "bridge" or "scaffold" between the molecules and the tissues, particularly when additional support materials are included in the fusion composition. For example, collagen fibers may provide a latticework or bridge for connective tissue, while Calcium phosphate particles may provide a scaffold for bone to grow into. The endogenous proteins in the tissue also may have been denatured and coagulated due to nearby heat production which may be critical to the adhesion strength.

In tissue, the temperatures needed to achieve protein denaturation, which may be a prerequisite for bond formation, range from about 45-85° C., and the heating times are very short since protein denaturation is essentially instantaneous once a critical temperature is achieved. Thus, the powers required for the present device and method are far less than those used in commercially available industrial induction-heating devices which are used for welding metals and plastics. Accordingly, the present invention can be produced for a fraction of the cost of commercial devices.

Control Elements

The present invention also provides a means to control the welding process by monitoring and regulating the heat generated or used in the system, so as to avoid overheating and damage to the materials and/or substrates, and to cure the fusion composition to provide a uniform weld. The fusion composition comprises a conductive material that has a thermal history such that the application of radiofrequency energy or electrical energy thereto generates an estimable amount of heat. The thermal history, i.e, temperature as a function of time, of the fusion composition and contacting tissue must be such that the beneficial chemical changes take place, e.g., denaturation, and yet little or no extraneous heat is produced which could otherwise lead to unwanted extraneous thermal damage.

According to Arrhenius Rate Theory, the rate of a chemical reaction is exquisitely sensitive to temperature, but only linearly related to the time that a particular temperature is held. Thus, it is of benefit to quickly heat the tissue and fusion composition from their ambient temperature $T1$ to a temperature beyond the threshold temperature $T2$ for the beneficial chemical change, but not beyond the temperature $T3$ for irreversible thermal damage to extraneous tissue. The duration of heating cycles illustrated may range from microseconds to many seconds.

Once the critical temperature $T2$ is exceeded, the device quickly cools because of the small mass of the conductive heating elements or absorbers within the fusion composition whereupon the heating cycle can repeat. When the heating is done in a time more rapid than the time it takes the heat to conductively dissipate out of the heated tissue and fusion composition, then the total amount of energy used and heat produced during the process is minimized. Depending on the thermal properties of the conductive heating elements and tissue, the duration of these heating cycles may be as short as microseconds or as long as milliseconds and the heating cycle can be repeated as many times as required to effect a suitable tissue fixation.

The conductive material may be a metal wire, a metal particle, a ferromagnetic material, a paramagnetic material, a conducting polymer, an ionic molecule, a polar molecule or a conducting microsphere. Additionally, the conductive material may be an energy-absorbing material, said energy-absorbing material comprising conducting polystyrene microbeads, a colloidal metal, a conducting polymer, a strongly ionic molecule or a strongly polar molecule.

Control over the process may be exerted by direct feedback monitoring of heat generation, or by prediction and measurement of the magnetization of the composition over time, with regard to its volume and mass. This feedback may arise from measurements of impedance changes in the applicator, as the tissue becomes part of the circuit during treatment, or devices such as thermocouples or infrared thermometers can be employed. A second order of control may be exerted through the use of ferromagnetic metals and alloys as susceptors which remain magnetized until reaching a critical temperature, the Curie temperature, when they cease to be magnetic. At this point the heating ceases until the material cools below its Curie temperature whereupon the heating cycle may be repeated. The ferromagnetic materials may be incorporated within a fusion composition. Use of visual cues, which change with temperature or according to rheological factors, may also provide the user a means by which to monitor the progress of a particular process.

The power supply used for curing the fusion composition may be a constant current or a constant voltage power supply or may be a modulated current or a modulated voltage power supply. For example, radiofrequency energy can be produced through circuitry powered by a battery and modulated with an external switch. Also the conductive or inductive heating process can be monitored by sampling changes in the first and/or second time derivative of the impedance of the tissue, comparing this derivative to zero and using this information to modulate the heating process.

Control of heat generation through the use of salt bridges, whereby ions in the form of salts, e.g. sodium chloride, are added to the fusion composition while in a liquid or semi-solid state. Upon curing, the flow of charges may be impeded through the increased viscosity associated with polymerization, denaturation, etc., resulting in a loss of conductivity. Thus, for example, when a fusion composition that is at least in part comprised of ions in solution is cured, conductivity falls and eddy currents are impeded. As a result, heating of the composition is impeded. In a related manner, conductivity in solid fusion compositions may be impeded when curing results in disruption of the conductive network.

Sequential rapid heating of biological targets, followed by cooling, has been shown to be a beneficial heating protocol in many laser therapies (1). This is because the temperature of the thermally sensitive target can be rapidly raised to beyond a threshold temperature, whereupon further heating is of no benefit. Instead the heat diffuses out into the surrounding tissue leading to undesirable thermal damage to uninvolved tissues. In order to maximize this benefit, it would be useful to rapidly pulse the fusion composition activator.

The temporal extent of the pulse can be as short as about a few microseconds and multiple pulses may be required to obtain the desired effect. Longer pulses may also be used, however, an overproduction of heat might induce undesirable damage to the proximal tissue. Generally, the pulse should be brief enough and of enough magnitude to induce heating of the conductive element so that the threshold for a particular molecular change in the biocompatible material and in the outer surface of the substrate is exceeded. The pulse also allows for incremental increase of overall heat to the system, provides for an appropriate amount of time for heat diffusion away from the conductive element, and minimizes the power needs of the power supply, i.e., activator, allowing relatively low power consumption as minimal average powers are utilized. Pulsing in this manner also minimizes cooling requirements for the systems.

There are many ways to pulse the instrument, for example, pulsing can be accomplished by electronic switching or by sequential discharge of capacitors. Concurrently with the discharge of the capacitor bank is the charging of an independent capacitor bank, which can then be discharged while the first bank is recharging. In this way, a high duty-cycle can be achieved which is particularly useful as a method for pulsing DC units such as used for diathermy.

A control element based on monitoring changes in eddy currents, which are generated in the fusion composition and substrate as a result of the electromagnetic field generated during the inductive heating process, may be used. The applicator coil or a secondary coil are used to monitor eddy currents in the reaction while it is taking place. This form of eddy current monitoring is related to non-destructive evaluation of materials. Eddy currents induced by a changing magnetic field concentrate near the surface adjacent to an excitation coil. The depth of penetration decreases with increasing frequency and is a function of electrical conductivity and magnetic permeability of the specimen. Sensitivity to defects and changes in conductivity depends on eddy current density at the target location.

Eddy current penetration decreases rapidly with depth. There is an increasing phase lag in the signal with increasing depth, as well as a change in the amplitude. This is the basis for differentiating signals at various depths and distances from the coil. Although the currents are restricted to flow within specimen boundaries, the magnetic field extends into the air space beyond. This allows the inspection of multi-layer components separated by an air space. As well, the signal produced by a flaw depends on both amplitude and phase of the currents being obstructed. A small surface defect and large internal defect can have a similar effect on the magnitude of test coil impedance. However, because of the increasing phase lag with depth, there will be a characteristic difference in the test coil impedance vector. This effect allows location and extent of a defect to be determined.

As regions in the fusion composition cure, electronic properties vary. For example, as ions are excluded from solution, changes in conductivity occur. These changes in conductivity can be detected by monitoring changes in eddy currents at various depths. Additional information, and sensitivity may be gained by using additional signals at various frequencies, or by pulsing the field to result in pulsed eddy current signals, or both. Pulsed eddy-current signals may consist of a spectrum of frequencies meaning that, because of the skin effect, each pulse signal contains information from a range of depths within a given test specimen. In addition, the pulse signals at very low-frequencies provide excellent depth penetration.

The simplest type of probe in the embodiment is the single-coil probe, which may be the applicator probe described supra. Sometimes it is desirable to use a probe consisting of two (or more) coils arranged in a transformer fashion and therefore known as a transformer probe. The primary coil induces eddy currents in the test object and the secondary coil acts as a detector. The use of this probe provides an enhanced signal-to-noise ration for detection, advantageous when deep penetration is required such as seeking internal defects.

These eddy current inspection methods are useful for detecting changes in any heat-cured specimen where conductivity changes as a result of heat generation, curing or otherwise. The methods are additionally useful for detecting flaws and differences in electrical properties among tissues, biological samples and other samples, and for detecting implanted materials of different conductivities. Therefore, it is an object of this invention to provide for a control, inspection and monitoring method, as well as devices that utilize eddy current evaluation in test samples. The techniques apply to, but are not limited to, heat base methods including laser tissue welding, RF electrosurgery and electrocautery, hyperthermia, and induction heating in tissues. Further, the techniques apply to the evaluation of electrical properties in tissues, tissue samples, biological materials and other samples both in vivo and in vitro. Such evaluation has utility in detection of tissue anomalies as well as in diagnostic testing in vitro.

Other means of controlling the heating process are contemplated. The temperature of the treatment site is measured concurrently with treatment. Activation of a fusion composition substantially comprising, for example, bovine albumin requires a threshold temperature of about 75° C. to activate and fuse tissue. Monitoring of the temperature of the tissue during treatment can be done with an infrared thermometer, thermocouple or other thermoelectric transducer. The analog output of the thermometer can be digitized and sent to a controller, which then alters the output of the fusion composition activator in order to heat the composition to the critical threshold temperature, but not beyond where deleterious thermal damage may result.

Changes in particular physical properties, such as impedance, of the treated tissues may be directly monitored. When tissue is thermally altered, it's impedance changes. For example, alteration or removal of the stratum corneum of skin in an effort to enhance transdermal drug delivery also results in a dramatic reduction of skin electrical impedance. This reduction can be measured directly with electrical current and compared to a look-up table where the impedance is calibrated against temperature. The impedance can then be used to alter the output of the fusion composition activator.

Changes in the electrical load placed on the activation device as a consequence of changes in the electrical properties of the treated tissue may be monitored. The tissue being treated acts as part of the electrical load presented to the fusion composition activator. Changes in the electrical impedance of the tissue resulting from heating are sensed by the activator. When this phenomenon is calibrated against actual temperature measurements, this can be used to alter the output of the activator so that the critical temperature is reached.

A cooling system at the tip of the applicator or a cooling system allowing coolant to flow onto the target site may be added. For example, it may be necessary or desirable to heat tissue below a surface without heating the surface. One means is by spraying a coolant onto the surface simultaneously with the application. One example is heating cartilage lying beneath the skin surface.

Provided herein are methods and devices for determining the degree to which the fusion composition is cured. An indirect measure of the degree of curing may be obtained using thermal indicators in the fusion composition. These indicators may be heat sensitive such that dyes or other indicators are released upon reaching a desired temperature, or they may be heat sensitive materials that change characteristics upon heating, e.g. heat sensitive dye.

These methods include thermal sensitive materials that react when the fusion composition reaches a target temperature. Examples include the release of markers from thermal sensitive capsules, for example, liposomes, glass coated, temperature sensitive dyes. Another example is thermal sensitive compounds used in laquers. Properties of the cured fusion composition also change upon curing. For example, the rheology of the material may be different upon curing, changing, for example, to a more viscous liquid, or from brittle to elastic. Such changes may be measurable by evaluation of the elasticity or rheology by applying pressure or through vibrational analysis, for example by ultrasonic probing. Optical probes, for example using reflectance measurements of opacity, loss of reflectance, or absorption at various wavelengths, may also be used to detect changes in the fusion composition upon curing.

Compositions may also include materials that are heat-stable and elastic over a greater range of temperatures. Wetting materials also prevent the compositions from drying. Pre-denatured albumin has also been shown to result in greater tensile strength (Welch, McNally). More of a problem is burning tissue as a result of overheating. Wetting solutions or thermally conductive compositions help to dissipate heat. Short exposure times also limit heat. Signal to indicate time elapsed over a certain region may be useful, as would heat detection.

Also described herein are methods and devices for inductively heating non-conventional substrates, i.e. biological materials such as cells, tissues and molecular entities, in order to cause conformational changes that result in unique properties with regard to tissues. In particular, the principles of induction heating are applied to treat biological materials and cause them to join to one another or to non-biological materials. Upon inductive heating, proteins, and possibly other biomolecules, present in the tissues take part in a fusion process that allows tissues to adhere to one another. The fusion process may involve the addition of adhesives between the tissues that could include susceptors that assist the process of inductive coupling. These methods and devices may be used to anastomose tubular structures such as blood vessels or ureters.

The inductive heating methods use devices providing radiofrequency energy to generate an electromagnetic field to produce heat substantially within a fusion composition. The fusion composition may function as a fusing or bonding agent between two or more elements of a tissue or as a sealing agent to seal a sinus within a tissue, such as a vascular access defect or other defects within a tissue. For example, in these methods the fusion composition may comprise a conducting absorber or susceptor to transduce the electromagnetic field to heat production within the fusion composition. The methods encompass a means of monitoring the amplitude or persistence time of the electromagnetic field generated during application of the method.

Additionally, the fusion composition may function to effect a weld between a tissue and at least one other substrate, including the fusion composition. The method provides a means of monitoring the extent of the weld, such as via feedback monitoring of temperature or impedance. The substrate optionally may comprise, but not be limited to, a tissue or a material commonly used in medical implants. For example, medical implants may be fixed in place using the aforementioned procedures, therefore preventing migration.

More specifically, one method provides a means of cauterization and dissection of a tissue without contacting the tissue. A conductive composition is applied to the surface of a substrate, such as a tissue which is leaking fluids, e.g. bleeding. The composition is heated through induction using the devices described herein to a point where the tissue beneath the composition is cauterized as a result of the heat generation. Application of additional heat can be used to cause separation of the tissue, with simultaneous cauterization.

Similarly, a conductive composition is applied to the surface of a substrate, for example, a tissue to be dissected. The composition is heated through induction to a point where the tissue beneath the composition is separated as a result of the heat generation. As a result of heating and separation, the tissue beneath the composition is cauterized, thus limiting bleeding.

The methods and devices described herein may be utilized to induce conformational changes in biomolecules and bioactive molecules such that they may react in a unique manner or such that the rate of reaction is accelerated. The enhanced reactions are useful in a range of biological applications, including, but not limited to, wound healing and tissue fusion, deposition of pharmaceutical agents, fixation of implants and tissues, development of multi-laminate and multi-vesicular delivery agents, and cosmetic alteration of tissues.

In one method a device utilizes a radiofrequency electromagnetic field to inductively transfer energy to reactants thus accelerating a biochemical reaction. One or more of the reactants taking part in the biochemical reaction may have a molecular or macroscopic absorbing species or transducer, i.e., susceptor, linked to it, or in close proximity to it, for the purpose of enhancing the transduction of energy from the electromagnetic field to the reactants. Optionally, the reactants may be proteins, the molecular transducer or susceptor may be an ionomer and the macroscopic transducer may be a metallic nanocrystal or particle.

In a similar method the device is utilized for inductively transferring energy to reactants, in vivo or in vitro, thus accelerating a biochemical reaction. This accelerated biochemical reactions have multifold beneficial uses. For example, the reaction results in the fusion of molecular species to one another, in the modification of an artificial or naturally occurring membrane to increase permeability thereof, or the release of an active drug moiety from a pro-drug.

Accelerated biochemical reactions also may be used in vivo, for example, the fusion of tissue separated through surgery or trauma, e.g., an anastomosis. A fusion composition may be utilized in such an instance. The fusion composition may comprise, although not limited to, a type of heat activated adhesive and a transducer. The adhesive may be, for example, a protein found in body tissues and transducer may be metal particles or ionic species. The transducer is used to convert electromagnetic energy to another form which is useful in activating the adhesive. For example, energy may be converted to heat or vibrational energy which in turn applied to the protein in the fusion composition alters its molecular conformation and accelerates a reaction between the protein and tissue. This reaction may be denaturation of the protein.

It is contemplated that such a fusion composition may be used as an adhesive to reinforce staples or sutures or used in sutureless anastomosis. The fusion composition may be formed into a laminate or "tape", which can optionally have a biocompatible outside surface which dissolves upon exposure in bodily fluids. The surface may be made up of a material, such as pullulan, which would serve to prevent the operator from sticking to the fusion composition, which may have an adhesive nature, even before activation, while he or she applies it to the tissue to be fused. The tape may optionally contain a pharmaceutical, such as an antibiotic, thus providing a high dose of relevent drugs locally at the region of fusion. This may also serve as a depo-drug delivery mechanism whereby the pharmaceutical leeches out of the tape slowly over time, which in particular situations, can be beneficial. This may serve to minimize deleterious side-effects. Examples of such application may be after a colorectal surgical procedure to reinforce integrity of the suture line or to stop bleeding and protect the puncture wound after dialysis.

Additionally, in the field of cancer therapy, it is known that the efficacy of chemotherapeutic drugs in inducing lethal damage to malignant cells increases with the increasing time that the drug is present adjacent to or within the cells. An ongoing problem in cancer therapy is getting malignant cells to retain chemotherapeutic drugs. A novel and potentially powerful form of cancer therapy would involve the in situ inductive biomolecular alteration or activation of a chemotherapeutic drug/magnetic particle conjugate which would serve to make the cancerous tissue retain the drug. Migration of the altered drug from the desired site of action would be minimized. It is contemplated that the decreased migration is the result of direct binding of the altered molecule to another species or through an alteration of its mobility characteristics.

Additionally, the methods and devices are utilized as a means of inducing conformational changes related to curing, denaturing or other alterations of biological material either in molecular or tissue form. Examples include the alteration of molecules, such as, denaturation of proteins and the release of active drug or biologic agents from pro-drugs or pro-biologics with heat-cleavable or molecular vibration sensitive linkages. Examples also include the enhanced binding ability of protein and other molecules, including certain molecules in receptor-ligand interactions.

Similarly, the methods and devices are utilized to aggregate proteins and other biological materials to form structures which are useful, for example, in rebuilding tissues, fusing and fixing tissues and for creating aggregates of liposomes and proteins for drug delivery and deposition. For example, spherical or planar protein or lipid composites, including liposomes, may be fused together using inductive heating to form multi-laminate or multivesicular materials. Multi-vesicular liposomes may be produced in this way. Such multi-vesicular liposomes and multi-laminate materials are useful for as, inter alia, drug delivery agents, or carriers.

The protein-susceptor combination may be used to connect membrane structures such as those in liposomes or in living cells. For liposomes, modifications are made to the formulation to include protein and susceptor in the liposomal membrane. Upon activation, the proteins in the membranes cross-link to form aggregates of one another and of the liposomes. By controlling time and energy applied, different sizes of these multi-vesicular liposomes may be formed. Such multi-vesicular liposomes are useful in deposition drug delivery as they deposit in a region and are slow to dissolve or resorb, thus resulting in slow, sustained release of the contents. Clinical applications of either single or multi-vesicular liposomes also include filling the carrier with a pharmaceutical substance, allowing it to localize in a particular region of tissue, then activating the modified liposome resulting in cross-linking of the membrane proteins to proteins present in the membranes of tissue cells of the region. Thus, the liposomes became deposited on the tissue of choice.

Furthermore, these methods and devices may be utilized to form deposition drug delivery and measured release agents comprising multi-laminate sheets or multi-vesicular liposomes. The sheets may be incorporated with drugs and the structure may be deposited in a specific tissue region or cavity. Degradation of the vesicles or laminates over time may result in the release of drugs until dissolution is complete. By varying the number of laminates or vesicles, the duration of degradation may be controlled.

Similarly the methods and devices described may be utilized to fuse biomolecules, bioactive molecules, laminates and multi-vesicular liposomes to tissues. An example of an application of this embodiment includes the deposition of biomolecules and carriers to tissue where the biomolecule or carrier may comprise a protein that is capable of cross-linking to surrounding tissue or cellular proteins. In this example, the biomolecule may bind intracellularly or extracellularly. The biomolecule or carrier may thus be localized in a desired region, such as a tissue or in a cavity. This application, for example, provides a means for localizing chemotherapeutic agents at the site of a tumor or intracellularly in certain situations, thus increasing the likelihood that a target may receive therapeutic benefit.

Furthermore, the methods and devices provide for the formation of certain structures that are manufactured using inductive processes. These structures may also take benefit from induction during their use in biological environments. The structures may include, but are not limited to, a scaffold, or porous and filamentous structures comprising biological materials such as proteins. Additional components, such as energy absorbing species, e.g. susceptors, may be included in the structure and may act as transducers. The susceptor material further may be particulate or of a desirable shape, such as, for example, a coil or rod.

These structures are useful, for example, as support during the reconstruction of tissue, filling in or sealing tissue defects, or in fixation of tissue with tissue or implants. These structures may allow for growth of the tissue in and around the support. For example, during bone reconstruction, it may be desirous to fill defects using a scaffold or porous matrix comprising protein and calcium carbonate such that the matrix provides initial integrity and strength, but also allows for tissue to grow into pores over longer periods of time.

The invention further provides irregular structures that may preferentially interact to varying degrees with the magnetic field produced by the applicator. Thus gradients of susceptor material may be positioned in a structure such that the material may be heated at different rates when exposed to a constantly changing field or may heat relatively linearly when exposed to a changing field. For example, a linear filament may comprise a protein and susceptor where the susceptor is at a greater concentration proximally than distally, with regard to the applicator. Thus, an increased concentration of susceptor distally from the applicator results in more efficient heating, compared to proximal sections that are at low susceptor concentration. This, in effect, compensates for the decreasing field at distances from the applicator.

The applications described herein are not limited to cells and tissues of animals. The methods, devices and formulations described herein have application in other living systems, or those derived from living systems. For example, plant tissues may be grafted to one another using the techniques described in this invention. Such grafting may be used to hybridize plant species. Cells of various organisms may also be fused to one another to create multi-cellular constructs, or for fusion of cellular components.

The methods, devices and fusion compositions described herein have medical applications. Examples are, but not limited to, fixation, tissue reconstruction and/or other aesthetic procedures.

The shaped fusion material of the present invention is used to join tubular or approximately cylindrical anatomic structures, such as vascular vessels, to other tubular structures or to non-tubular structures. For example, in the situation where a patient is to undergo minimally invasive coronary artery bypass graft surgery (CABG), a surgeon gains endoscopic access to the obstructed cardiac blood vessel, whereupon dissection of the vessel at each end of the obstruction occurs. An appropriate length of a suitable bypass graft material, either man-made or a transplant, is positioned between the dissections.

The first end of the tubular fusion material is fitted over or inside the end of the healthy vessel in situ, and the second end of the tubular fusion material is fitted over or inside the bypass graft. The ends of the vessel and of the graft material are positioned to contact each other and a bond is effected between the vessel and the graft by applying RF to generate an external oscillating magnetic field or by applying a brief pulse of electrical energy to each end of the conductive element in the cylindrical device. Alternatively, the ends of the healthy vessel and of the graft tissue are everted around the outer edge of the tubular fusion material. In this instance the tubular device may have an appended second part comprising the biocompatible fusion material. The appendage may also comprise the conducting element or the energy absorbing material embedded within the tubular material.

Fixation of bones to bones, or bone-implants to bone, can be a very problematic procedure in surgery. For example, fixation of hip implants into femurs necessitates the use of cyanoacrylate glues, which bond nearly instantaneously upon contact. Incorrect positioning of the implant at the time of glue setting results in compromised results and may even require prosthesis removal, which itself may result in fracturing of the femur. The same problem can be said of bone-to-bone fixation. The fusion compositions of the instant invention are a significant improvement over the existing technology in that the bone or implant to be fixed in place can be coated in the fusion composition, or the site of fixation can be coated in the fusion composition, and correct positioning can be confirmed prior to activation of the composition with the electromagnetic field. This minimizes the chance of incorrect positioning.

Incorrect positioning prior to fixation can be a problem in itself in fixing soft tissues or therapeutic materials. For example, in treating incontinence, the bladder and urethra are stabilized by a surgery performed by placing sutures between the ligaments and tendons that support the pelvic organs and then tying them to the pubic bone. Alternatively, tissue may be sutured in place beneath the urethra and bladder neck for support. This can prevent accidental release of urine from the bladder when laughing, sneezing, or coughing. The methods of inductive heating to fix, bond, weld, or fuse tissue used in these procedures would fix the tissues in place.

Skin and other graft fixation, as well as securing bandages, is also an important potential use of the invention. Fixing grafts and bandages in place with the instant invention has the added benefit of minimizing the movement associated with securing tissues or bandages in place that have different flexion properties than the surrounding tissues. For example, bandages positioned over pressure-sores or the cutaneous ulcerations that can result from diabetes often move and rub the wound, thus preventing healing and perhaps even accelerating further decomposition of the wound.

The use of alloplastic implantable materials, often consisting of a polymeric shell filled with saline or silicone, are very commonly used in soft tissues, but can give rise to significant problems in surgery. They are commonly used to repair traumatic wounds, congenital deformities, and cosmetically unappealing appearance. However, an implant can occasionally become malpositioned thus requiring a revision surgery. Sutures are sometimes used to fix the implant in place, although migration of the implant, which can lead to poor cosmesis or therapeutic effect, can still happen. Autogenous fat transplants have been used for decades but have largely been replace by, injectable bovine collagen, first available in 1981. Zyderm and Zyplast (Collagen Corp, Palo Alto, Calif.) are now available and have been used with excellent safety records, with the major drawback of rapid absorption as illustrated by no histological evidence of Zyplast by 6 months and Zyderm by 3 months. Again, fixation of the implant in place, with or without the use of fusion composition, would both minimize post-implant malpositioning and undesirable rapid decomposition and absorption.

Reconstruction of tissue is done for both cosmetic, as well as therapeutic reasons. For example, chondral transplantation is sometimes done when the knee cartilage focally degenerates, perhaps due to local acute trauma. It is possible to take plugs from the interior aspect of the damaged knee and then position them close together in the defect thereby allowing reformation of the collagen surface. In other reconstruction situations, it is sometimes possible to simply position viable collagen tissue at the defect in the hope that tissue regeneration will take place, thus resolving the lesion. In either case, migration of the transplant must be minimized.

Plastic surgeons sometimes use porous hydroxyapatite implants which when implanted into the body allow normal tissue integration to occur. Also a non-porous paste comprising hydroxyapatite may be used. The fusion compositions described herein can be used to fix either the plugs, hydroxyapatite or collageneous tissue in place. Here, the fusion composition, optionally with hydroxyapatite added to enhance oseointegration, is applied first to the plugs, or mixed in with the collagenous tissue, and is manually positioned manually to take advantage of the fact that the fusion composition can be made highly viscous and so will stay in place prior to activation. Once correct positioning is confirmed, activation of the fusion composition occurs, either with an endoscopically positioned coil applicator or transcutaneously with an external coil applicator. Activation of the fusion composition eliminates migration of the transplant.

Thermal shrinkage is a relatively new procedure used to treat small tears of the anterior cruciate ligament (ACL), i.e., instability in the knee. The collagenous tissue in the ligament is "shrunk" in size using electrosurgical units, or holmium-YAG lasers. This shrinking results in tightening of the ligament, thus minimizing instability, and minification of the extent of the tear. Using the present invention, the ACL is heated transcutaneously or minimally-invasively with a small activation coil. The endogenous charged species may interact with the activation field, thus producing heat. Alternatively, the fusion composition could be applied to the ACL exactly where the heat and shrinkage is desired, thus enhancing the selectivity of the treatment and avoiding the heating of uninvolved tissues.

Keratoplasty is a procedure whereby the cornea is reshaped with a laser, or experimentally with heat from a radiofrequency device, thus changing the cornea's refractive characteristics and so, for example, reducing hyperopia. The instant invention provides a new way to perform this procedure. For example, by utilizing endogenous charged species in the cornea, an ambient electromagnetic field could be applied in a non-contact fashion, leading to heating of the charged species, and subsequent shrinkage of the corneal tissue. With an electromagnetic applicator of particular shapes, non-uniform electromagnetic fields can be created thus inducing non-uniform heating patterns and tissue shrinkage.

There are multifold aesthetic procedures which could be accomplished by the instant inventions. For example, hair removal, wrinkle removal, scar revision, facial resurfacing, port-wine-stain therapy, collagen reshaping, and tattoo removal are aesthetic procedures. Currently in some of these procedures, chemicals are used to elicit the beneficial response. Alternatively, lasers or electrosurgical devices can be used to heat the tissue, e.g. skin, thereby causing shrinking, coagulation and a cascade of healing events leading to the desired response. There is a new technique that involves a radiofrequency plasma and purportedly does not produce heat (Visage, ArthroCare Corp., CA). Chemicals are relatively difficult to use, lasers are very expensive, and the electrosurgical devices, e.g. Thermacool system (Thermage Inc., CA) is a contact system requiring the patient to wear a grounding pad and so has the same risks seen in classical electrosurgery.

The present invention may be used in tissue treatment procedures with the added benefits of being non-contact, inexpensive, and with only minimal operator skill necessary. It is contemplated that the radiofrequency energy generated through induction may result in hysteresis, eddy current formation (ohmic heating) and/or viscous heating in molecular entities within the tissues themselves. This effect is accentuated in the presence of ions or when high frequencies are applied and results in localized heating in the regions surrounding the affected molecules.

The hair removal technique of choice involves the use of a laser in selectively targeting melanin. Each hair has 3 distinct components of which one is the bulb, which lies near the insertion of the erector pili about 4 mm beneath the surface of the skin, where pluripotential cells cause growth of the hair follicle and where melanocytes also are present. During anagen, which is the active growth phase in the hair growth cycle, at which time hair matrix cells divide rapidly and migrate outward from the shaft and the melanin load is at its highest, laser therapy is effective. Basically, the laser radiant energy is converted into heat in the melanin thus causing irreparable thermal damage.

The problems are that the hair must be darker than the surrounding skin, hypopigmentation or hyperpigmentation may result, and the radiant energy of the laser must penetrate to at least 4 mm. The present invention, when used for hair removal, has the added benefits of much deeper penetration of the electromagnetic energy, and works independently of melanin content and skin color. With the use of a fusion composition, either injected below the surface of the skin or spread on the surface of the skin where hair removal is desired, allows for selective thermal damage.

There are other cosmetically unappealing situations that would benefit from the use of the instant invention. Skin resurfacing, for wrinkles, acne, scar revision, inter alia, typically involves chemicals, pneumatic crystals or laser radiant energy, which ablate the top layers of skin. This removes hypertrophic and hypotrophic structures, causes collagen melting and induces a cascade of healing events and new tissue generation that eventually lead to the desirable cosmetic endpoint. In laser-assisted tattoo removal, darkening of the skin often occurs, which is a consequence of the laser-induced conversion of ferric oxide to ferrous oxide in the tattoo ink resulting in an insoluble black pigmentation within the skin. Furthermore, allergic reactions sometimes occur with laser treatment of tattoos purportedly caused by altered antigenicity of the tattoo pigment by the laser light energy.

As described below, the invention provides a number of therapeutic advantages and uses, however such advantages and uses are not limited by such description. Embodiments of the present invention are better illustrated with reference to the FIGS. 1-21, however, such reference is not meant to limit the present invention in any fashion. The embodiments and variations described in detail herein are to be interpreted by the appended claims and equivalents thereof.

FIG. 1 depicts a length of surgical suture 10 having a cylindrical shape with a first end 12 and a second end 14. The surgical suture 10 is composed of a filamentous material and a metal (not shown) either distributed through the suture material or minimally present at the site of fixation. The first and second ends 12,14 are juxtaposed to one another in opposite directions such that the ends 12,14 form a weld upon activation.

Figure 2:
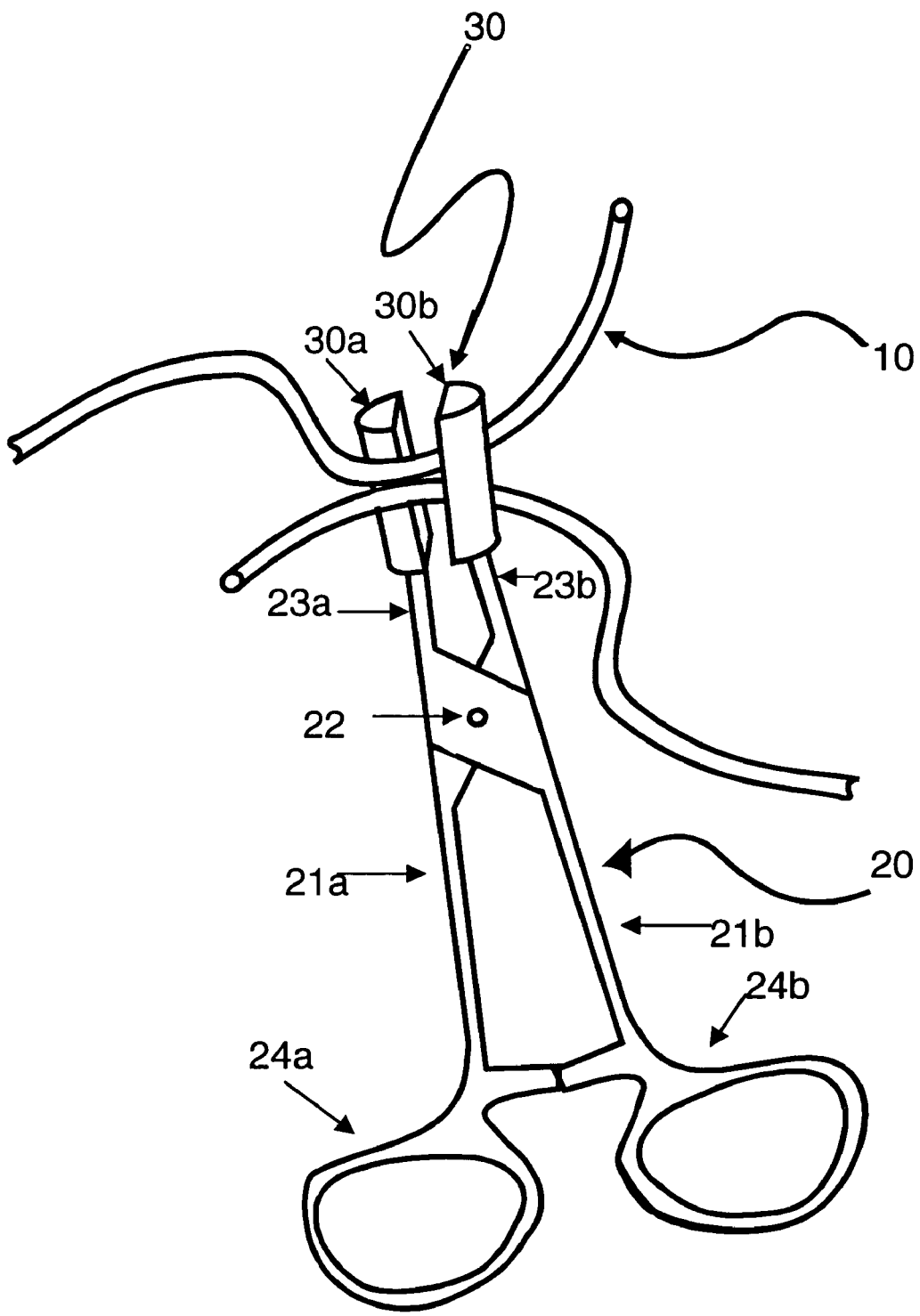
FIG. 2 depicts surgical suture composed of filamentous material and handheld applicator to effect a weld in the suture along the lengths of suture in contact with one another.

Continuing to refer to FIG. 1, FIG. 2 depicts a forceps-like surgical suture applicator 20. The suture applicator 20 comprises a scissors-like extension having two arms 21a,b pivotally connected at the center 22. The arms 21a,b have a first end 23a,b with elements 30a,b that transfers energy to two lengths of suture to be fixed 10 clamped therebetween and have a second end 24a,b comprising a gripping means. The elements 30a,b have an essentially planar inner surface and linearly extend from the first ends 23a,b such that the planar inner surfaces are juxtaposed in parallel relation when the applicator 20 is clamped. The pivotal action of the arms 21a,b increases or decreases the distance between the inner surfaces of the elements 30a,b such that the suture 10 may be positioned at a surgical site. The elements 30a,b are connected to an energy source (not shown).

Figure 3:
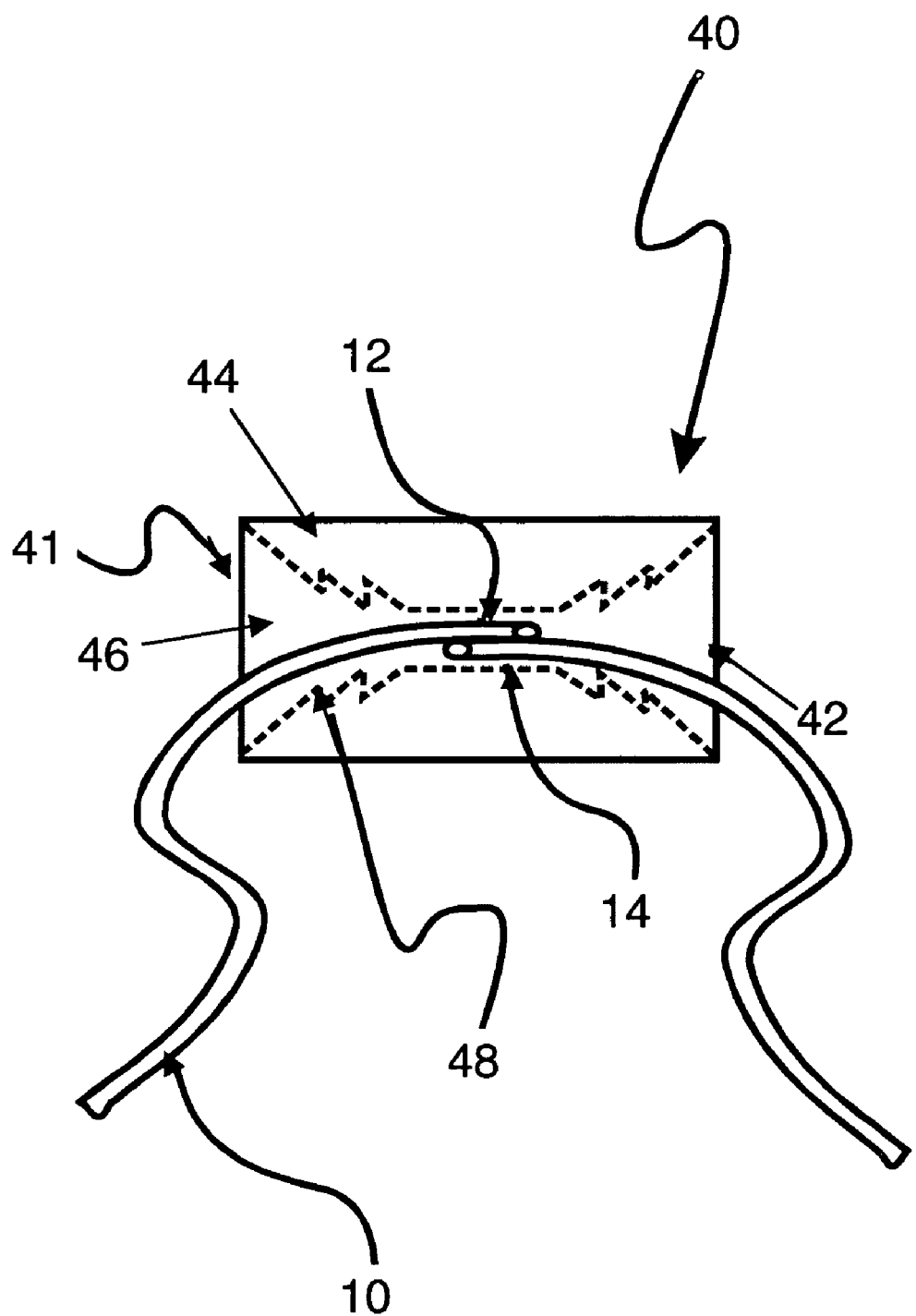
FIG. 3 depicts a cross-sectional view of an applicator that may be used to hold the ends of a single suture, or two connecting suture ends, in proximity to one another while inductively heating the material of the suture or applicator.

Continuing to refer to FIG. 1, FIG. 3 depicts a suture 10 having ends 12,14 that can be positioned within an applicator 40. The applicator 40 has a first end 41 and a second end 42 parallel to the first end 41 and a channel 46 on a surface 44 of the applicator 40 connecting the ends 41,42. A series of ridges 48 are disposed along the interior of the channel 46 such that the width of the channel 46 at the ends 12,14 is greater than the width of the channel 46 in the center of the applicator 40. The ends 12,14 of the suture 10 are inserted into the ends 41,42 of the applicator 40 until the ends 12,14 of the suture 10 overlap in the center of the channel 46. The ridges 48 hold the suture 10 taut while exposing the ends 12, 14 to applied energy. The applicator may be composed of two parts, separated by the channel 46, such that the applicator may be removed following fixation.

Figure 4:
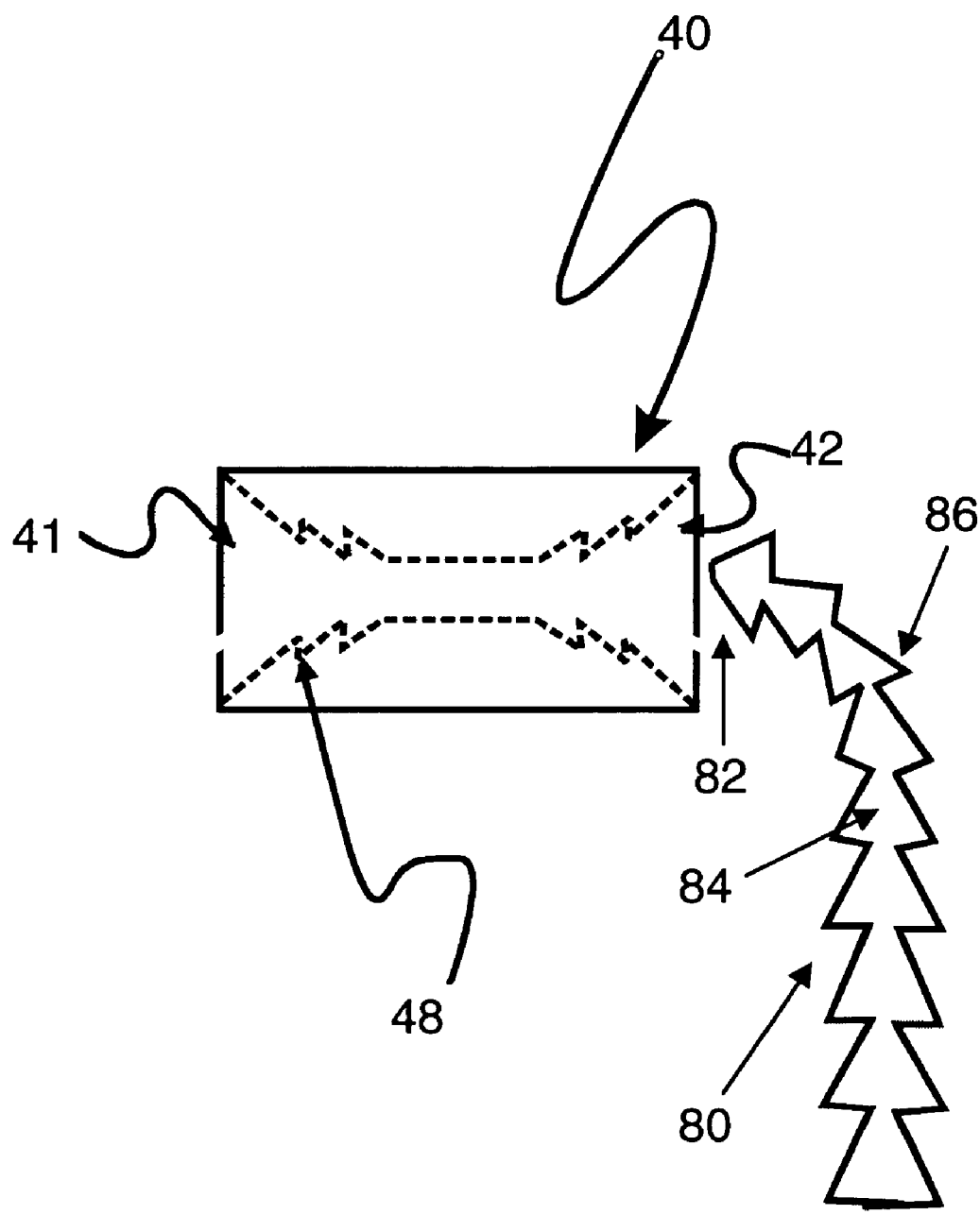
FIG. 4 depicts a cross-sectional view of the applicator of FIG. 3 to hold a ridged suture material inserted into the element in place. A second ridged suture, or the end of the same suture is placed in the other end.

Continuing to refer to FIG. 3, FIG. 4 depicts a suture 80 inserted into the applicator 40. The suture 80 has a substantially pointed first end 82 and an outer surface 84 with a plurality of ridges 86 evenly distributed down the length of the suture 80. The first end 82 is inserted into one of the ends 41,42 of the applicator 40. The combination of the ridges 86 on the suture 80 and the ridges 48 on the applicator 40 holds the suture 80 in place. The applicator may be composed of two parts, separated by the channel, such that the applicator may be removed following fixation.

Figure 5:
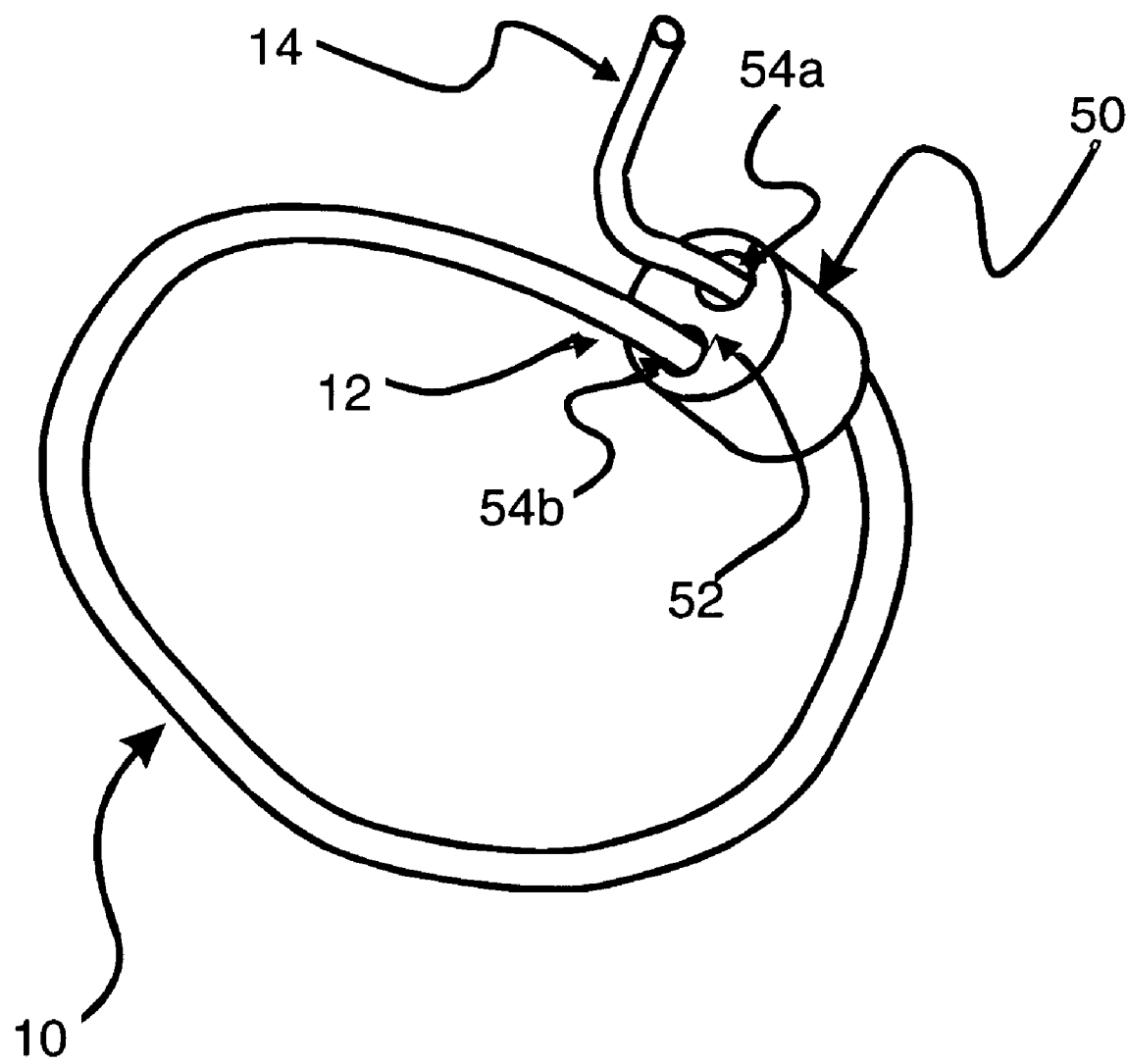
FIG. 5 depicts an applicator that may be used to inductively heat the suture.

Continuing to refer to FIG. 1, FIG. 5 depicts an applicator 50 that holds the two ends 12,14 of a suture 10 in place while the applicator 50 is exposed to a magnetic field generated by an induction coil (not shown). The applicator 50 is cylindrical in shape with a first face 52 and a second face (not shown) parallel thereto. The first face 52 comprises two circular openings 54a,b positioned equidistant along a diameter thereof and the second face comprises a circular opening positioned as is opening 54a. An end 12 of a suture 10 is inserted into the applicator 50 via the opening 54a, exits the applicator 50 via the opening on the second face and is looped around to be inserted into opening 54b. The end 14 of the suture 10 is exterior to the applicator 50. This juxtaposes a selected two segments of the suture within the applicator. Application of a magnetic field to the applicator 50 effects a weld. The applicator may be composed of two parts, separated across the two circular openings 54a,b, such that the applicator may be removed following fixation.

Figure 6:
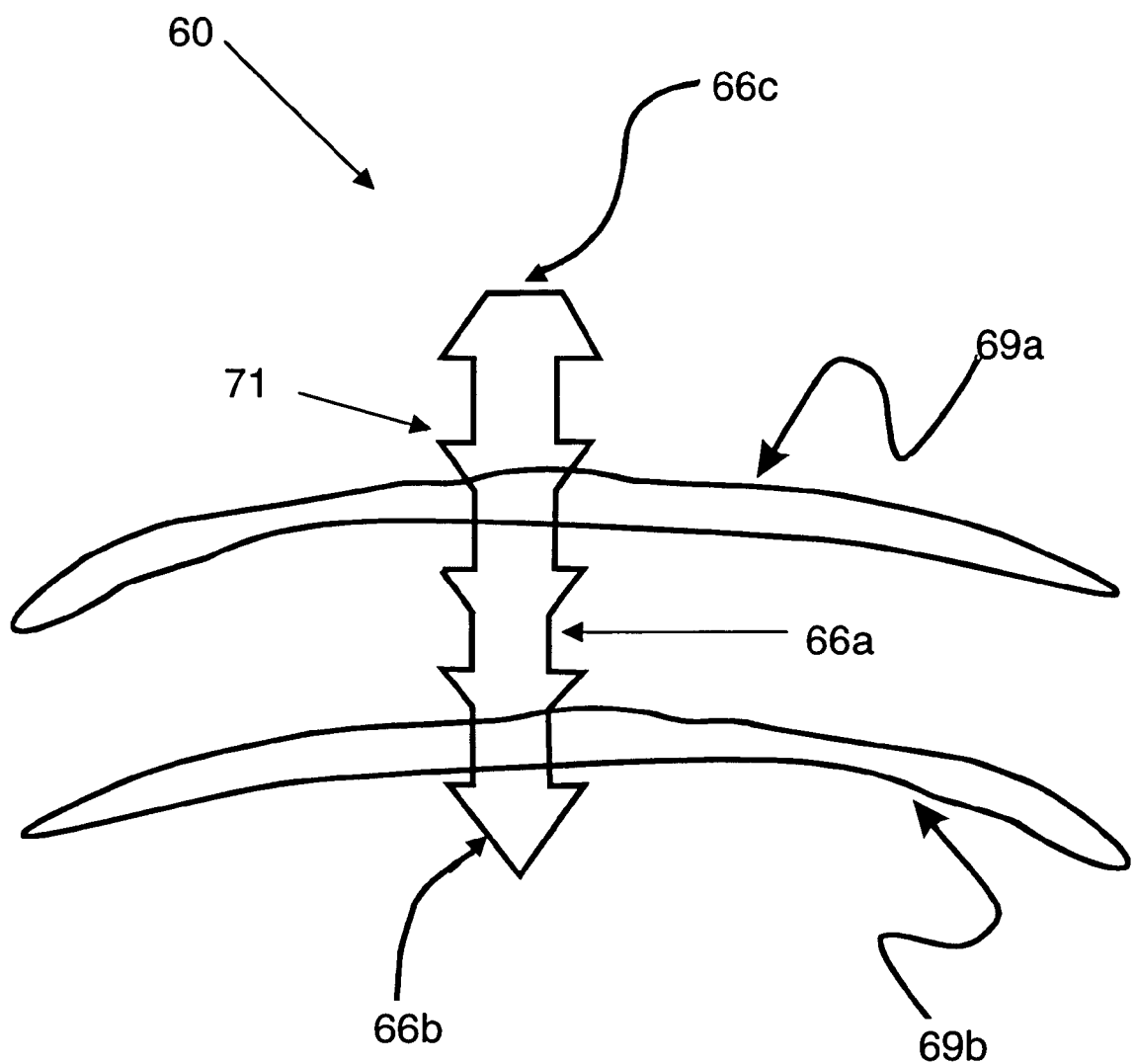
FIG. 6 depicts a surgical pin for placement between two sections of overlapping tissue.

FIG. 6 depicts a surgical pin 60, composed at least in part of a fusion composition material, having a straight pin body 66a with a first pointed end 66b and a second truncated end 66c opposite the first end 66a. The first pointed end 66a on the surgical pin 60 provides ease of insertion into two overlapping sections of tissue 69a,b and anchors the surgical pin 60 at the outer surface of tissue segment 69b. The second truncated end 66c prevents the surgical pin 60 from completely piercing through the outer surface of tissue segment 69a upon pinning the overlapping tissue segments 69a,b together and anchors the surgical pin 60 to the outer surface of the tissue segment 69a. The pin body 66a has a plurality of spines 71 along the outer surface of the pin body 66a that provide friction or a temporary anchoring mechanism for placement between the two sections of overlapping tissue 66a,b.

Figure 7:
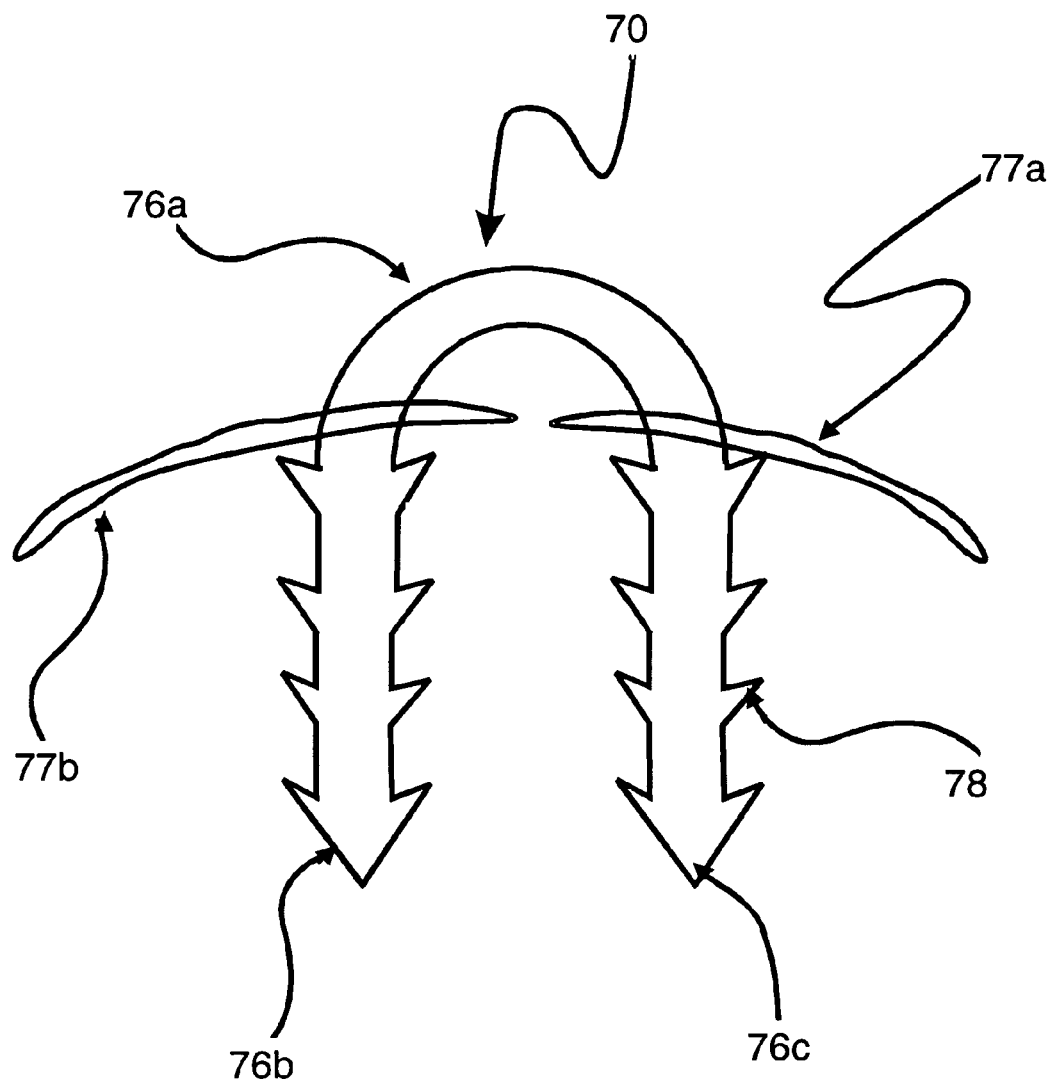
FIG. 7 depicts a surgical staple to fasten tissue that has been separated.

With reference to FIG. 6, FIG. 7 depicts a surgical staple 70, composed at least in part of a fusion composition material, having a symmetrically curved body 76a with pointed first and second ends 76b,c which is used to fasten tissues 77a,b which have been separated surgically or as the result of a wound. The surgical staple 70 has a plurality of spines 78 along the outer surface of the first and second ends 76b,c of the staple 70 that provide an anchoring mechanism for placement across the wound in the tissue 77a,b.

Figure 8A:
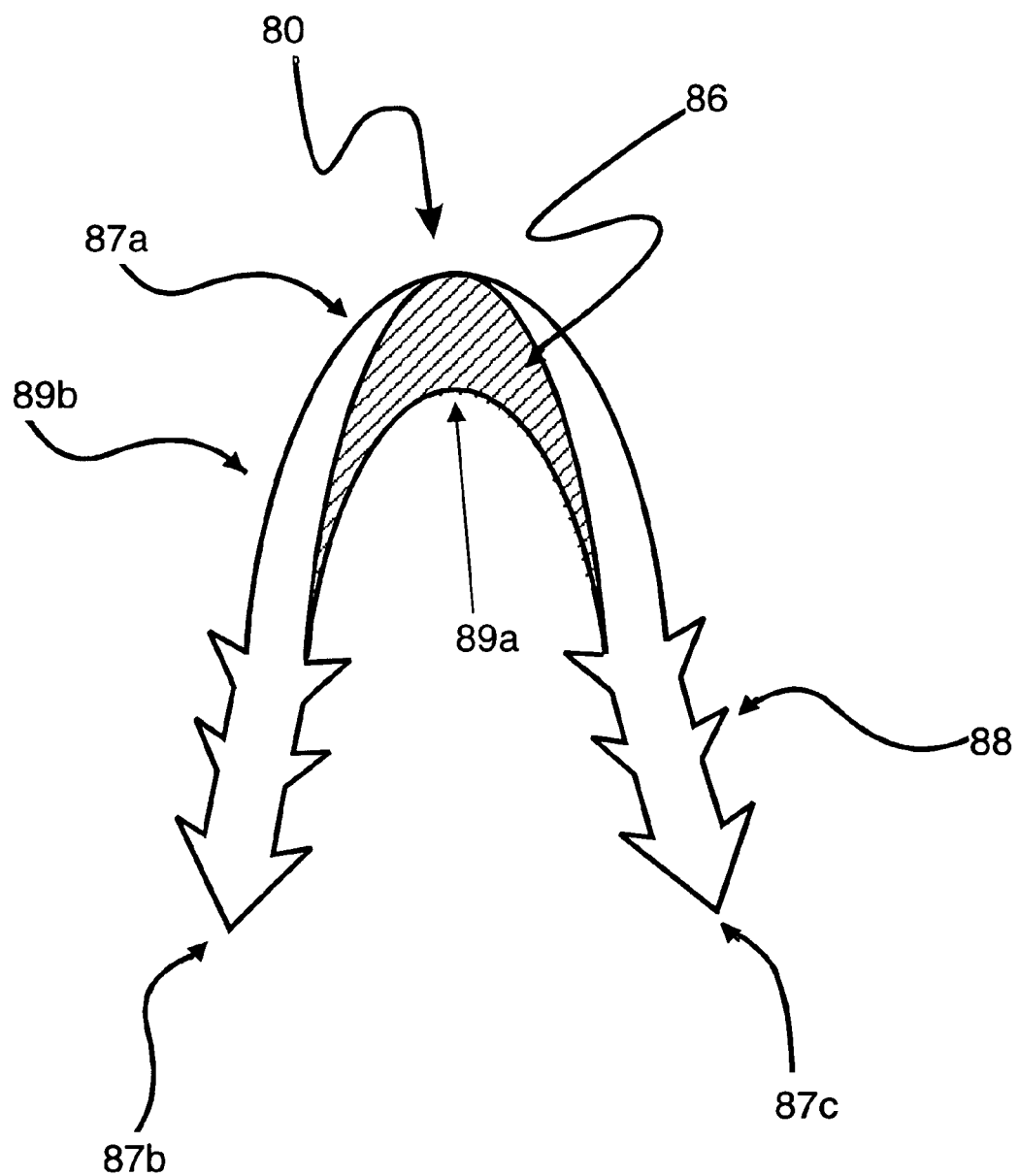
FIG. 8A depicts a surgical compression staple.
Figure 8B:
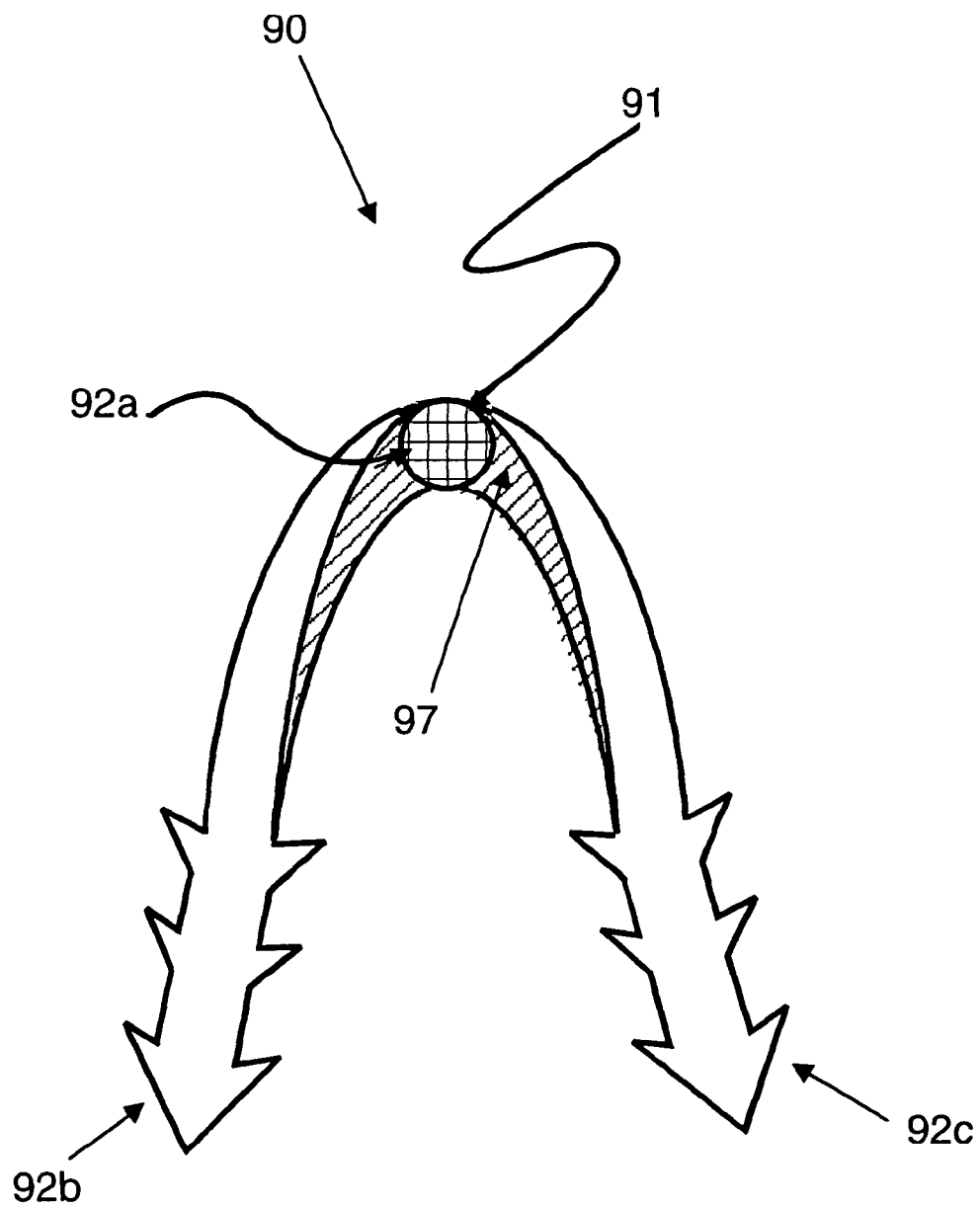
FIG. 8B depicts a multi-piece surgical compression staple.

With reference to FIG. 7, FIGS. 8A and 8B depict embodiments of a surgical compression staple 80. In FIG. 8A the compression staple is a single piece composed at least in part of a fusion composition material, having a symmetrically curved body 87a with pointed first and second ends 87b,c and having a plurality of spines 88 along the outer surface of the first and second ends 87b,c of the staple 80 as in FIG. 7. The middle curved segment 87a of the compression staple 80 is comprised of an inner sleeve 86 of a flexible elastic polymer whereby the inner surface 89a of compression staple 80 is capable of greater shrinkage than the external surface 89b.

With reference to FIG. 8A, FIG. 8B depicts a variation thereof. FIG. 8A shows a multi-piece surgical compression staple further having a hinge 91 at the middle section 92a of the compression staple 90. Compression is effected by the hinging action on the two segments 92b,c of the compression staple 90 and by the inner sleeve of flexible elastic polymer 97 as in FIG. 8A.

Figure 9:
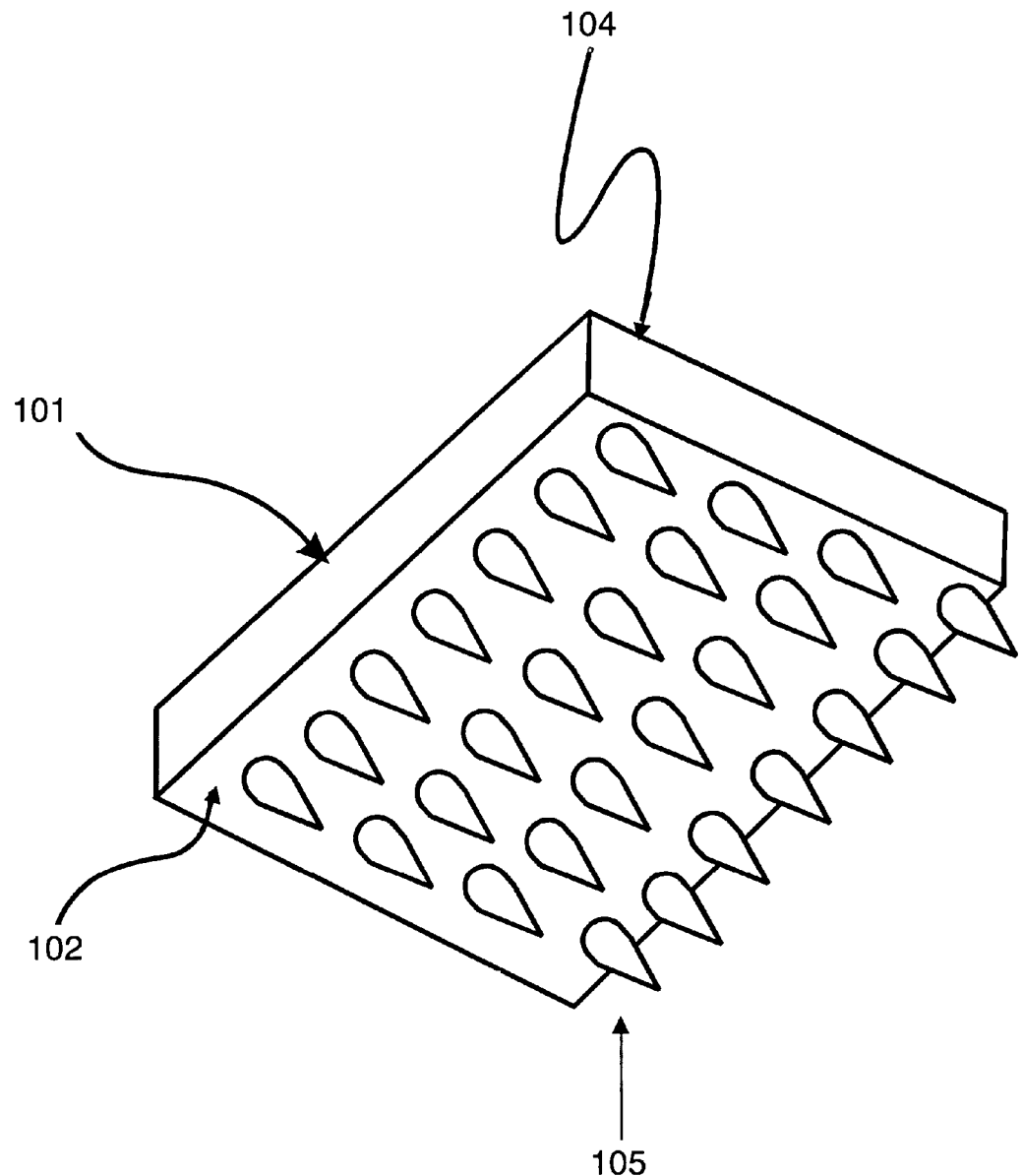
FIG. 9 depicts a tissue-fastening device with a single layer of material having angular spines on one surface only.

FIG. 9 depicts a tissue-fastening device 104, composed at least in part of a fusion composition material, having an outer surface 101 and inner surface 102. The inner surface 102 has a plurality of spines 105 disposed thereon and protruding from the inner surface 102 of the device 104 in a substantially perpendicular direction.

Figure 10:
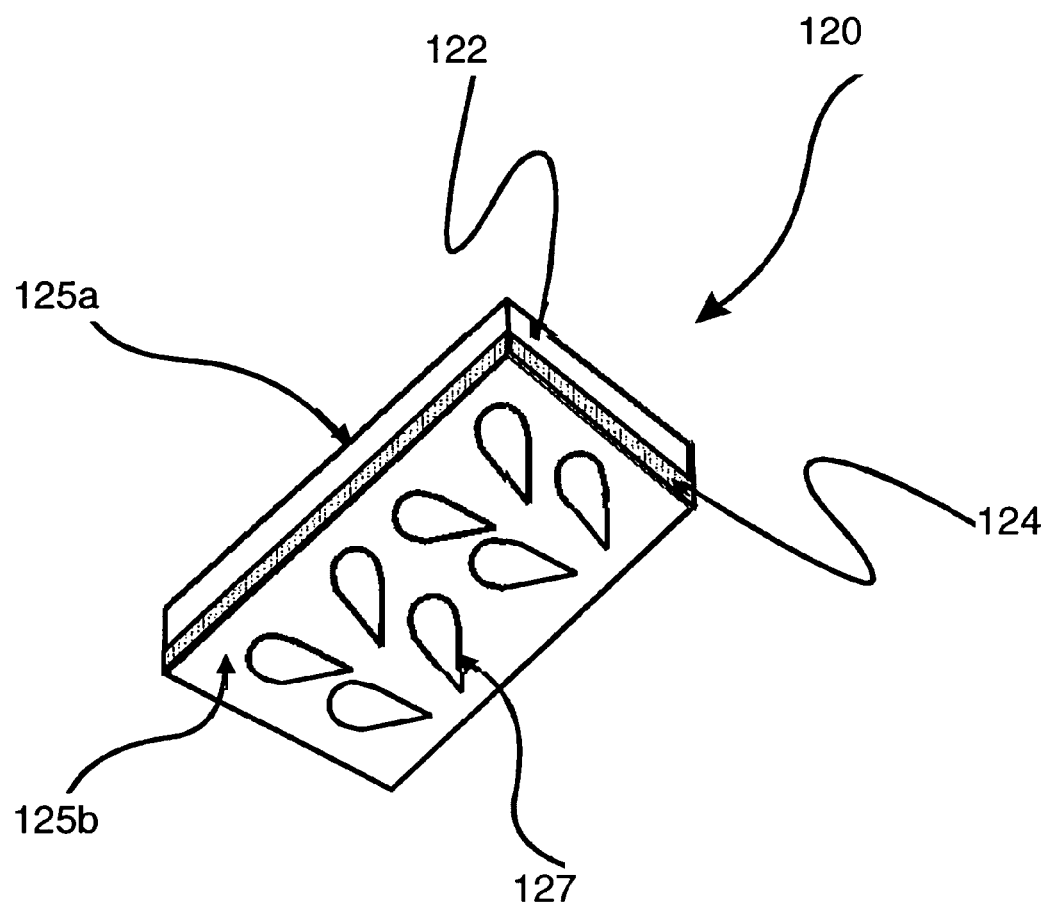
FIG. 10 depicts a compression style tissue-fastening device, with multiple layers of material with different shape conforming qualities having angular spines along an inner surface.

FIG. 10 depicts a compression style tissue-fastening device 120, composed at least in part of a fusion composition material, with layers 122,124 disposed one on the other having an outer surface 125a on outer layer 122 and inner surface 125b on inner layer 124. Layers 122, 124 may have different shape conforming qualities. The inner surface 125b has a plurality of angular spines 127 disposed thereon and protruding from inner surface 125b of inner layer 124 at varied angles.

Figure 11:
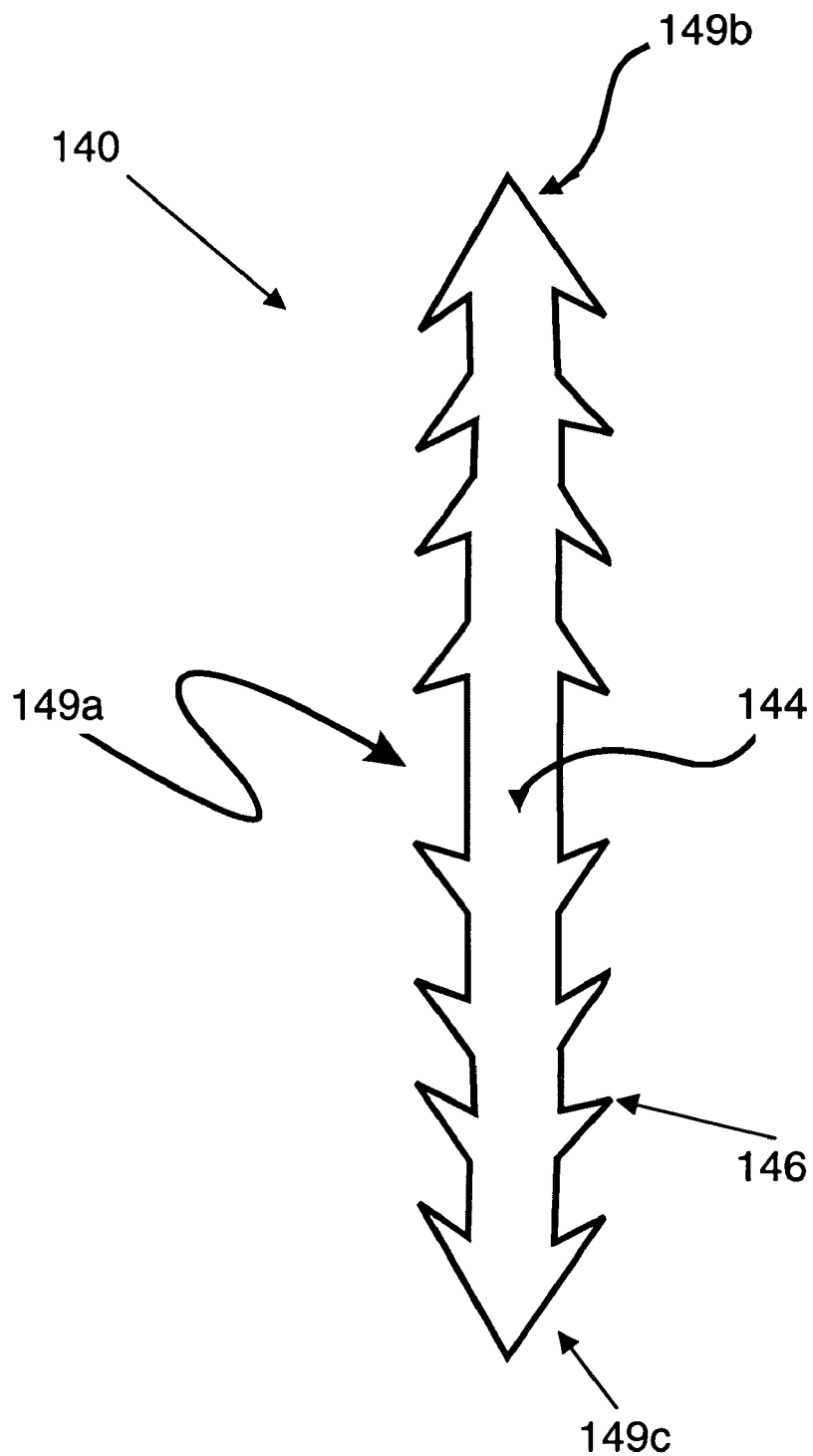
FIG. 11 depicts a two-sided compression style tissue-fastening device composed partly of a conductive, shrinkable material and having angular spines along an inner surface.

With reference to FIG. 6, FIG. 11 is a two-sided compression style tissue-fastening device 140, composed of a conductive, shrinkable material 144 and a fusion composition material, having a straight body 149a with a first pointed end 149b and a second pointed end 149c opposite the first end 219b. The device 140 has a plurality of angular spines 146 along the outer surface of the first and second ends 149b,c. One of each of the first or second ends 149b,c is placed and anchored in and between one of two sections of overlapping tissue (not shown). Shrinking the material 144 in combination with the spines 146 fastens and anchors the tissue sections together.

Figure 12:
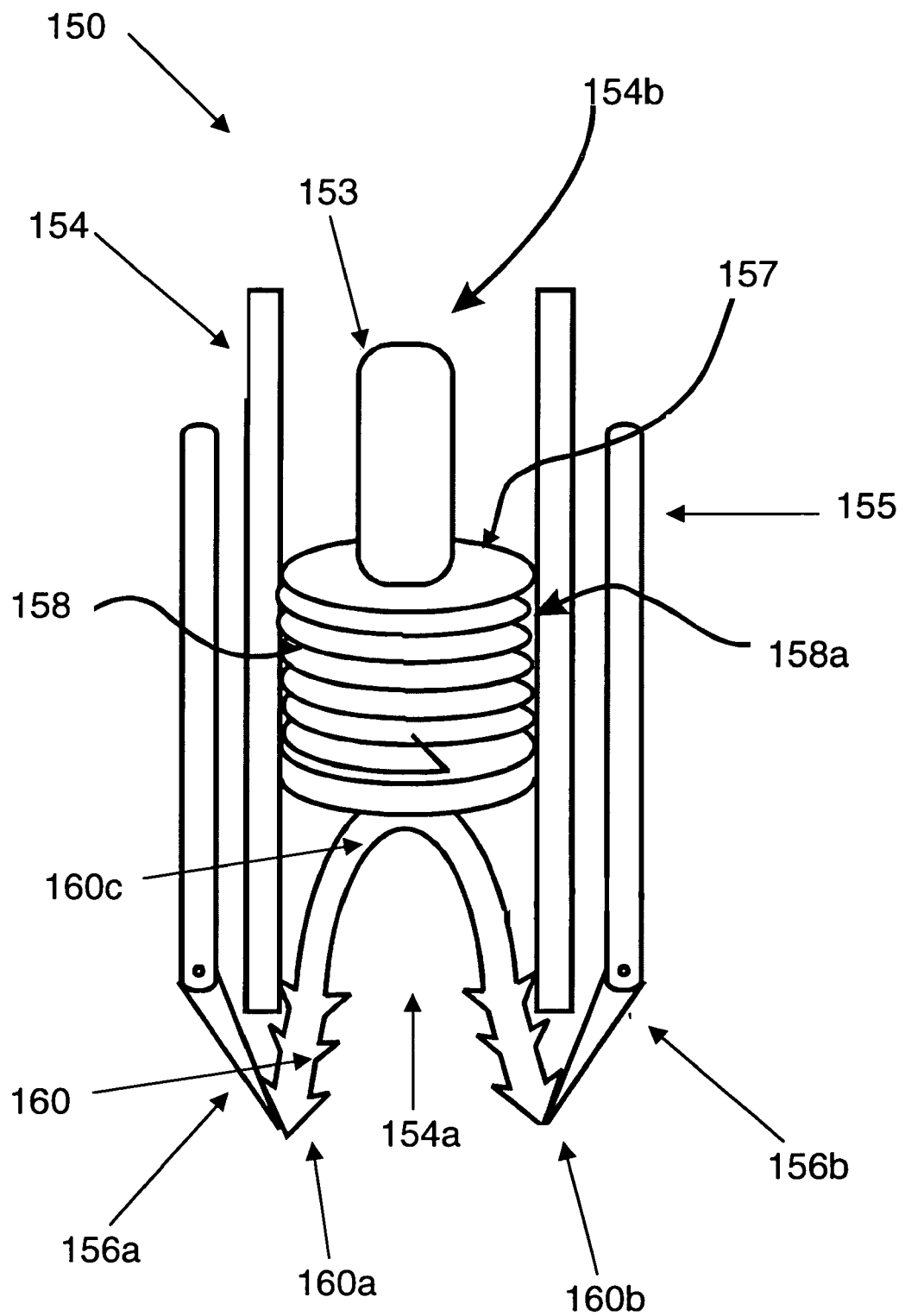
FIG. 12 depicts an applicator for delivering tissue-fastening devices.

FIG. 12 depicts an applicator for fasteners 150. The applicator has an inner sleeve 154 with a first 154a open end and a second open end 154b and a retractable outer sleeve 155 with hinged restrainers 156a,b at a first open end 154a. The fastener 152 is positioned within the first open end 154a of the inner sleeve 154 such that the first end 160a and the second end 160b of the fastener 160 rest against the hinged restrainers 156a,b and the curved middle section 160c of the fastener 160 is positioned against the lower end 158b of a spring mechanism 15 disposed within the inner sleeve 154. A plunger 153 applies pressure to the upper end 158a of the spring mechanism 328 which positions the fastener 160 through force applied to a disk 157 at the upper end 158a of the spring mechanism 158. The action of the force on the disk 157 compresses the spring mechanism 158 and transfers the downwardly applied force to the fastener 160. The first and second ends 160a,b of the fastener 160 simultaneously are forced past the hinged restrainers 156a,b and can thus be positioned within at least one tissue (not shown).

Figure 13A:
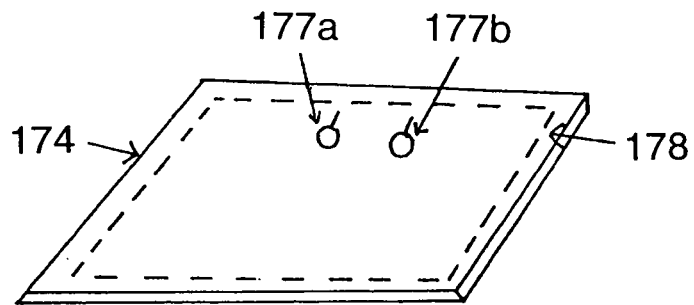
FIG. 13A depicts the placement of exposed terminals attached to an electrical conducting element within a material which is altered upon the application of electromagnetic energy.

FIG. 13A shows a material 174 which may be a semi-solid matrix incorporating a conducting element 178. The conducting element terminates at exposed terminals 177a,b. The terminals 177a,b may couple the conducting element 178 to a current source or high frequency voltage source (not shown).

Figure 13B:
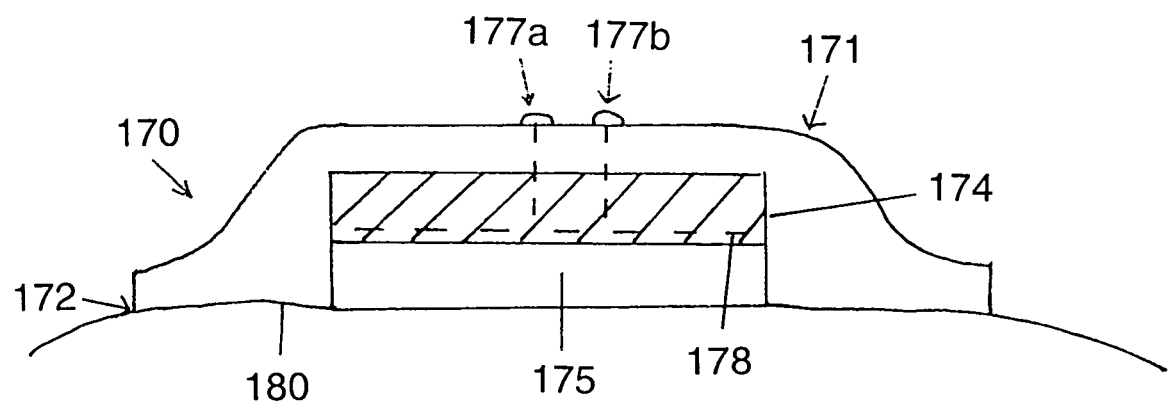
FIG. 13B is a cross-sectional schematic of a patch that is placed on the skin of an individual; the patch contains the electrical conducting element and a semi-permeable material.
Figure 14A:
FIG. 14 depicts the electrical conducting element with a linear geometry (FIG. 14A), with a coiled geometry (FIG. 14B) or consisting of small three-dimensional conducting nodes connected by fine linear elements (FIG. 14C).
Figure 14B:
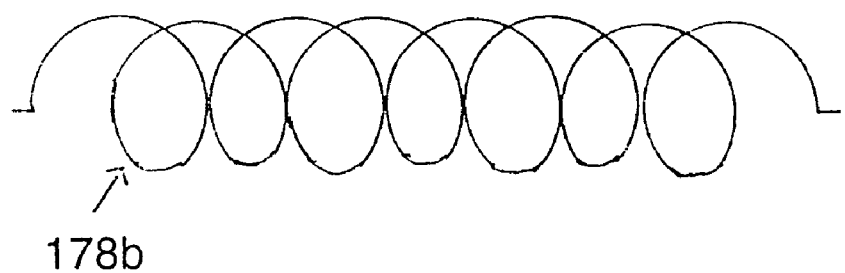
Figure 14C:

In FIG. 13B the material 174 containing the conducting element 178 is incorporated into a patch 170. The patch 170 has an upper surface 171 on which the terminals 177a,b are located and a lower surface 172 which contacts the surface of the skin 180. The patch may optionally have an adhesive (not shown) for temporary adherence to the tissue. The material 174 containing the conducting element 178 is contained within the patch 170 and placed in contact with a fusion composition 175 within the patch 170 which is in contact with the skin 180 such that the fusion composition 30 is sandwiched between the material 174 and the skin 180.

With reference to FIGS. 13A and 13B, FIGS. 14A, 14B and 14C depict possible geometries of the conducting element 178. The conducting element 178 may be linear 178a, coiled 178b or consist of small conducting nodes which are connected by fine linear elements 178c. It is to be noted that reference to conducting element 178 includes, but is not limited to, geometries 178a, 178b and 178c of the conducting element 178 unless specifically indicated otherwise.

Figures 15A, 15B:
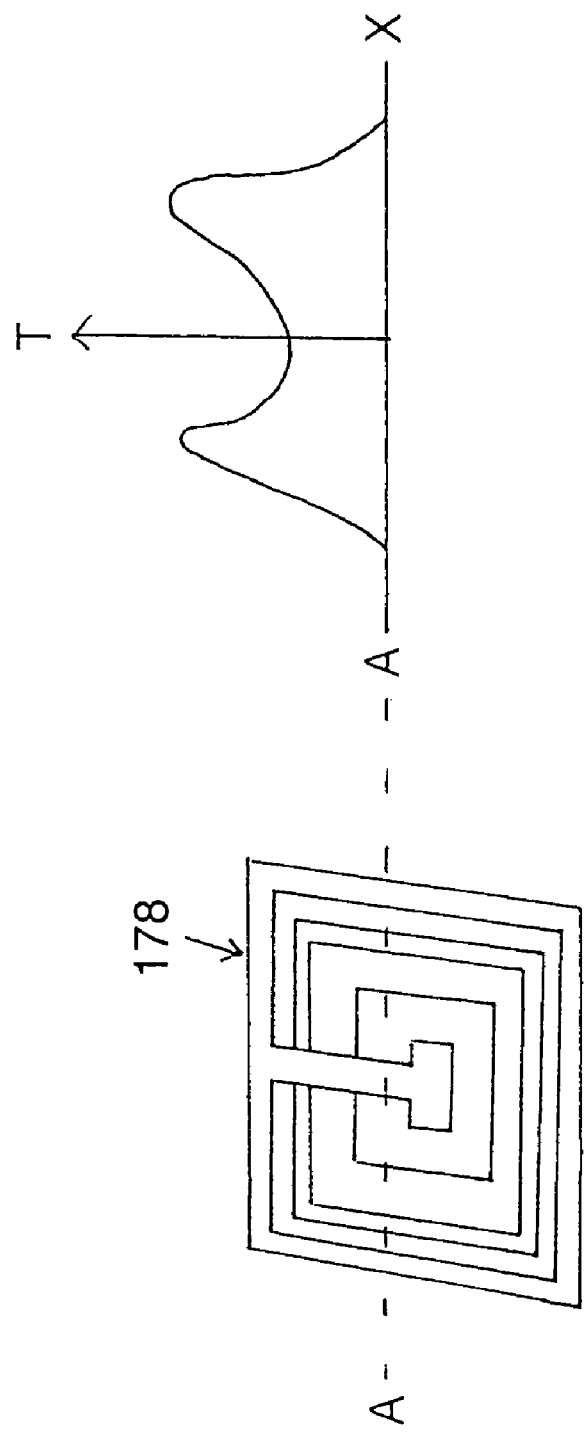
FIG. 15A depicts a particular geometry of the electrical conducting element within a patch that is conducive to non-uniform heating.
FIG. 15B illustrates the theoretical temperature profile across the cross-section A-A of the patch in FIG. 15A.

FIG. 15A depicts an arrangement of the conducting element 178 in a particular geometry that results in a non-uniform heating and, thereby, weld across the area of the conducting element 178. FIG. 15B illustrates a theoretical temperature profile across a cross-section A-A of the patch 170 showing the non-uniformity of the temperature.

Figure 16A:
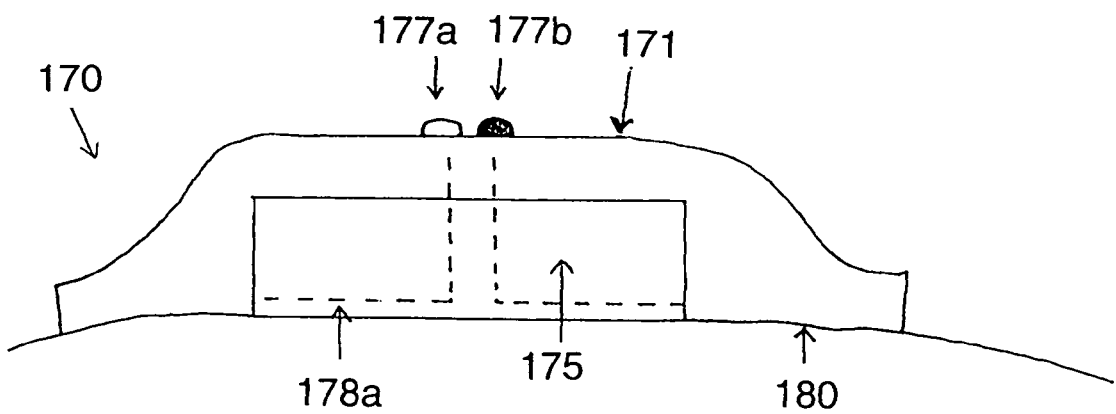
FIG. 16A shows the conducting element positioned within a fusion composition in close proximity to the surface of the skin.

Still with reference to FIG. 13B, FIGS. 16A-16C depict a patch 170 having the conducting element 178 within the fusion composition 175 with various means of conductively or inductively heating the conducting element 178. In FIG. 16A a patch 170 comprises a fusion composition 175 placed within the patch 170 such that the patch 170 and the fusion composition 175 are in contact with the skin 180. The conducting element 178a is positioned within the fusion composition 175 to be in close proximity to the surface of the skin 180. The conducting element 178a terminates at exposed terminals 177a,b located on the outer surface 171 of the patch 170. The terminals 177a,b may be coupled to a current source or high frequency voltage source (not shown) as in FIG. 13B.

Figure 16B:
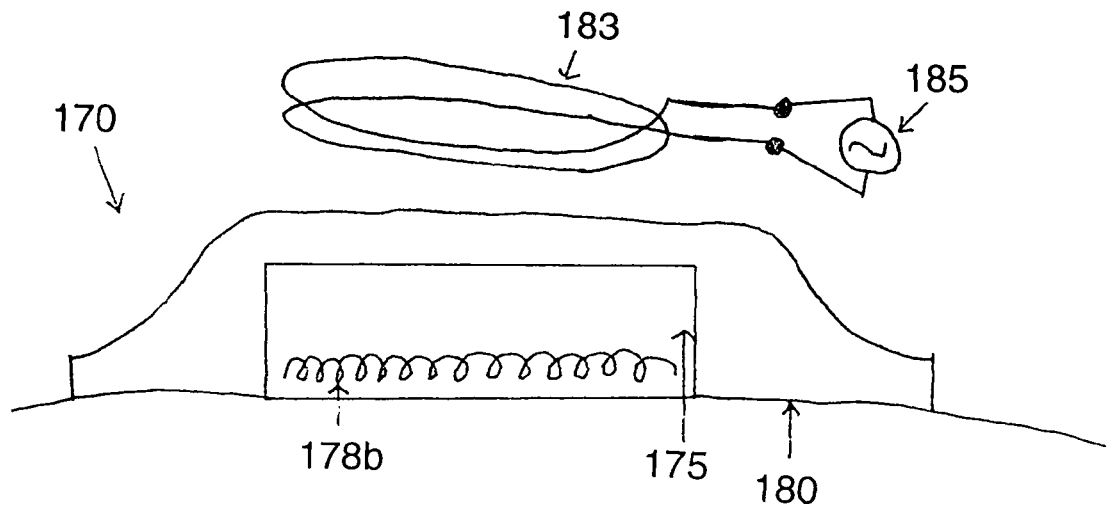
FIG. 16B shows the conducting element within a fusion composition in a coiled configuration to efficiently inductively absorb ambient radiofrequency energy produced by a coil attached to a radiofrequency power-source.

In FIG. 16B the fusion composition 175 contains conducting element 178b located proximally to the surface of the skin 180. The conducting element 178b inductively absorbs ambient radiofrequency energy generated by a coil 183. The coil 183 is external to the patch 170 and superimposed proximally to the upper surface 171 of the patch 170. The coil is attached to a radiofrequency power source 185.

Figure 16C:
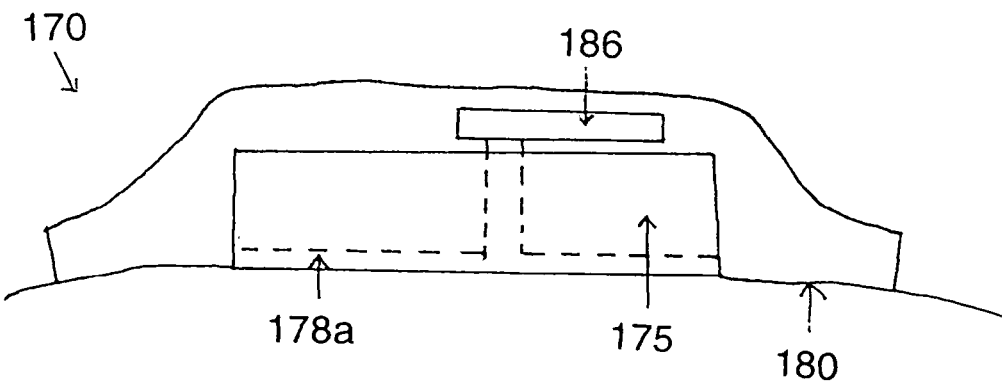
FIG. 16C depicts the conducting element within a fusion composition connected to a battery that is also incorporated into the patch.

FIG. 16C depicts a patch 170 with fusion composition 175 having a conducting element 178a as in FIG. 16A. The conducting element 178a terminates in a battery 186 incorporated into the patch 170 but external to and superimposed proximally to the fusion composition 175.

Figure 17:
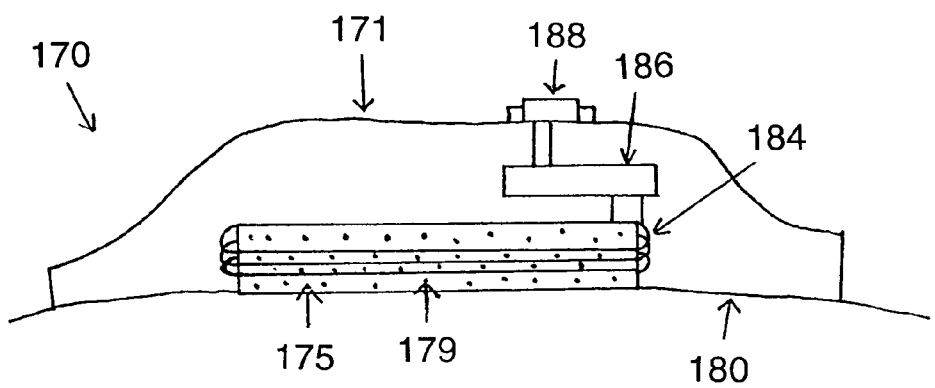
FIG. 17 depicts a cross-sectional view of the patch showing that the fusion composition contains small conducting absorbers and an inductive coil around the fusion composition; the coil is powered by a battery regulated by an external switch.

With continued reference to FIGS. 13B and 16C, FIG. 17 depicts a patch 170 comprising a fusion composition 175, placed proximate to the surface of the skin as in FIG. 16C, containing small conducting absorbing elements 179. The absorbing elements 179 are inductively heated by radiofrequency energy supplied to a coil 184 emplaced around the fusion composition 175. The battery 186 powers circuitry (not shown) that delivers the radiofrequency energy to the coil 184 and is modulated via a switch 188 connected to the battery 186. The switch 188 is located on the upper surface 171 of the patch 170.

Figure 18:
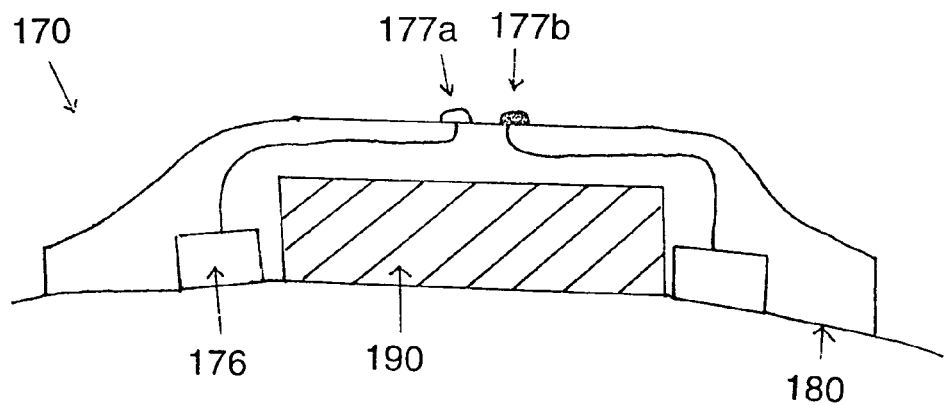
FIG. 18 depicts a patch with an annulus for the weld connected to the terminals where a material or a medicament is contained within the annulus.

FIG. 18 depicts a patch 170 comprising an annulus 176 in contact with the surface of the skin 180 and which is connected to terminals 177a,b. Emplaced within the area circumscribed by the annulus 176 is a material or medicament 190 in contact with the surface of the skin 180.

Figure 19A:
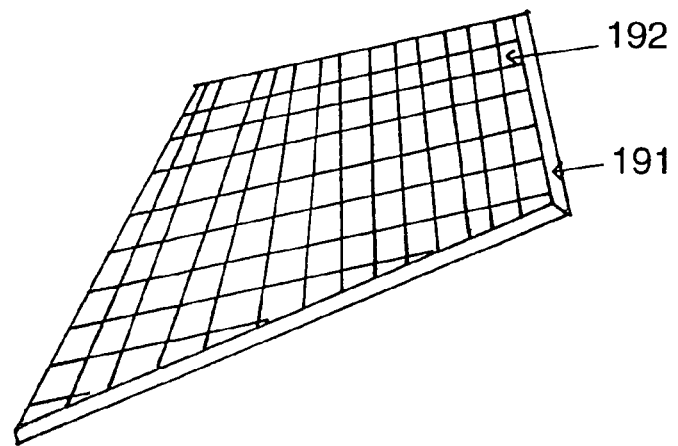
FIG. 19A depicts an arbitrarily shaped fusion composition containing an array of fine conducting elements.
Figure 19B:
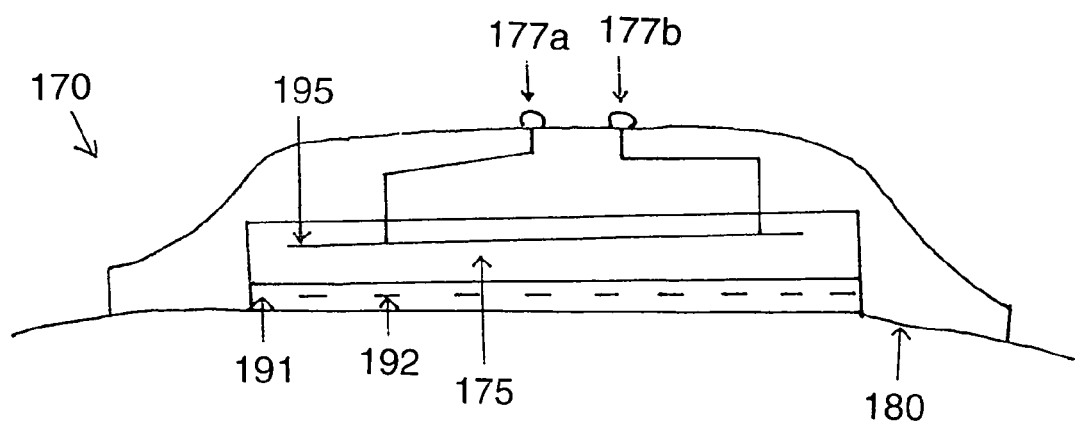
FIG. 19B depicts the placement of the array-containing fusion composition within the patch; a second part of the patch placed over the fusion composition contains conducting elements to heat the solder conductively or inductively.

FIG. 19A depicts a fusion composition 191 having an arbitrary shape and capable of being cut with scissors or other sharp instrument. The fusion composition 191 incorporates an array of fine conducting/heat absorbing elements 192. As shown in FIG. 19B, the fusion composition 191, cut in a desired shape, is contained within the patch 170 and placed over a wound on the surface of the skin 180. Material 175 which may be composed of a semi-solid matrix connected to exposed terminals 177a,b at element 195 is placed over the fusion composition 191 and 195 is connected to exposed terminals 177a,b. The element 195 either conductively or inductively heats the fusion composition 191 via application of radiofrequency energy to terminals 177a,b which thus effects a weld at the skin 180.

Figure 20:
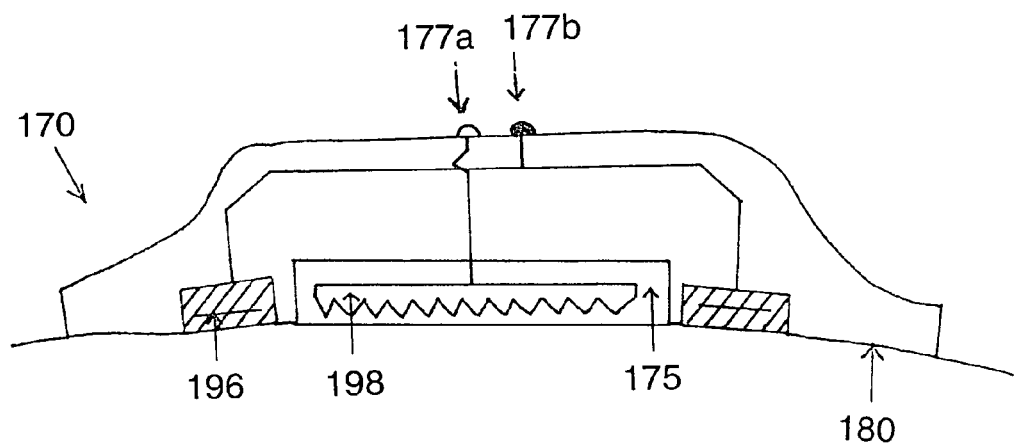
FIG. 20 depicts the fusion composition containing an array of microneedles to alter skin surface prior to welding the fusion composition and the tissue. The fusion composition is surrounded by an annular electrode which incorporates an electrically conductive fluid.

FIG. 20 depicts a patch 170 containing a fusion composition 175 placed on the skin 180. The fusion composition 175 contains an array of microneedles 198 proximate to the skin 180 which are connected to terminals 177a,b. An annular electrode 196 incorporating an electrically conductive fluid (not shown) also is connected to terminals 177a,b. Radiofrequency energy or a brief pulse or bipolar pulse of direct current through terminals 177a,b results in both tissue alterations of the skin 180 and thermal changes to the fusion composition 175.

Figure 21A:
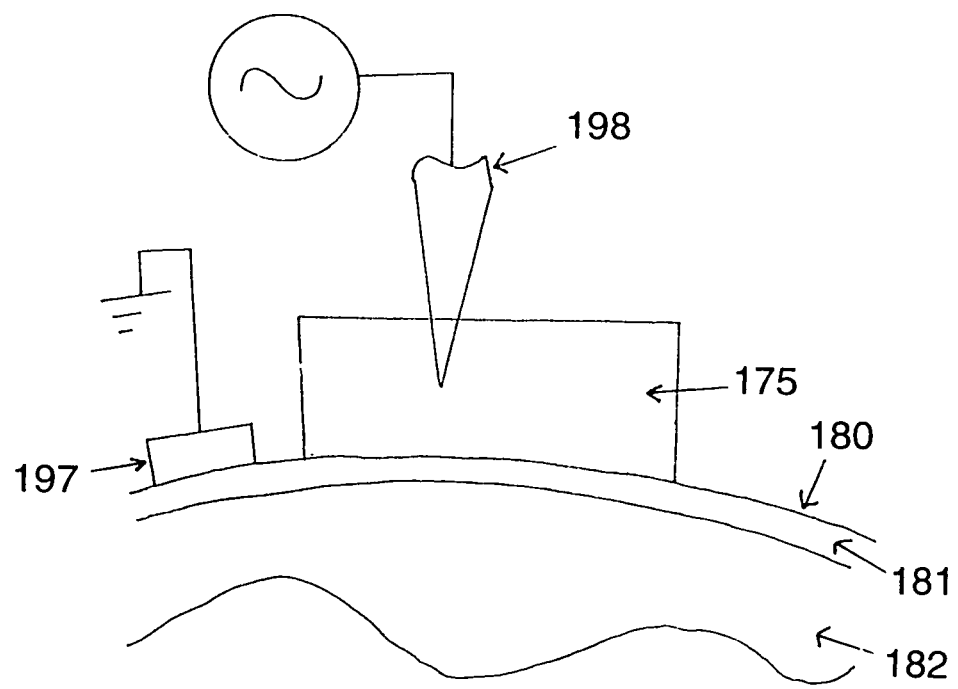
FIG. 21A depicts the positioning of an active electrode within the fusion composition and the ground electrode emplaced on the stratum corneum distal to the fusion composition.
Figure 21B:
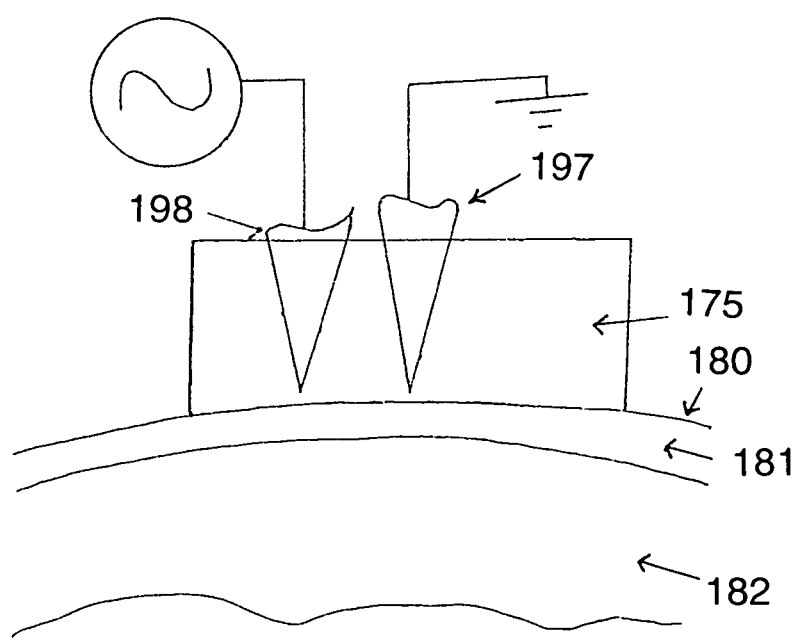
FIG. 21B depicts the positioning of both the active and ground electrodes within the fusion composition of FIG. 9A.

FIG. 21A depicts an active electrode 198 in contact with the fusion composition 175 which is placed on the stratum corneum 181 of the skin 180. A ground electrode 197 is located distal to the active electrode 198 and the fusion composition 175 and also is in contact with the stratum corneum 181. A plasma (not shown) forms, upon the application of radiofrequency energy or direct current, between the electrodes 197, 198 alters the stratum corneum without harming the epidermis 182 underneath the stratum corneum 181. Additionally, beneficial thermal changes are created within the fusion composition 180. Alternatively, FIG. 21B places both the active electrode 198 and the ground electrode 197 within the fusion composition 180.

Figure 22:
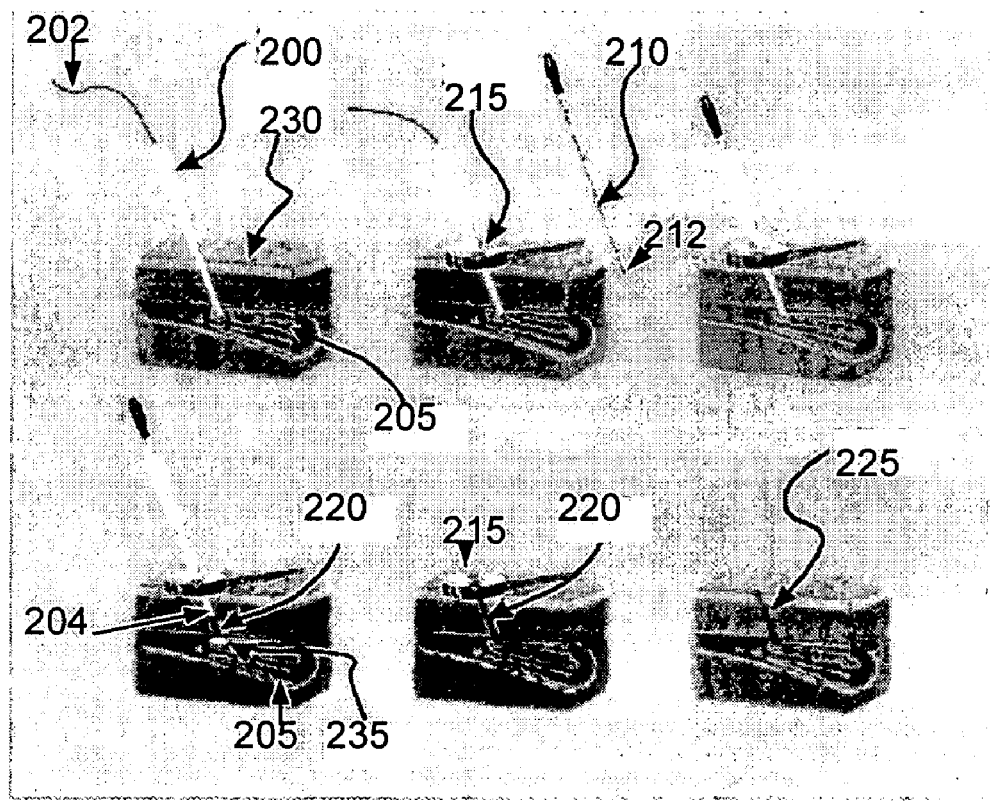
FIG. 22 depicts a device that can be used to produce sealing of a catheter vascular access tract.

FIG. 22 depicts an applicator and its method of use for closing a vascular access defect in tissue. A catheter introducer 200 is used to allow access to the lumen 205 of a blood vessel within a tissue 230. After the catheterization procedure and removal of the guidewire 202, a tissue-fusion applicator 215 is positioned in proximity to the introducer 200. A fusion composition delivery device 210 is placed within the lumen of the introducer 200.

A material 235 is located within the distal end 212 of the fusion composition delivery device. A small amount of material 235 is extruded out the distal end 204 of the introducer 200 with the delivery device 210 into the lumen 205 of the blood vessel to provide accurate positioning of the composition delivery device 210 and to temporarily occlude the vascular perforation. The material 235 is biocompatible and dissolves in the blood stream within minutes or hours of the procedure. Fusion composition 220 contained within the applicator 215 is delivered to the vascular access defect as the fusion composition delivery device 210 and the introducer 200 are withdrawn. The fusion composition 220 remaining in the defect is activated by the applicator 215 thus sealing the puncture 225 in the blood vessel and skin.

Figure 23:
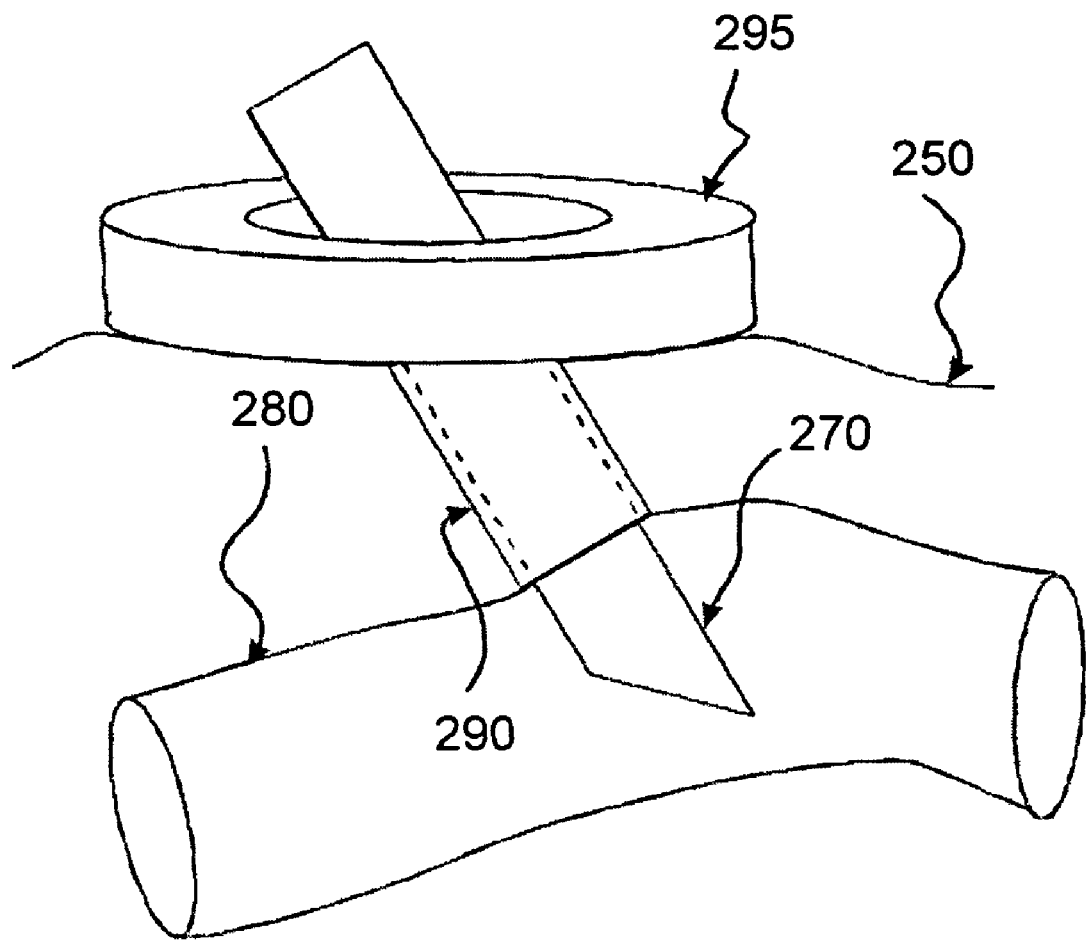
FIG. 23 depicts an applicator suitable for use in occluding cavities such as needle tracts.

FIG. 23 depicts an applicator suitable for closing a needle tract defect in tissue. A sheath 290 composed of fusion composition surrounds a needle 270 which is positioned within a blood vessel 280 within tissue 250 for the purpose of venipuncture. The tissue fusion applicator 295 is positioned close to the needle 270 and sheath 290. Upon withdrawal of the needle 270, the sheath 290 collapses, or is filled with fusion composition, and is activated with the fusion applicator 295 to substantially seal the needle tract.

Figure 24A:
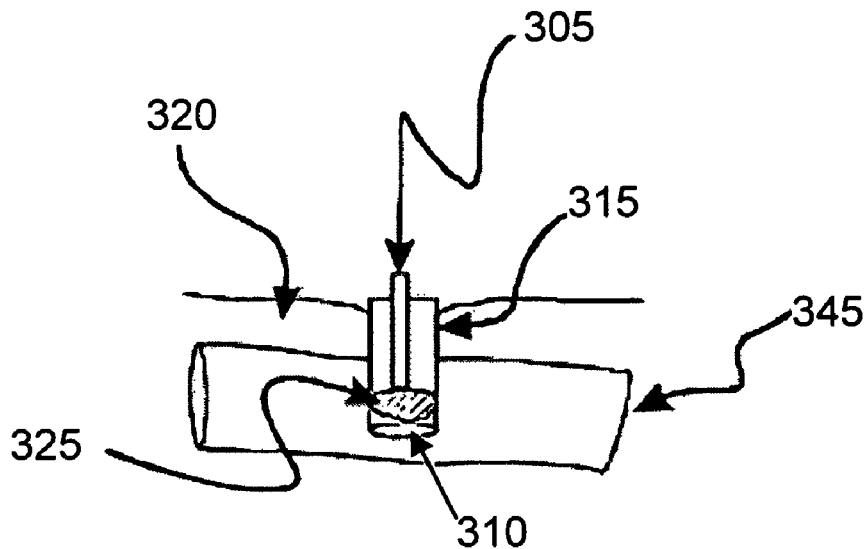
FIGS. 24A-D depict an applicator which positions an anchor for use within hollow anatomical structures such as blood vessels.
Figure 24B:
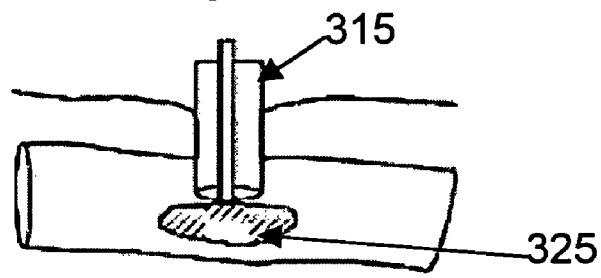
Figure 24C:
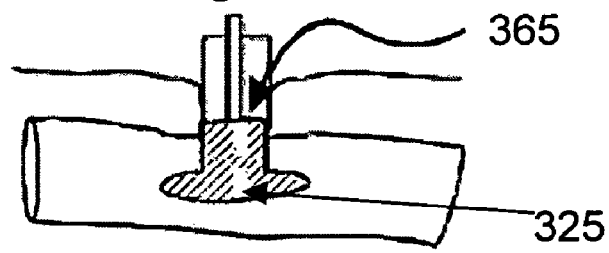
Figure 24D:
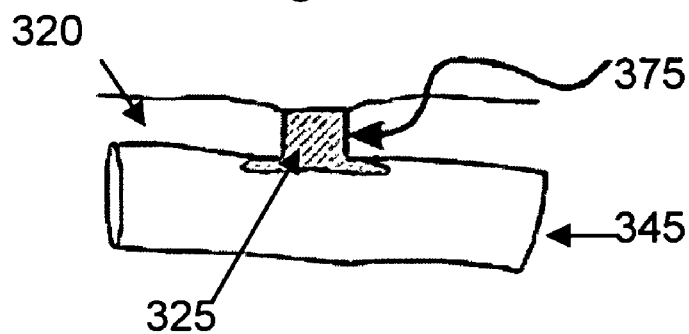

FIGS. 24A-24D depict an applicator suitable for closing a vascular access defect or other defect in tissue. In FIG. 24A an introducer 315 is positioned in the tissue 320 and perforates a vessel 345. Within the lumen of the introducer 315 is a plunger 305 and fusion composition 325. Here the fusion composition 325 swells upon contact with blood. In FIGS. 24B-C the fusion composition 325 is extruded out the end 310 of the introducer 315 whereupon it expands. In FIG. 24C, upon withdrawal of the introducer 315 and retraction of the plunger 305, the bond 365 between the fusion composition 325 and plunger 305 can be breached. In FIG. 24D the fusion composition 325 fills the vascular perforation in the vessel 345 and tissue defect in the tissue 320. If required, the fusion composition 325 can be activated with an externally positioned applicator such as shown in FIG. 23.

Figure 25A:
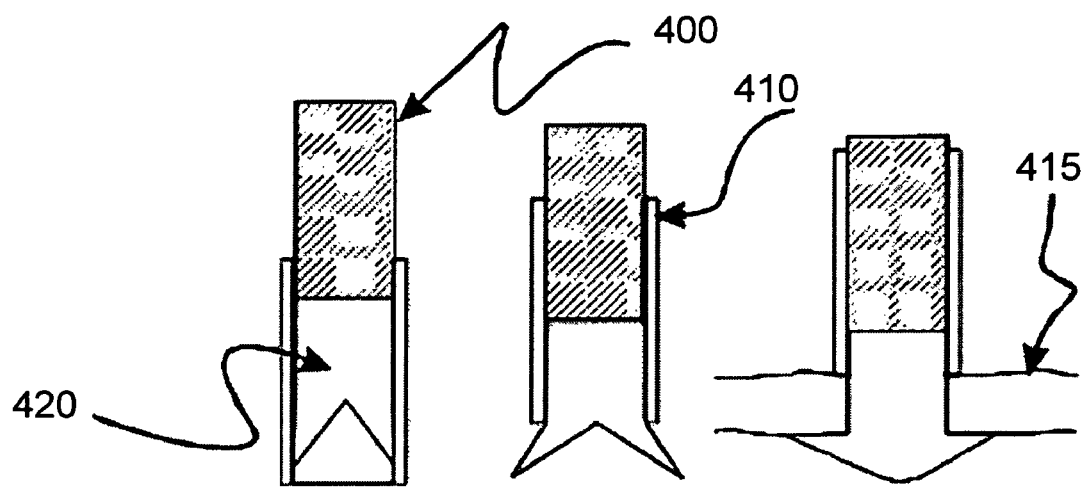
FIGS. 25A-B depict different anchors for use within hollow anatomical structures.
Figure 25B:
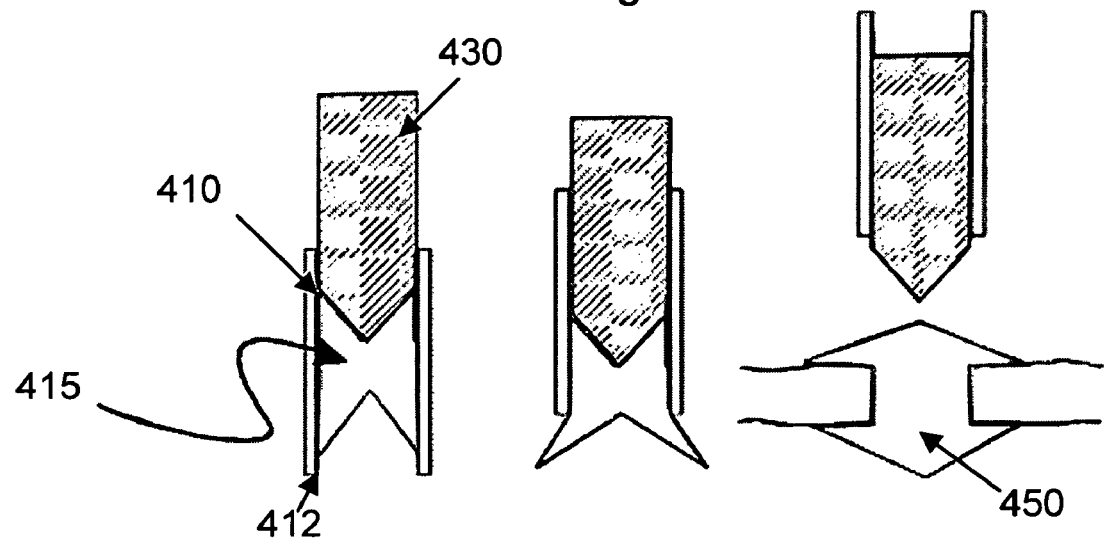

FIGS. 25A-B depict examples of self-expanding fusion compositions. In FIG. 25A, a plunger 400 is used to push a fusion composition 420 out the end 412 of a sheath 410 positioned in tissue 415 such as a blood vessel. Upon retraction of the sheath 410 and plunger 400, the composition 420 expands in a way to seal the defect in the tissue 415. In FIG. 25B, another fusion composition 430 is depicted which serves to occlude the defect in tissue 415 from both sides. The fusion composition 450 is pushed out the end 412 of the sheath 410 with plunger 430. Upon retraction of the sheath 410 and plunger 430, the composition 450 expands to seal the defect in the tissue 415.

Figure 26:
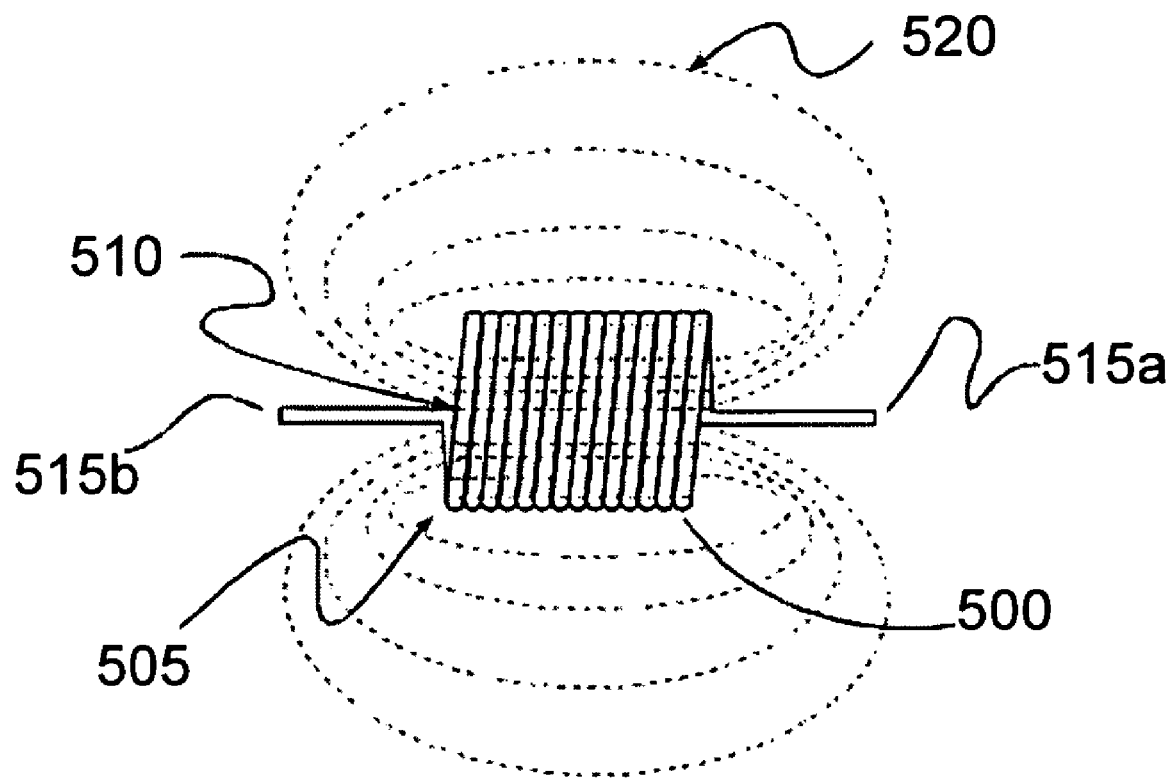
FIG. 26 depicts a solenoid-type coil applicator carrying an electrical current and the resultant magnetic field lines.

FIG. 26 depicts an applicator 505 having an essentially solenoid structure 500 which is formed with an interior cylindrical zone 510. The magnetic field lines 520 produced when an electrical current is passed through the wire at 515a,b is shown. While the greatest magnetic intensity H (A/m) occurs within the applicator, a weaker magnetic field occurs at the ends and outside of the solenoid.

Figure 27:
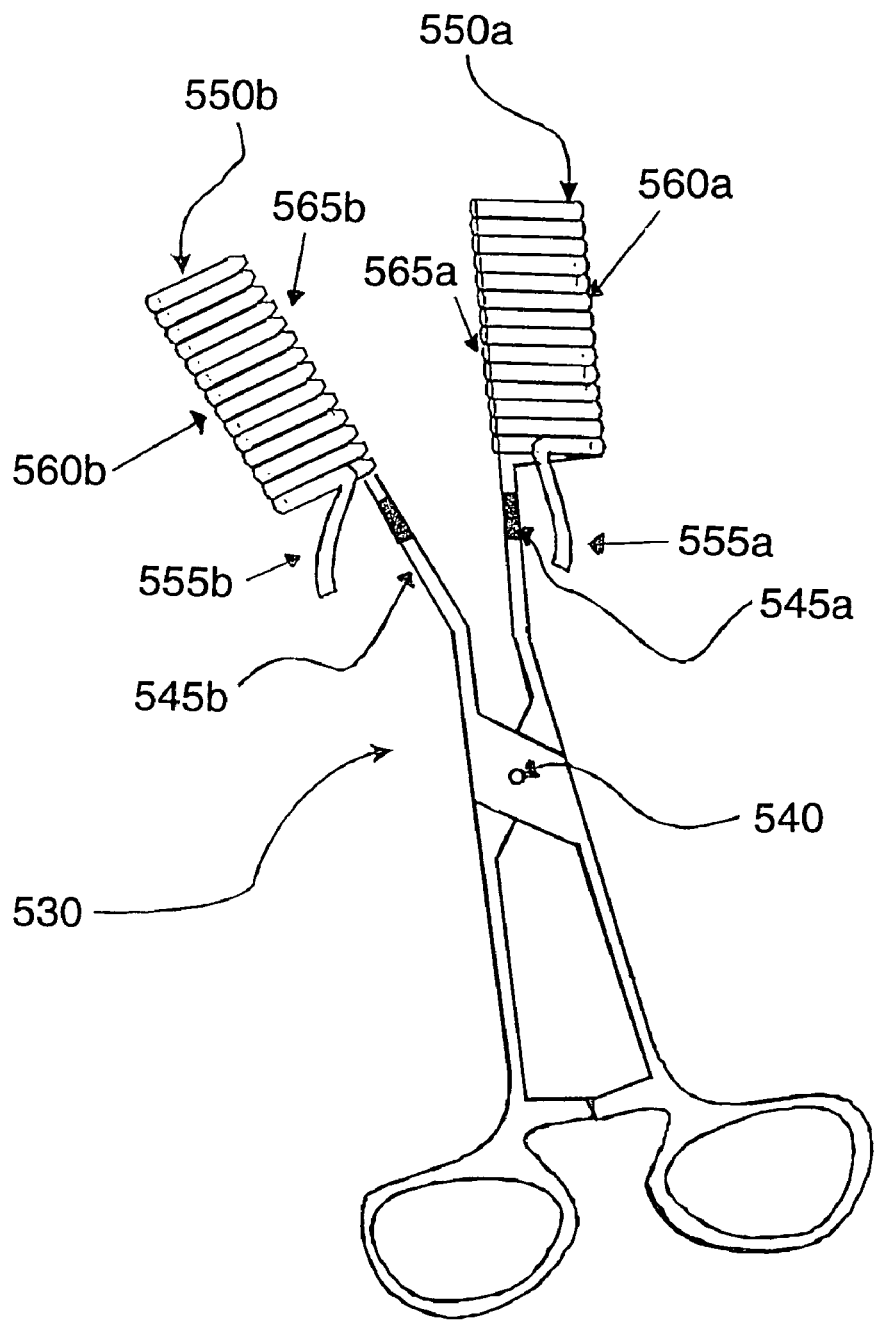
FIG. 27 depicts a coil applicator that can be split thus allowing positioning of tissue in the interior of the coil.

In FIG. 27 and with continued reference to FIG. 26, a solenoid-type applicator 530 is constructed such that the coil-halves of the solenoid 550a,b can be opened, closed or adjusted via a clamp-like handle 540, thus allowing the positioning of an anatomical structure within the interior cylindrical zone 565a,b. When the coil-halves 550a,b are closed via the scissors-like action of the handle 540, electrical contact is established. The resulting intensity H is consistent with the field 520 shown in FIG. 26. The handle 540 is electrically isolated from the coil-halves 550a,b by insulator 545a,b. The power is conducted to the coil with electrical leads 555a,b.

Figure 28A:
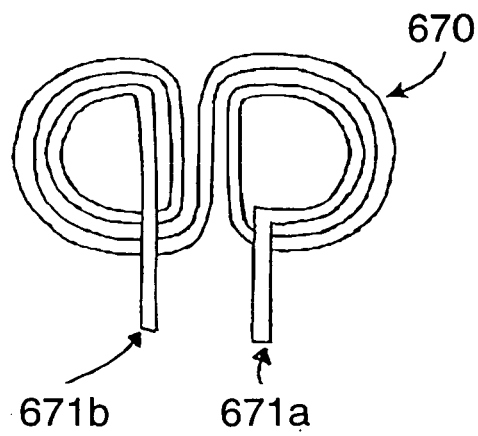
FIGS. 28A-28C depict configurations of three flat pancake coils.
Figure 28B:
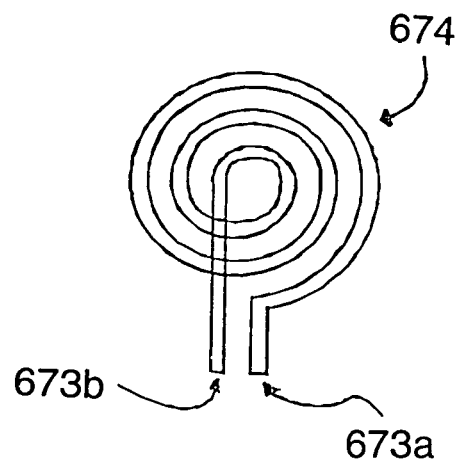
Figure 28C:
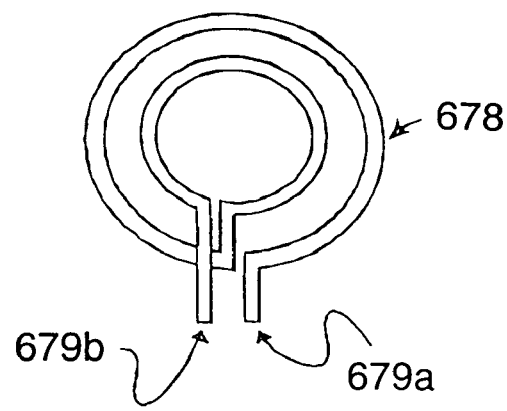

FIGS. 28A-28C depict substantially flat applicator coils for activating in other anatomical geometries. FIG. 28A is a "butterfly coil" 670 with electrical connectors 671a,b. FIG. 28B is a spiral coil 674 with electrical connectors 673a,b. FIG. 28C is an alternative spiral coil 678 with electrical connector 679a,b. Each coil produces a magnetic field with a particular geometric shape. For example, coil 670 produces a two-lobed shaped field above and below the flat plane of the coil. With the addition of a material, such as mumetal (not shown), it is possible to shield the superior surface of the coil 670 if no magnetic field is desired above the coil.

Figure 29A:
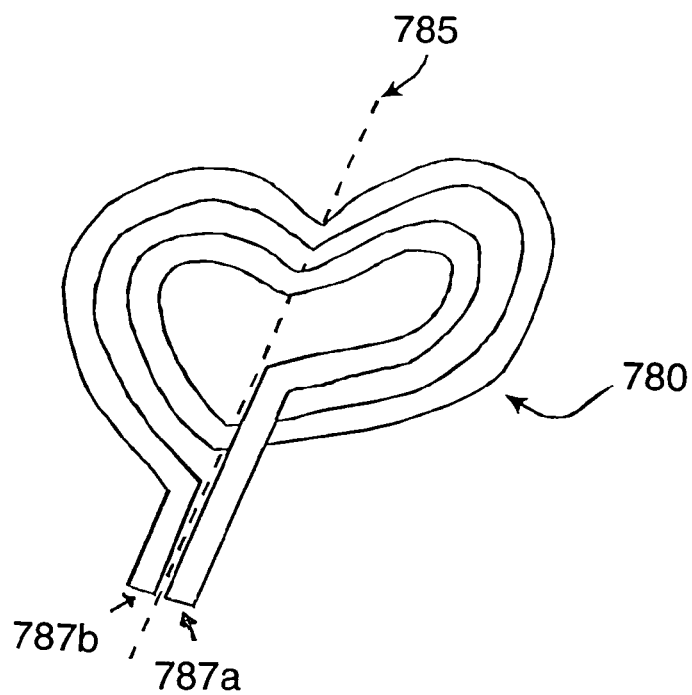
FIGS. 29A-29B depict a pancake coil with a non-planar geometry (FIG. 29A) and a conical spiral coil geometry (FIG. 29B).
Figure 29B:
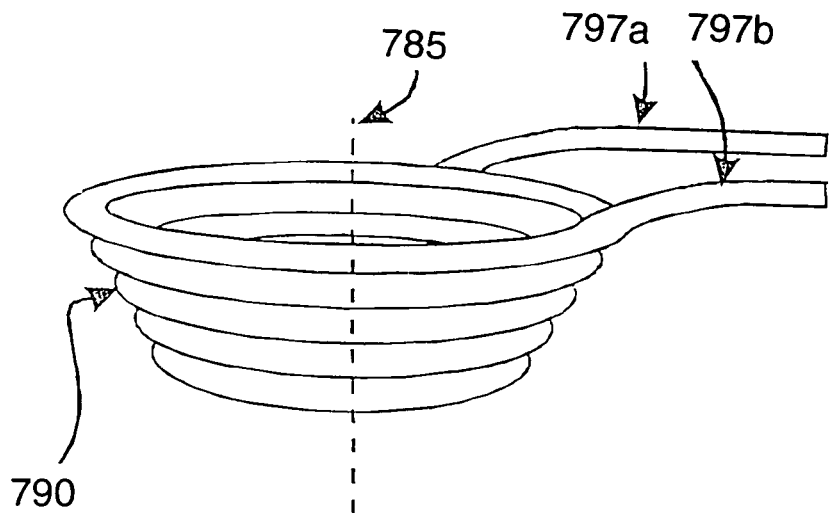

In FIGS. 29A-29B and with continued reference to FIG. 28, non-planar coil applicators are illustrated. FIG. 29A depicts a coil 780 similar to 674 in FIG. 28A, however each half of 780, as delineated by a centerline 785 is bent towards and along the centerline 785, thus increasing the magnetic field intensity H at a position within a volume contained within the bent coil 780. The power is connected to the coil through leads 787a,b. FIG. 29B depicts a coil 790 which is in the form of a conical spiral with axis of symmetry 795. The power is connected to the coil through leads 797a,b.

Figure 30:
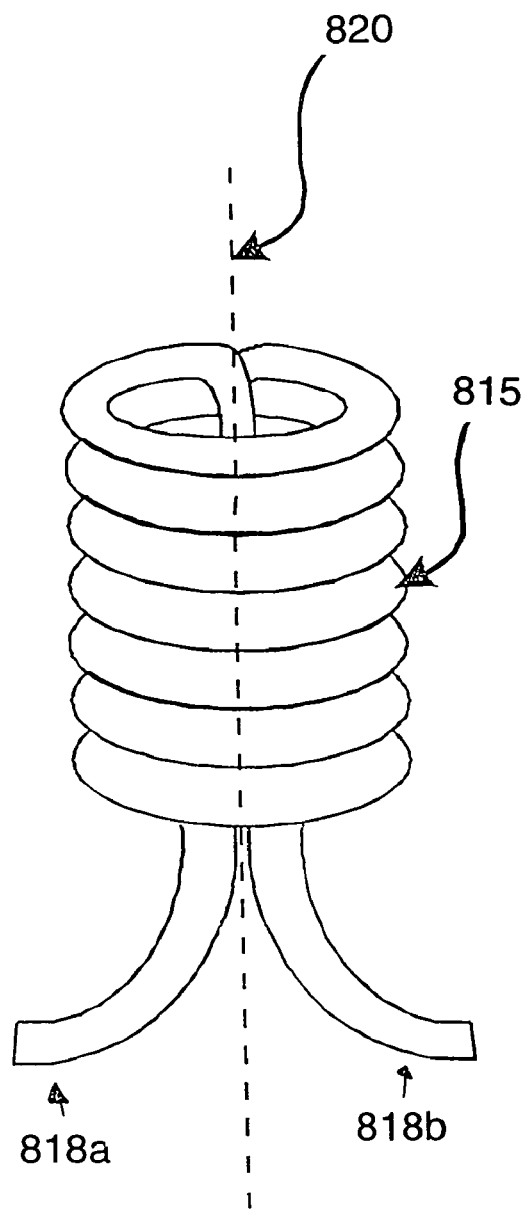
FIG. 30 depicts an applicator suitable for use within hollow structures such as blood vessels.

FIG. 30 shows a fusion applicator coil 815 with electrical connectors 818a,b which is symmetrical around axis 820 and which is designed for use in a hollow anatomical structure, such as a blood vessel (not shown).

Figure 31:
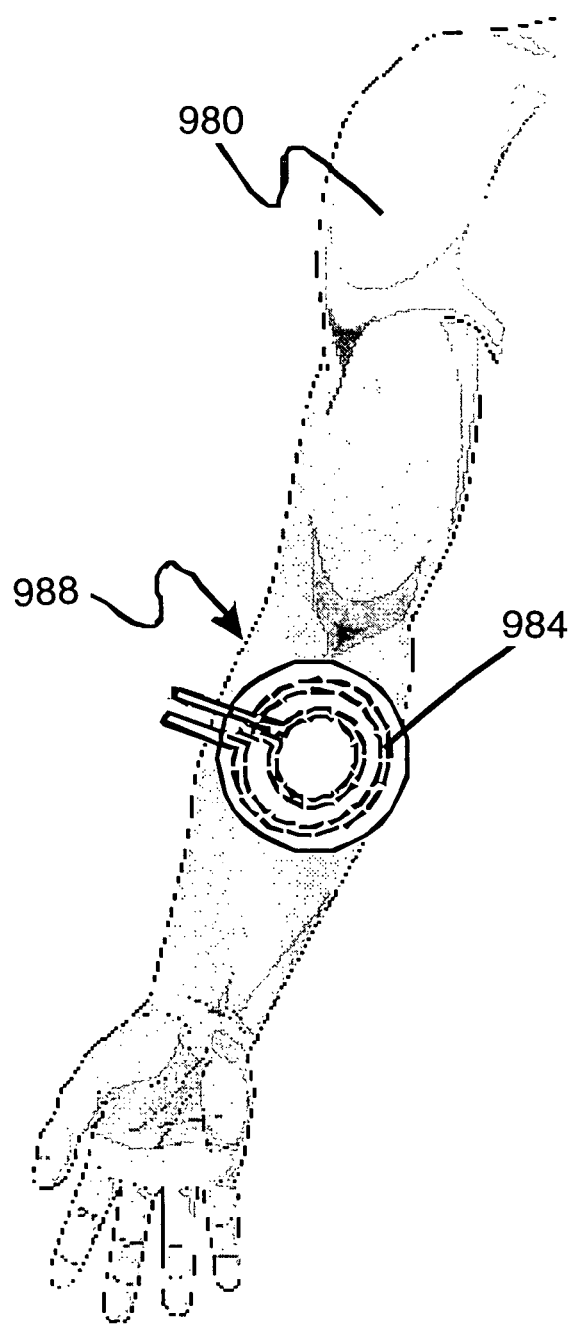
FIG. 31 shows a coil type applicator, substantially made out of an electrically non-conducting material, positioned on the arm of a subject for in vivo use. The coil inductor antenna 84 is housed within the applicator. This device could be used in vivo to induce conformational changes in reactants coupled with transducer species.

FIG. 31 shows a coil type applicator 988, substantially made out of an electrically non-conducting material, positioned on the arm 980 of a subject. The coil inductor antenna 984 is housed within the applicator. This device could be used in vivo to induce conformational changes in reactants coupled with transducer species.

Figure 32A:
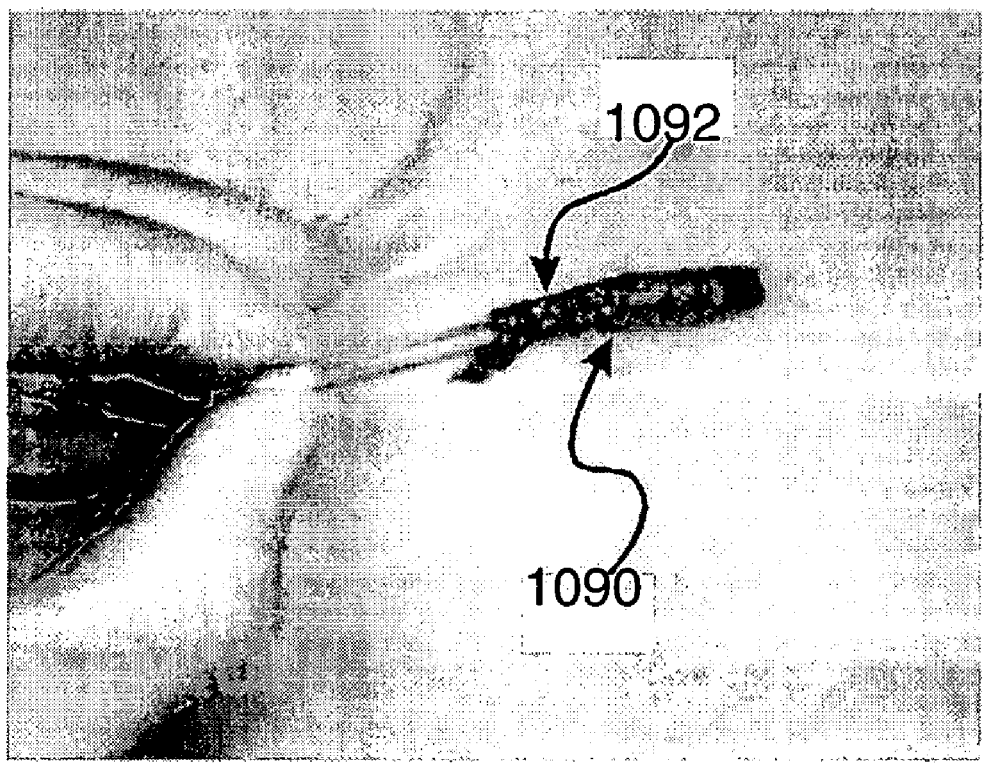
FIG. 32A shows the anastomosis or fusion of two sheep arteries with a fusion composition using inductively-applied radiofrequency energy to fuse the arteries.

FIG. 32A depicts depicts the visible fusion 1092 of a vascular vessel 1090.

Figure 32B:
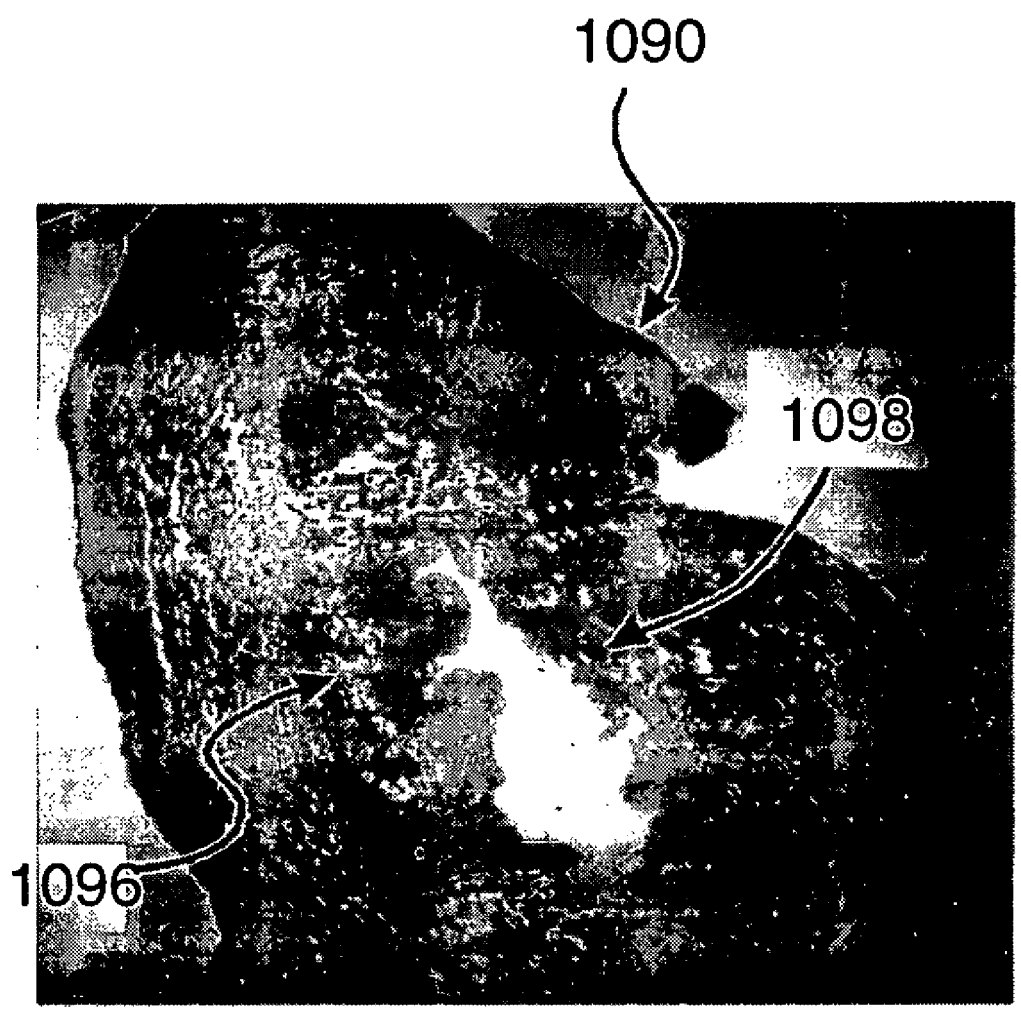
FIG. 32B histologic section across the lumens at the fusion juncture of the sheep carotid arteries.

FIG. 32B, with reference to FIG. 20, shows a histological section of the vascular vessel vascular vessel 1090 with metallic particles 1096 and 1098 at the interface 1092 between the two overlapping sections.

Figure 33:
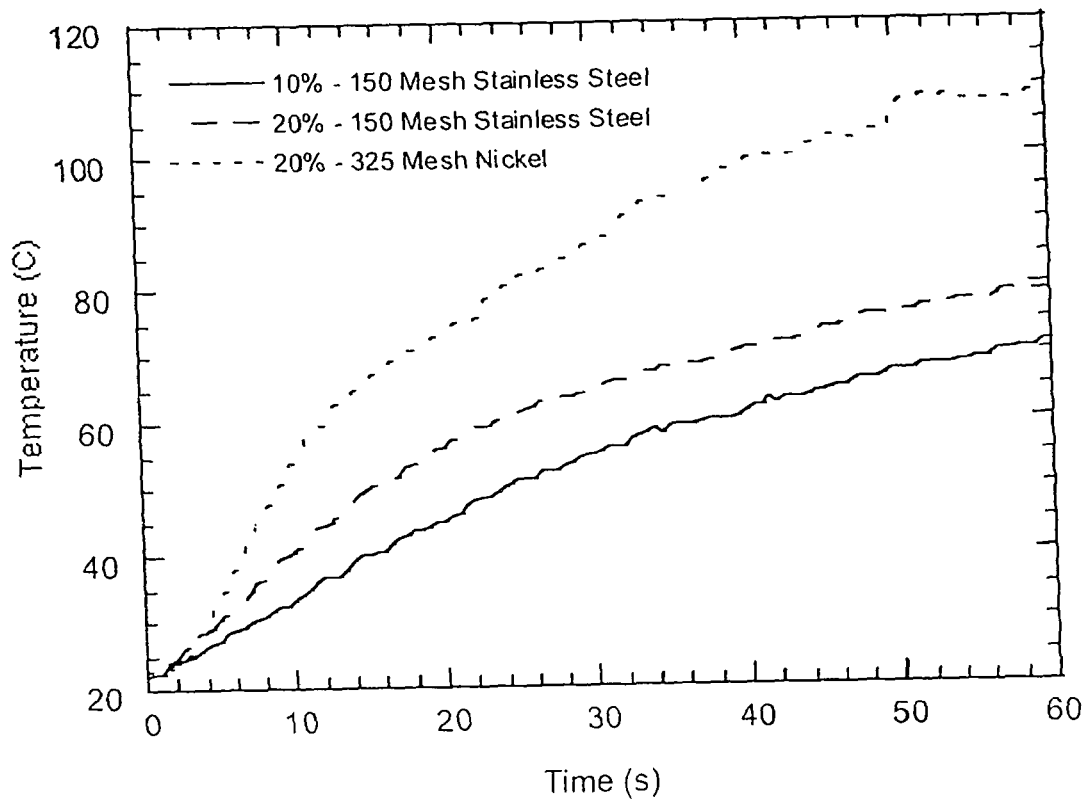
FIG. 33 compares temperature over time for heating fusion compounds using a commercially available induction power supply.

FIG. 33 shows the surface temperature as a function of time of three different fusion compositions being inductively heated.

Figure 34A:
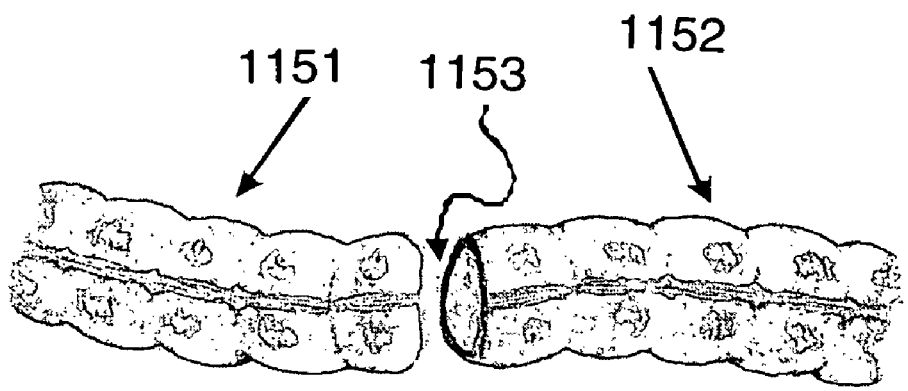
FIGS. 34A-34E depict a series of steps that may be taken during colon anastomosis with the immediate invention.
Figure 34B:
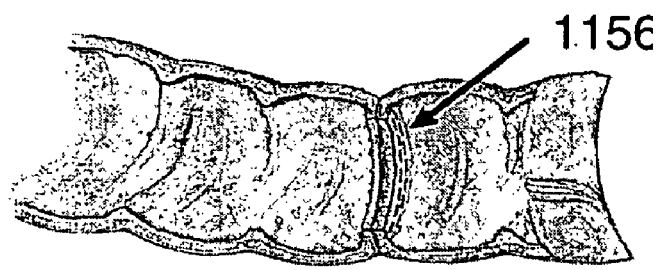

FIGS. 34A-34E depict the steps taken in using the immediate tissue fusion device invention in anastomosing the colon. FIG. 34A show two lengths of a colon 1151,1152 and a region of apposition 1153 where a length of diseased colon was removed. In FIG. 34B, the current standard of care of anastomosing a colon is shown, where apposed ends of the colon were butted up against one another and stapled around the internal periphery 1156 using a standard circular surgical stapler.

Figure 34C:
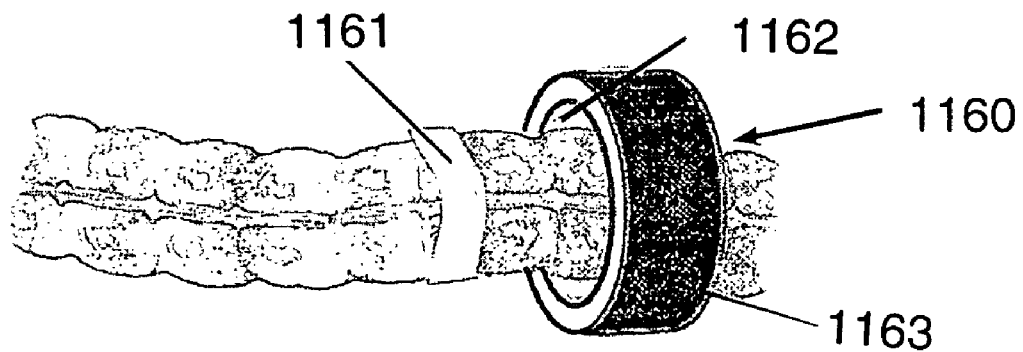
Figure 34D:
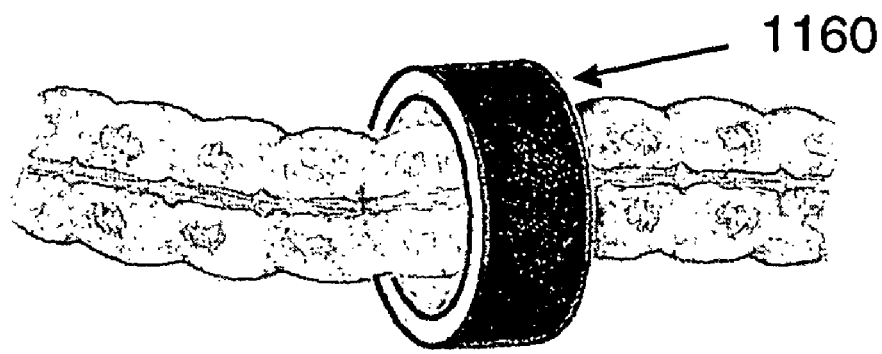
Figure 34E:
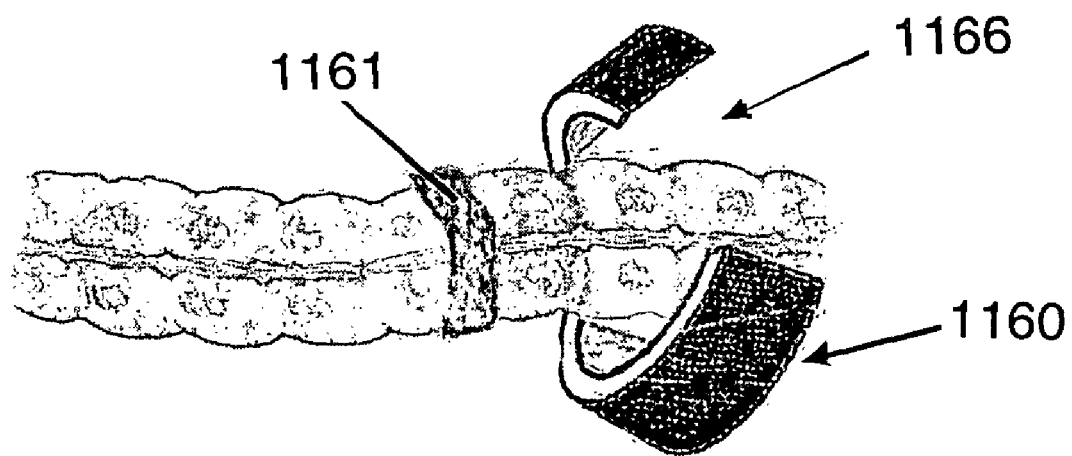

Alternative to the procedure in FIG. 34B, FIG. 34C shows the opposed ends of a colon where the region of apposition is covered with a fusion composition optionally in the form of a tape 1161 and an activation coil 1160, with an interior surface 1162, optionally not in contact with the exterior surface of the colon, and an exterior surface 1163. In FIG. 34D, the activation coil 1160 is positioned over the fusion tape 1161, and energized at a power and for a time suitable to induce the desirable transformation in the nature of the fusion composition. In FIG. 34E, the activation coil 1160 is cut away 1166 and the fused colon is shown, with the activated fusion composition 1161.

Figure 35:
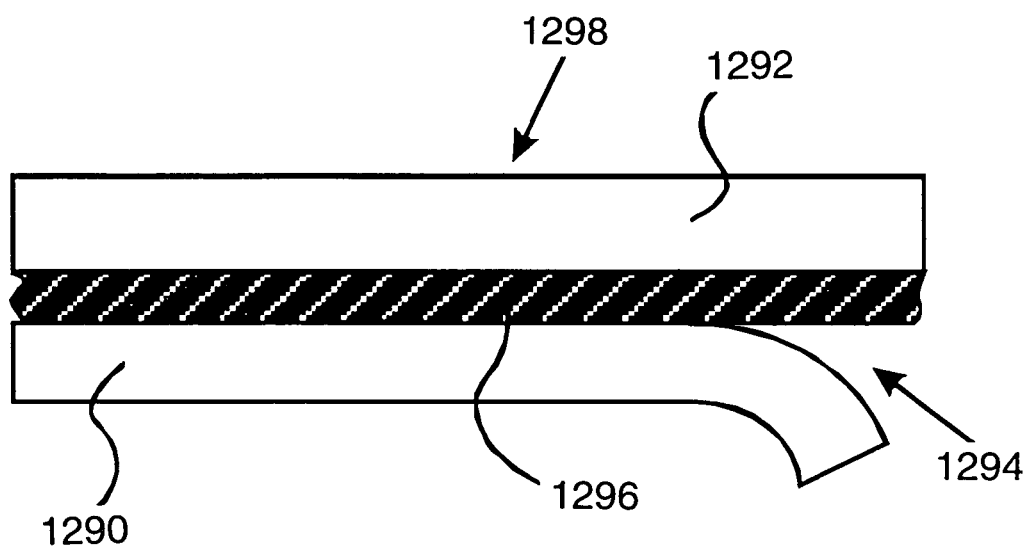
FIG. 35 depicts fusion composition in the form of a laminate, or tape, which can be easily applied to the tissue to be anastomosed.

FIG. 35 depicts a tissue tape 1298 comprising a biocompatible material 1292, the inferior surface of which is disposed on and in contact with the superior surface of a fusion composition layer 1296. The superior surface of the biocompatible material 1296 is disposed on and in contact with the inferior surface of a biocompatible material 1292 that allows the care provider to apply downward force to the tape 1298 and not contaminate the biocompatible material 1296. The covering material 1290 may be peeled away 1294 from the biocompatible material 1296 after application of the tape 1298 to the tissue (not shown). The biocompatible material 1292 may optionally dissolve overtime, leaving just the biocompatible material 1296.

Figure 36:
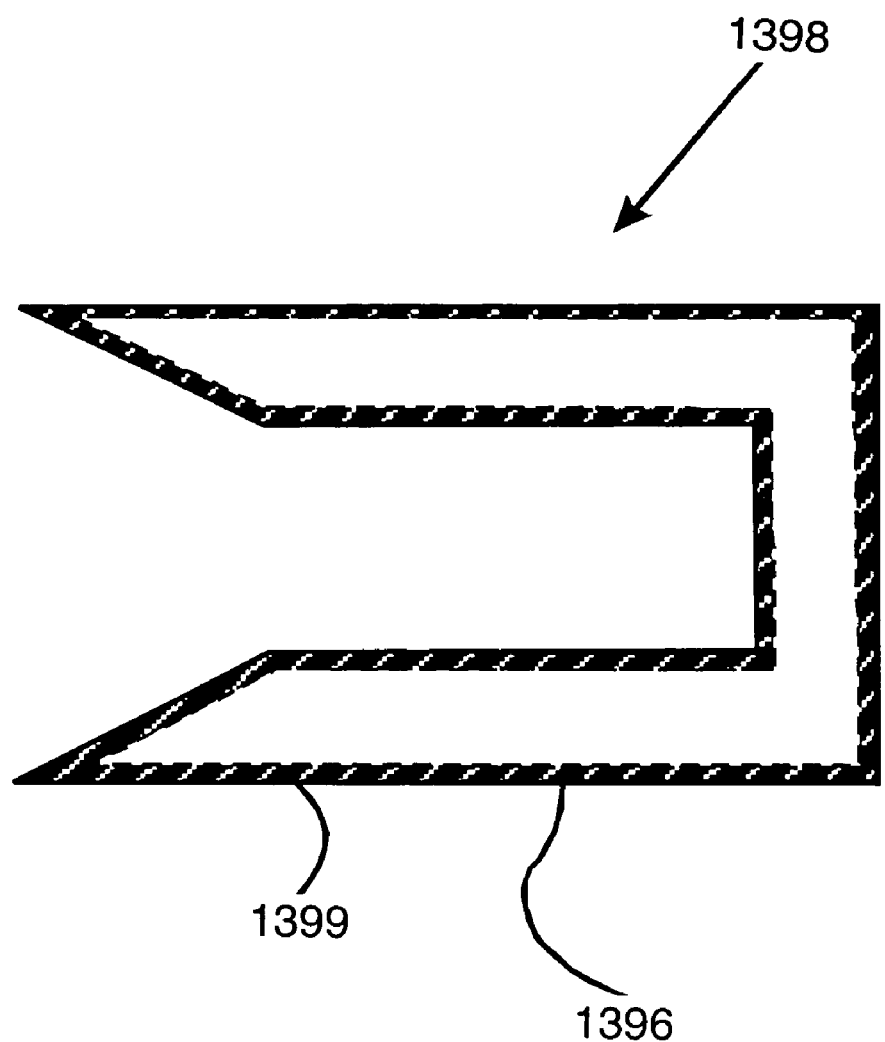
FIG. 36 depicts a surgical staple coated with fusion composition.

FIG. 36 depicts a coated surgical staple 1398 consisting of a support and linking structure coated with a bioadhesive. The staple 1399, typically made out of biocompatible material such as stainless steel, titanium, or metal alloys, is coated with a fusion material 1396, which when heated and cooled, serves as a fusion adhesive.

The fusion material may be albumin, but may also be a number of other biocompatible materials that have adhesive properties when heated. The staple may optionally be made out or resorbable material such as chromic or denatured albumin. If the staple is magnetically responsive, then it can be heated with an external radiofrequency magnetic field. Alternatively, the material in the staple can be microwave responsive and so be heated with externally applied microwaves.

Figure 37:
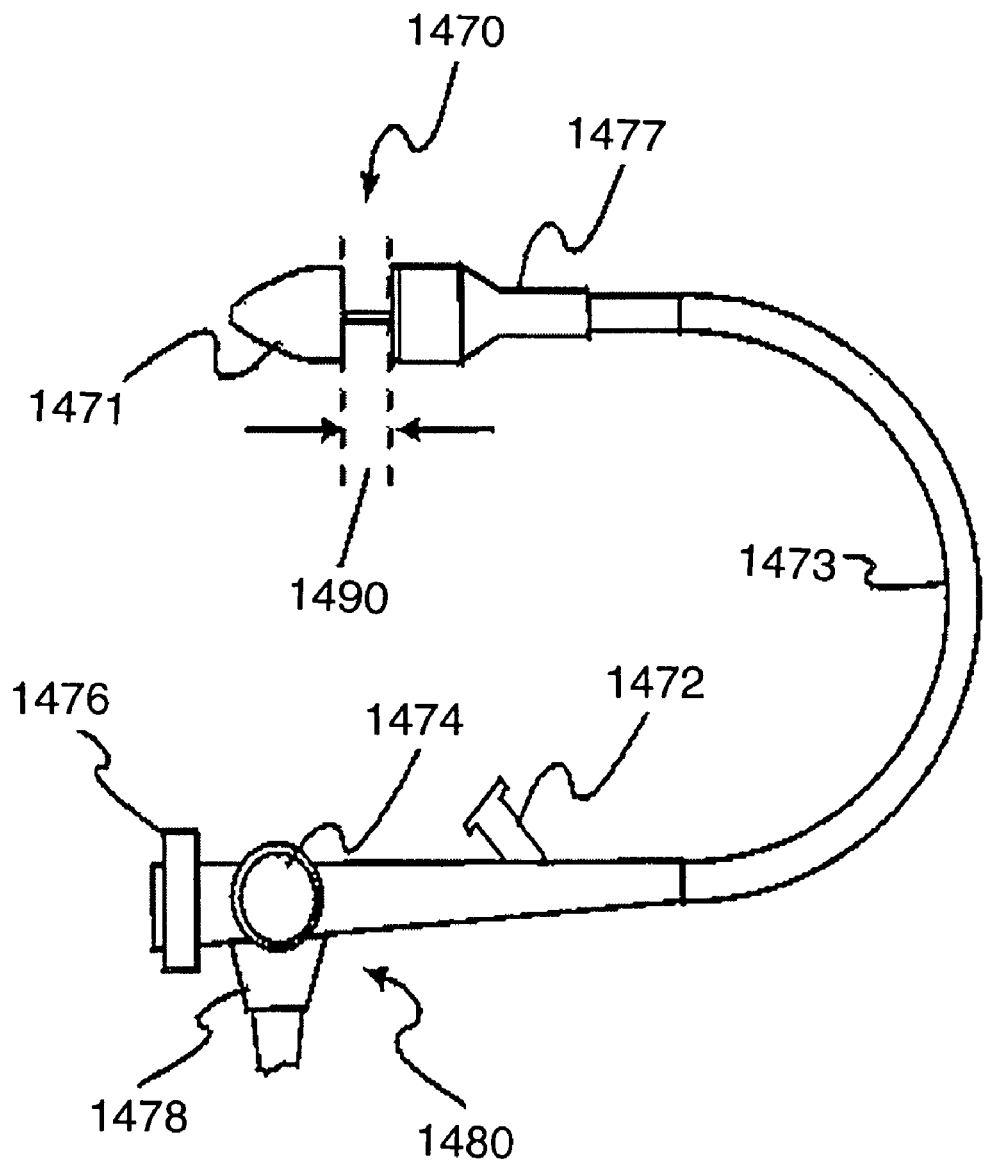
FIG. 37 depicts a circular tissue fuser which can be positioned within the lumen of tubular anatomic structures, such as colons, in order to perform end-to-end anastomoses with the immediate invention.

FIG. 37 depicts a circular tissue fuser applicator which can be positioned within the lumen of tubular anatomic structures, such as a colon, in order to perform end-to-end anastomoses with the immediate invention. The applicator consists of a distal end 1470 consisting of a smooth guide 1471 and base 1477. The end 1471 and guide 1477 are attached to a flexible cylinder 1473 through which optical imaging devices can pass, such as optical fibers and wires which provide power to the guide 1471 and base 1477. The proximal end of the circular tissue fuser applicator optionally may have ports 1472 for inserting light sources, such as optical fibers, imaging ports 1478 to which cameras or oculars can be attached and mechanical adjustors 1476 and 1474 which are used to adjust the position 1490 between the guide 1471 and base 1477, and actuate the cutting blade positioned within the base 1477.

Figure 38A:
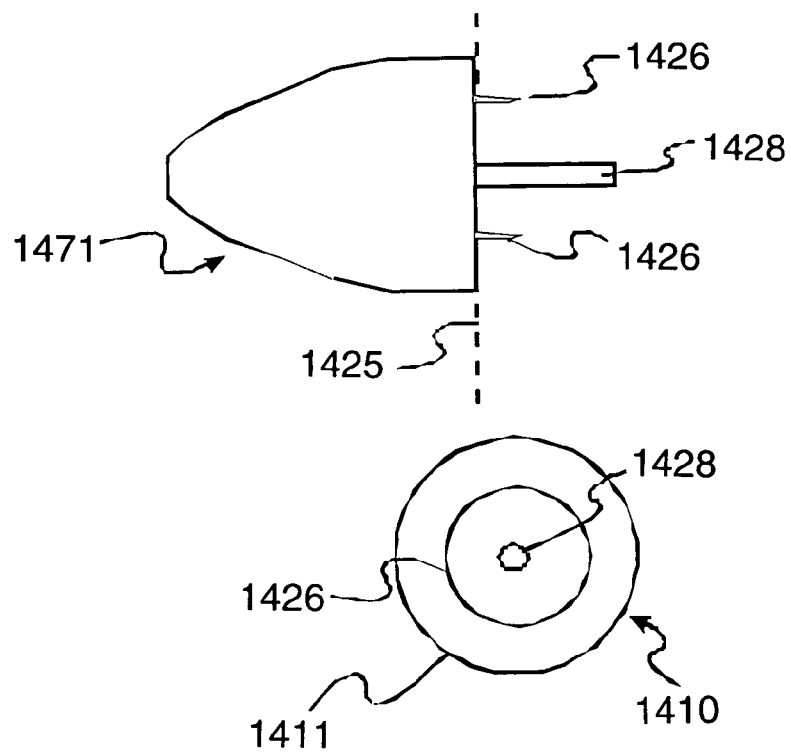
FIGS. 38A-38B depict a detailed view of the distal end of the circular tissue fuser.
Figure 38B:
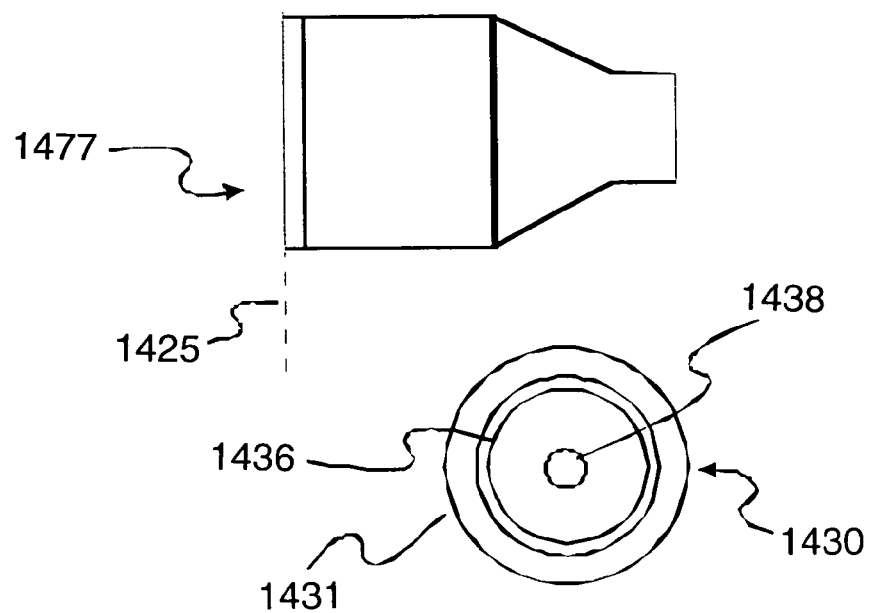

With further reference to FIG. 37, FIGS. 38A-38B depict a detailed view of the distal end 1470 of the circular tissue fuser applicator. In FIG. 38A, the penetrator 1571 is conically shaped such that it can be directed up a cylindrical anatomical structure with minimal trauma. A cutting blade 1426 in the form of an annulus is fixed to the penetrator, as is an adjustable connector 1428 which serves to change the distance 1490, shown in FIG. 37, between the penetrator 1471 and penetrator base 1477. In FIG. 38B the penetrator base 1477 has an annular depression 1436 into which the annular blade 1426 can travel and a female connector 1438 into which the adjustable connector 1428 can engage. The penetrator 1471 has a smooth outer surface, and the penetrator base 1477 also has a smooth surface in order to cause minimal disruption to the interior walls of the relevent anatomical structure. The distance 1490, shown in FIG. 37, between the penetrator and penetrator base is adjustable with controls 1474 and 1476 in the circular tissue fuser applicator. Either the penetrator 1471 or penetrator base 1477 may be a means of applying radiofrequency energy or electrical energy to the fusion composition, which may optionally take the form of an antenna, such as a coil.

When it is desirous to perform a colonic anastomosis, first the two ends of the remaining colon tissue can be juxtaposed, as in FIG. 34A, and fusion composition can be applied between the ends of the tissue or around the area of juxtaposition. The circular tissue fuser applicator can then be positioned within the lumen of a colon at the area of juxtoposition, with the penetrator within the lumen of one end of the colon to be fused, and the penetrator base within the other end of the colon to be fused. The tissue of the colon ends may be configured as shown in FIG. 34A.

The penetrator 1470 and penetrator base 1477 can then be drawn together such that the distance between them, 1490, decreases to the point whereupon the circular cutter 1426 extends into the annular depression 1436 and a circular tissue perforation is created. Subsequently, the means of applying radiofrequency energy or electrical energy is engaged and the fusion composition is cured. The circular tissue fuser applicator and annular ring of resected colon can then be extracted by withdrawing the entire device from the colon.

FIGS. 39A-39E depict a tubular structure, e.g. colon, sealing device. With further reference to FIGS. 38A-38B, when used for sealing two dissected sections of a colon, 1510 and 1520, the device can be positioned within the lumen of the colon (FIG. 39A), and subsequently the two ends 1471 and 1477 of the device can be drawn together (FIG. 39B) to sandwich an layer of tissue 1560 with an annular shape between the ends 1471 and 1477.

If a magnetically responsive fusion composition, in the form of a viscous composition or solid annular shaped composition, is positioned between the annular layers of tissue prior to drawing the ends 1471 and 1477 together, then the ends 1471 and 1477 can act as opposite poles of an antenna and when radiofrequency energy is applied to each end, the fusion composition is heated thus effecting tissue fusion. Alternatively, the ends 1471 and 1477 of the sealing device can be attached to the ground and active conductive of a coaxial cable attached to a microwave source, thereby causing heating of the tissue between the ends thus effecting tissue fusion.

As in FIGS. 34C-34E, FIG. 38C shows the opposed ends of a colon where the region of apposition is covered with a fusion composition optionally in the form of a tape 1610 and an activation coil 1600, with an interior surface 1620, optionally not in contact with the exterior surface of the colon, and an exterior surface 1630. In FIG. 38D, the activation coil 1600 is positioned over the fusion tape 1610 and energized at a power and for a time suitable to induce the desirable transformation in the nature of the fusion composition. In FIG. 38E, the activation coil 1600 is cut away 1660 and the fused colon is shown, with the activated fusion composition 1610.

Figure 39A:
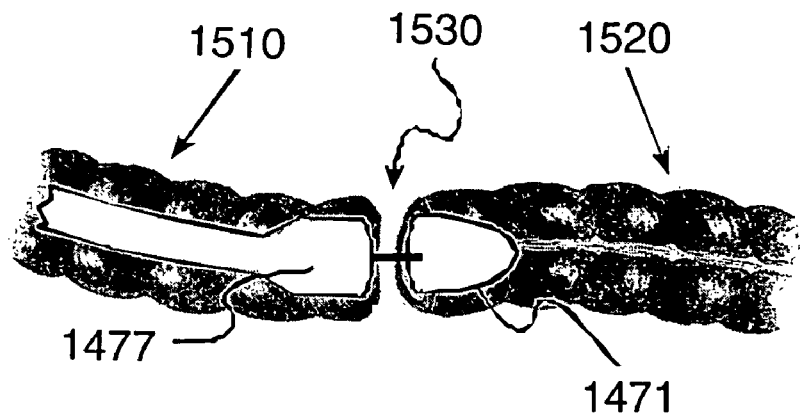
FIGS. 39A-39E depict the use of a circular tissue fuser to perform and end-to-end anastomosis and/or to seal the line of juxtaposition of an anastomosis.
Figure 39B:
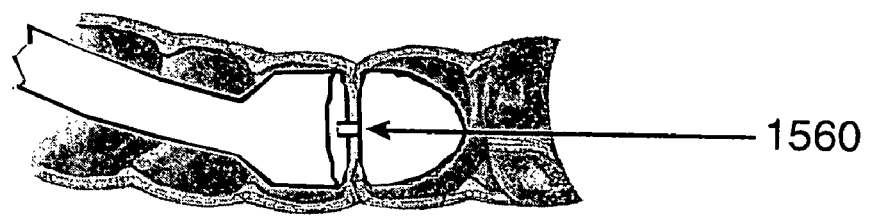
Figure 39C:
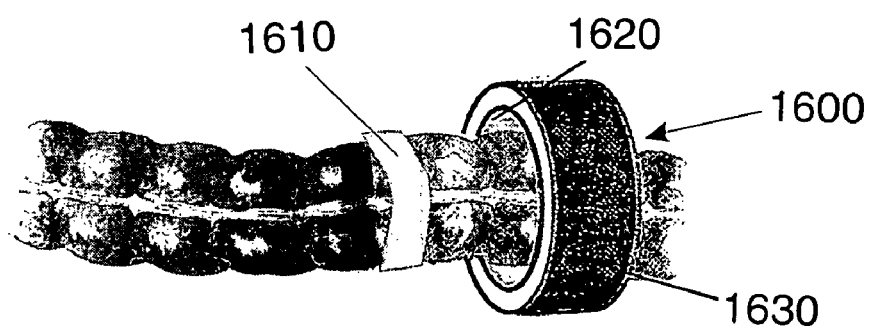
Figure 39D:
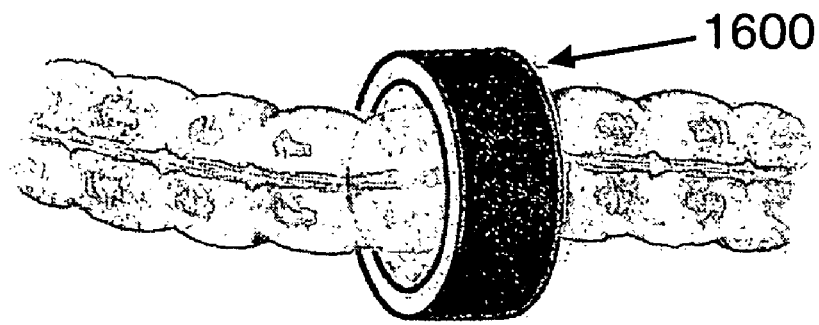
Figure 39E:
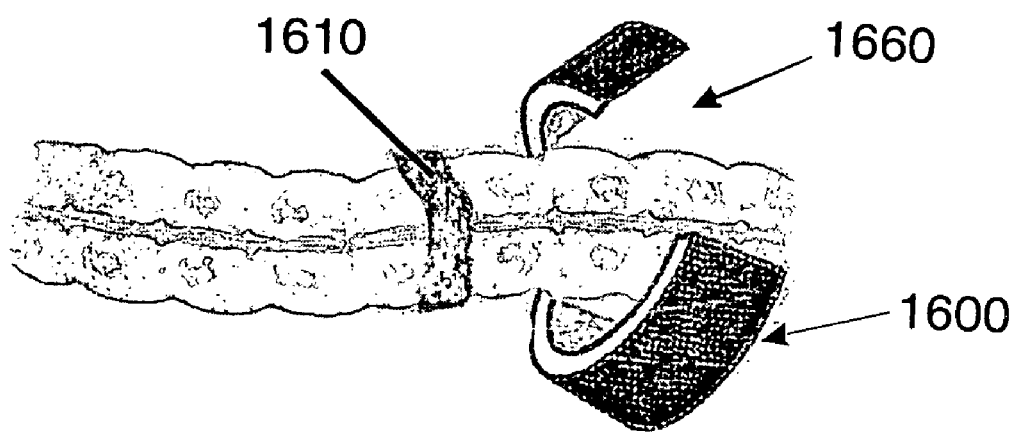
Figure 40A:
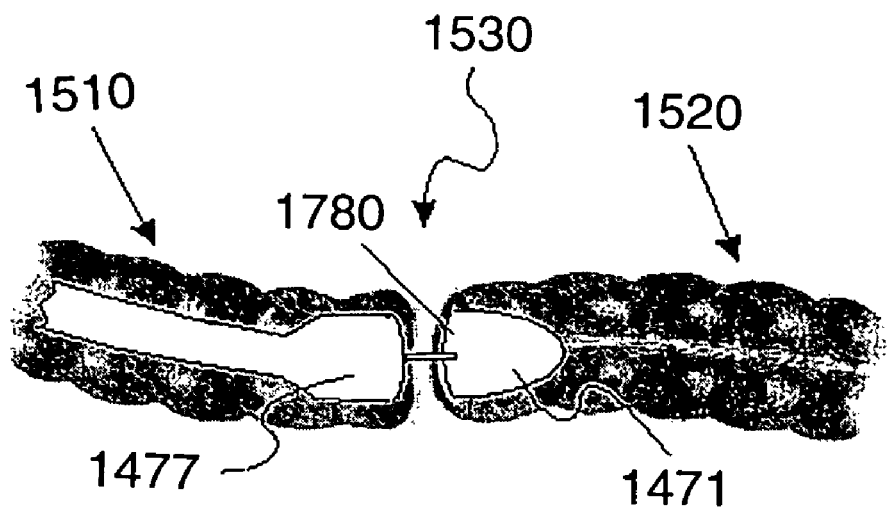
FIGS. 40A-40B depicts a circular tissue fuser.
Figure 40B:
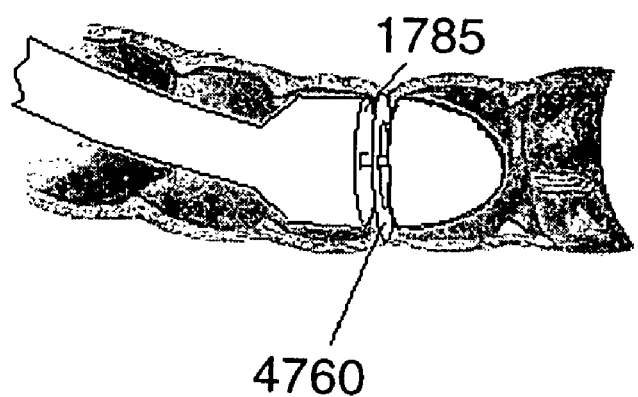

With continued reference to FIGS. 39A-39E, FIGS. 40A-40B illustrate another tubular structure sealing device. In FIGS. 40A-40B, the ends of a colon 1510 and 1520, for example, can first be drawn together. Optionally, a fusion composition can be placed between the annular ends of the tissue to be sealed. Heat is applied to the juxtaposed tissue by resistively heating the opposing faces 1780 and 1785 of each end 1471 and 1477 of the sealing device. Optionally and subsequently, an activating coil 1600, as shown in FIG. 39C, can be positioned over the juxtaposed tissue which may or may not have fusion composition 1760 applied to the ends of the tissue or outside surface of the tissue incision to act as a leak-proof seal. The tubular structure sealing device can then be heated by the inductive or radiative application of energy to the ends 1471 and 1477 of the conductive sealing device whereupon the fusion composition 1760 is heated and the tissue is fused.

Figure 41:
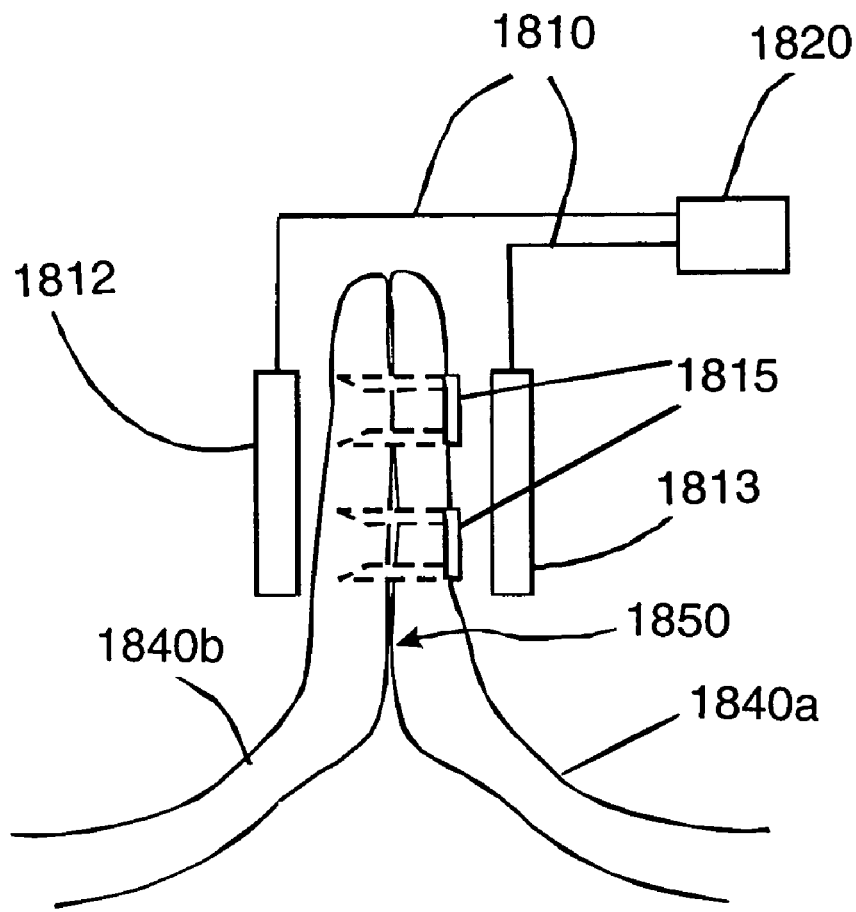
FIG. 41 depicts one use of an activatable surgical staple in fixing two pieces of tissue and the method by which it is activated.

FIG. 41 depicts one use of the coated staple. With continued reference to FIG. 36, FIG. 41 shows coated surgical staples 1815, positioned between two planes 1840a,1840b of tissue. The staples 1815 can be activated with an external power supply 1820, which is connected by conductive shielded cables 1810 to two electrodes 1812,1813. Energy, e.g. radiofrequency, can then be applied to the electrodes 1812,1813 thus creating an alternatively electric field therebetween, which preferentially interacts with the staples 1815 thereby causing heating and tissue fusion. Alternatively, the electrodes 1812,1813 may be replaced by a coil (not shown) and a radiofrequency magnetic field may be produced thus effecting inductive heating of the staples 1815 and subsequent tissue fusion.

Figure 42:
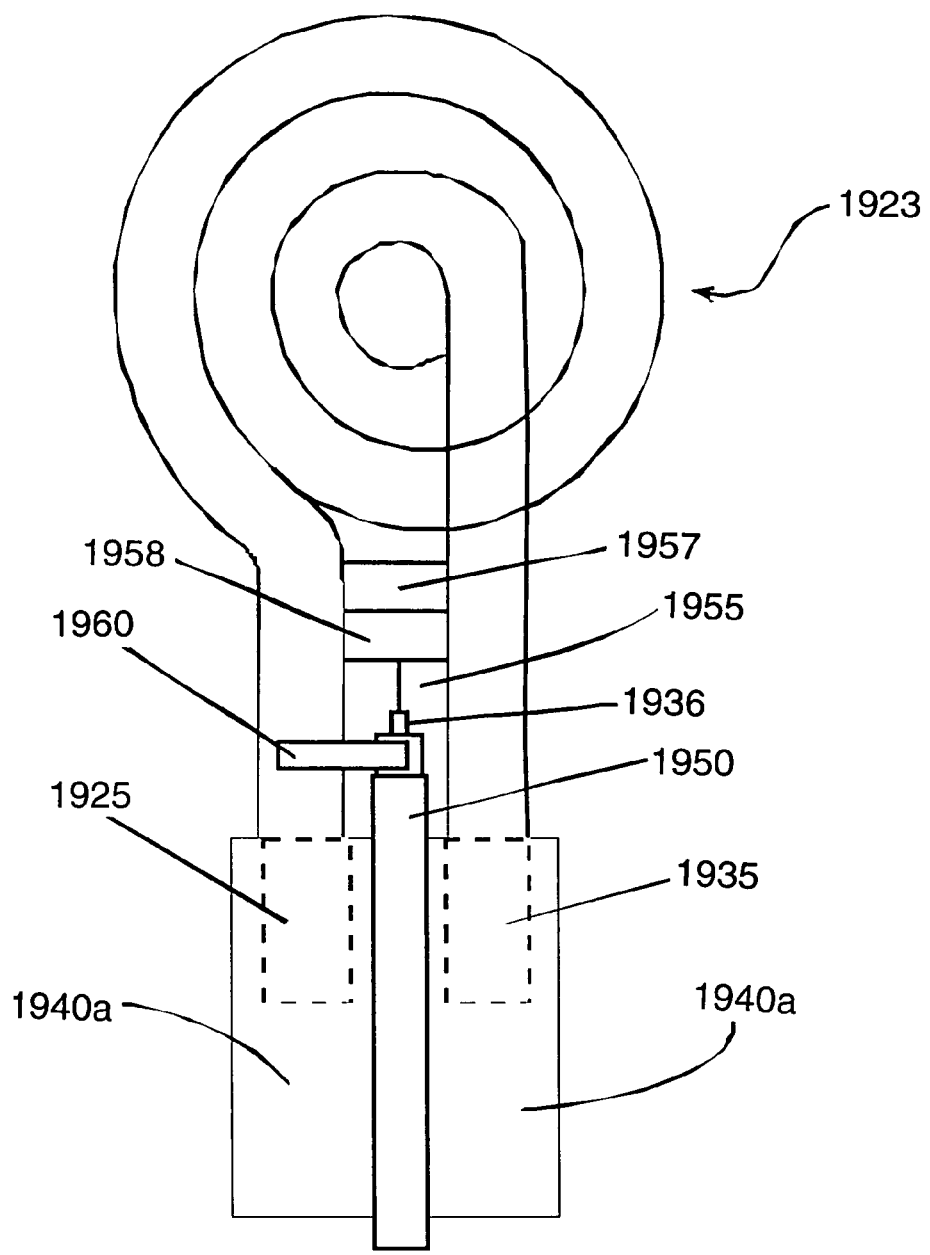
FIG. 42 depicts a solenoid coil applicator with cooling and impedance matching electronics.

FIG. 42 depicts one configuration of an induction tissue heating applicator. Copper tubing is coiled into a two turn planar pancake 1923. Small high-voltage radiofrequency capacitors 1957, 1958,1955 are positioned in electrical contact with each end of the coil 1923. At least one capacitor, 1955, is connected electrically between the coil 1923 and the central conductor 1936 of a coaxial cable 1950. Radiofrequency power is conducted to one end of the coil 1923 through the central conductor 1936 of the cable while the cable 1950 is grounded through an electrical connector 1960 to the other end of the coil 1923. The capacitor(s) allows the applicator to be impedance matched to the radiofrequency power supply to which the coil is attached. Electrically nonconducting tubing 1940a,b is attached to each end of the coil 1923 in order that cooling water may be circulated through the coil thus keeping the coil and capacitor(s) cool.

Figure 43:
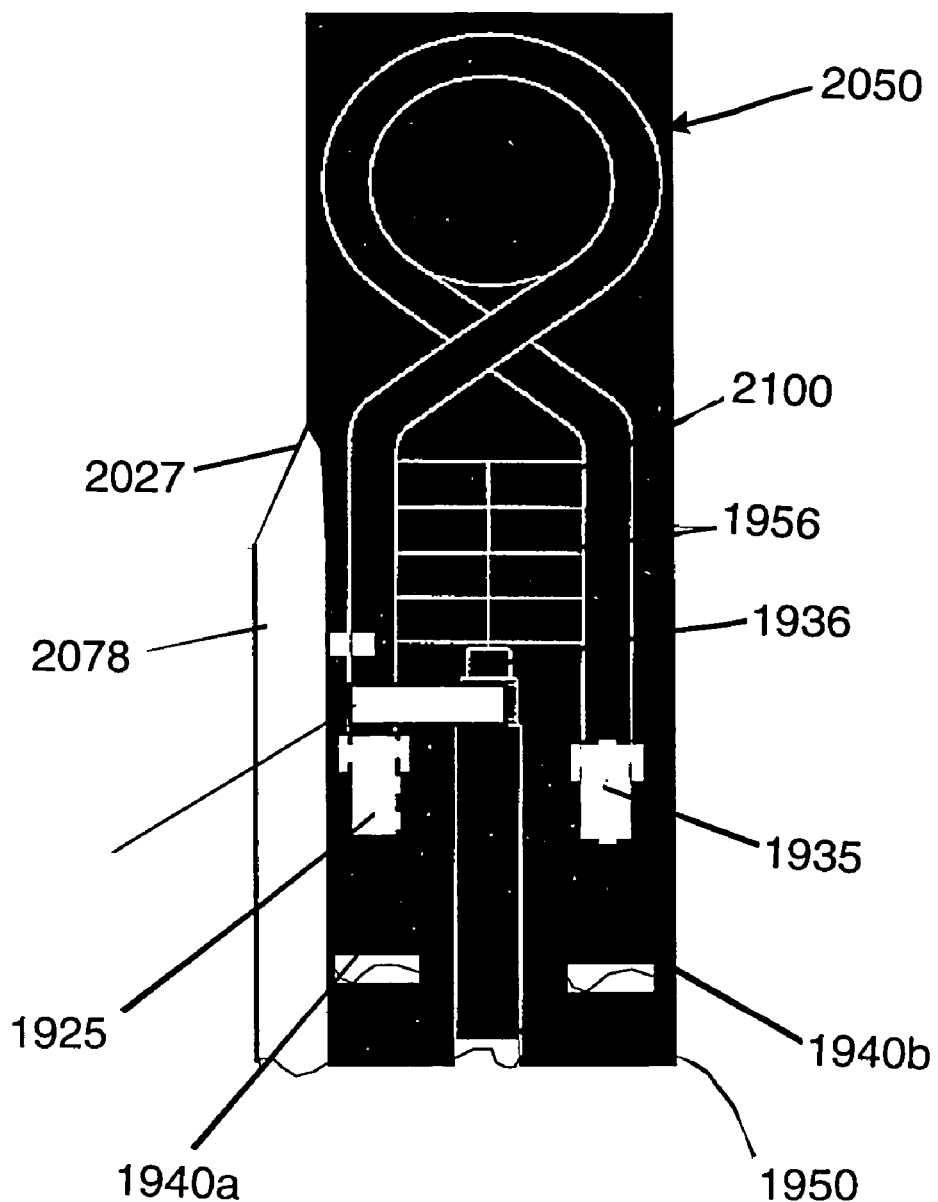
FIG. 43 depicts a pancake coil applicator with cooling and impedance matching electronics.

FIG. 43 depicts another configuration of induction tissue heating applicator. With continued reference to FIG. 42, the applicator in FIG. 43 is configured like a two turn solenoid 2050. The capacitors optionally can be configured as a bank of eight 1956 that are electrically connected between the ends of the coil 2050. The radiofrequency energy is applied to the central common conductor of the bank of capacitors by the central conductor 1936 of a coaxial cable 1950. In order to provide for precise control over the thermal history of the tissue heated with this device, an optional applicator 2078 is positioned adjacent to the coil, which can direct cooling cryoprotectant (e.g. air, water, carbon-dioxide) through a nozzle 2027 onto the tissue surface before, during or after the activation of the coil applicator.

The following examples are given for the purpose of illustrating various embodiments of the invention and are not meant to limit the present invention in any fashion.

Example 1

Heating of Test Metal

The prototype activator device was constructed (Quest Product Development, Evergeen, Colo.) and operates at a frequency of about 650 kHz with an output of approximately 210 W. At or near this frequency, the skin depth in tissue, e.g., canine skeletal muscle at 1 MHz, (Francis Duck. Physical Properties of Tissue—A comprehensive reference book. Academic Press: NY, 1990) is about 205 cm and for nickel it is about 14 microns. Thus, no significant heating of tissue occurs as a direct result of the field. Heating only occurs in close proximity to the fusion composition.

Two applicator designs were used and comprised 200 turns of solid copper wire, 32 and 22 G, resulting in a coil approximately 2.86 cm in diameter and 0.95 cm in width. The bore of the coil was about 0.5 cm. The coils were encapsulated in a Pyrex sleeve through which low-viscosity mineral oil (Sigma-Aldrich Inc., St. Louis, Mo.) is circulated as a coolant. In each of these coils, the magnetic intensity at the center of the coil is calculated to be greater than 10,000 A/m, while at approximately 0.5 cm from a single coil face the intensity is calculated to be maximally 160 A/m. The fusion composition was bovine serum albumin, 25, 50 and 75% by weight in water, combined with 325 mesh nickel flake (Alfa Aesar, Ward Hill, Mass.). The composition was homogeneously mixed and used immediately afterwards.

Aliquots of approximately 1 ml of the fusion composition were positioned in thin-walled glass tubes with a diameter of about 4 mm. The tube was then positioned in the bore of the applicator. The device was energized for a period of 30 seconds. Evidence of denaturation and coagulation was ascertained visually as the material changed color. This was confirmed by probing the composition with a needle and looking for evidence of increased viscosity or stiffness. The composition coagulated with all combinations of applicator and compositions.

A small screwdriver (Craftsman Model 41541, 3.15 mm diameter) was positioned within the bore of the coils. After 1-5 seconds, the screwdriver was extracted and the metal was brought transiently into contact with the skin of the hand. It was immediately apparent that significant heating had taken place.

Example 2

Heating and Coagulating of Test Fusion Formulation

Fusion formulations were made of 50-75% (w/v) bovine serum albumin or ovalbumin (Sigma-Aldrich, St. Louis, Mo.) in saline with a metal additive of 5% or 10% (w/v) nickel flake with average particle size of about 50 micron (Alfa Aesar, Ward Hill, Mass.) or 10% iron filings with particle size <30 microns (Edmund Scientific, Tonawanda, N.Y.). Approximately 1 ml aliquots of the fusion composition were positioned in thin-walled glass tubes with a diameter of about 4 mm. The tube was positioned in the bore of the applicator. The device was energized for a period of 20-30 seconds. Evidence of denaturation and coagulation was ascertained visually, as the material changed color. This was confirmed by probing the composition with a needle which demonstrated evidence of increased viscosity or stiffness. The composition coagulated with all combinations of applicator and composition. Compositions with more metal or iron versus nickel heated at different rates.

Example 3

Protein Denaturation

A radiofrequency electromagnetic device, operating at 650 kHz, was constructed. Near this frequency, the skin depth in tissue, using conductivity values for canine skeletal muscle at 1 MHz, is about 205 cm, while for nickel, it is 14 μm. Two solenoid type coils were constructed using 20 G solid copper wire. The coils were encapsulated in a Pyrex sleeve through which low-viscosity mineral oil is circulated as a coolant. Two coils had 200 turns of solid copper wire, formed into a solenoid, with a diameter of 2.86 cm and width of 0.95 cm. The magnetic intensity within the bore of the coil was calculated to be greater than 100 kA/m, while at approximately 0.5 cm from a single coil face the intensity is calculated to be maximally 0.15 kA/m. Two coils were electronically connected to the radiofrequency power supply and physically arranged with the bore axis parallel and opposing each other with a gap of about 2 cm between the faces of the coils.

The reactant was ovalbumin at a concentration of 50% (w/v) albumin in 0.9% saline as a high viscosity liquid) or 75% (w/v) albumin as a paste. The transducer species was nickel flake with an average particle size of about 46 micron, mixed into the albumin solution at 5-10% (w/v). The mixture of albumin, saline and nickel had a highly viscous rheological nature. The fusion composition preparation showed visual evidence through coagulation and change in opacity and was warm to the touch after 20-30 seconds when placed between the two solenoid coils with the radiofrequency power supply producing about 210 W.

Example 4

Tissue Fusion

Ex vivo sheep arteries were dissected transversely across the lumen to form sections or were cut longitudinally to form sheets of tissue. The fusion composition described in Example 3 was sandwiched between small sections, i.e., about 1 cm$^2$, of the tissue sheets and was placed between the coils as before. Tissue fusion was apparent by observation. The tissues fused together seamlessly and it became difficult to tease apart the two sections with forceps. No effort was made to control temperature, however, overheating was apparent from a color change in the tissue with longer exposure times of >45 seconds.

A fusion composition comprising 5% Ni and 50% albumin was placed on the adventitia of one end of a transverse-cut sheep artery (FIG. 32A) and the end of another sheep artery dissected across the lumen was placed over the adventitia of artery and the 200 micron layer of the adhesive fusion composition. A glass rod was used as a support to hold the artery ends in place. The sample was then positioned between the faces of the opposing coils (not shown) and the sample was exposed for about 30 seconds. The magnetic intensity between the two coils is theoretically estimated to be about 0.3 kA/m. Fusion, or anastomosis, was visually apparent after about ninety seconds and the fused tissue could not be teased apart with forceps without dissection. Tests were repeated five times with equivalent results.

The vessels were placed in 10% formalin, sectioned transversely across the fused area and submitted for histological preparation and staining with hematoxylin-eosin. FIG. 32B shows presence of metallic transducer particles 1096, 1098 at the interface between the two overlapping sections of arteries and delineates the margin of tissue fusion.

Example 5

Effects of Inductive Heating on Fusion Compositions

A commercially available induction power-supply (Lepel Corp., Edgewood, N.Y.) modified through the addition of internal capacitors to accept a solenoid coil was used. The device produced an average power of about 100 W at a frequency of 400 kHz and a field intensity of 0.3 A/m. The output of the device was coupled into a helical wound coil with an outside diameter of 11 cm made of 11 turns of ⅛ inch copper tubing.

The fusion compositions tested contained 50% albumin with a tranducer consisting of 10% 150 mesh stainless steel or 20% 150 mesh stainless steel or 20% 325 mesh nickel. Each fusion composition was separately positioned within the bore of the coil flush with the surface and the temperature of the upper surface of the fusion composition was measured with an infrared thermometer (FIG. 33). As expected, nickel heats more efficiently than stainless steel due to its greater magnetic permeability, reaching a threshold temperature of ~70° C. within 30 seconds, while stainless steel transducers require double the time.

Example 6

Solenoid Coil Design and Fusion Compositions

A commercially available induction radiofrequency generator (Daihen Corporation, Model RGA-10A) was coupled to a two-turn solenoid type applicator (FIG. 32) constructed of ⅛ in. outside diameter (o.d.) silver-plated copper tubing; the resulting coil having an outside diameter of 23 mm, thickness of 7.5 mm. The coil was wrapped in teflon pipe-tape. Nylon hose (o.d. 0.25 in.) was attached to each end of the coil and tap water was circulated through in order to cool the coil and capacitors. The central conductor of a coaxial cable (Thermax Type RG303) was connected to the capacitor bank, and the shield was connected to one end of the copper tube coil. Eight high-voltage radio-frequency capacitors (American Technical Ceramics, Huntington Station, N.Y.; Series 100C) with capacitances of 2700, 1000, 680, and 47 pf, were positioned between each end of the coil in parallel to effect impedance matching with the 50 W output of the rf generator. The coil applicator was fixed in place in a laboratory stand with the plane of the coil parallel with the floor of the laboratory. The output of the radiofrequency generator was monitored by a calibrationed directional-coupler, which was linked to a Hewlett-Packard power-sensor and Hewlett-Packard 438A power-meter. Different fusion compositioned were applied to waxed paper and positioned on the coil.

Radiofrequency power was applied to the coil at (1) 250 W continuous-wave (CW) power, (2) 50 W average power with a duty cycle of 60% and a pulse repetition rate of 1 Hz. The fusion compositions consisted of one of (a) 50% ovalbumin (OA) in water with 20% 325 mesh nickel (Ni) flake (b) 50% ovalbumin with 20% stainless steel (SS) powder (c) 50% ovalbumin with approximately 1% stainless steel powder (d) 50% ovalbumin with 20% CaCl (e) 50% ovalbumin with 20% MgCl or (f) 50% ovalbumin alone. Changes in the rheologic nature of the fusion composition, upon the application of RF energy to the applicator coil, was evident by a change in the visual appearance of the composition (usually a reduction in specular reflection and/or color change) when held at a distance of approximately 2 mm from the edge of the coil. After the RF energy was terminated, the rheologic nature of the composition was tested by pressing the experimenter's fingertip on the surface of the composition. The results are shown in Table 1 below.

TABLE 1

|  | RF energy applied to coil: | |
| --- | --- | --- |
|  | 250 W CV | 50 W pulsed |
| Fusion Composition | Approximate time (seconds) | |
| 50% OA/20% SS | 2 | 1 |
| 50% OA/1% SS | 15 | 10 |
| 50% OA/20% CaCl | 45 | 35 |
| 50% OA | >60 | >60 |

Example 7

Pancake Coil Design and Fusion Compositions

A commercially available induction radiofrequency generator (Daihen Corporation, Model RGA-10A) was coupled to a two-turn pancake type applicator (FIG. 32) constructed of ⅛ in. outside diameter (o.d.) silver-plated copper tubing; the resulting coil having an outside diameter of 23 mm, thickness of 7.51 mm. The coil was wrapped in teflon pipe-tape. Nylon hose (o.d. 0.25 in.) was attached to each end of the coil and tap water was circulated through in order to cool the coil and capacitors. The central conductor of a coaxial cable (Thermax Type RG303) was connected to the capacitor bank, and the shield was connected to one end of the copper tube coil. Eight high-voltage radio-frequency capacitors (American Technical Ceramics, Huntington Station, N.Y.; Series 100C) with capacitances of 2700, 1000, 680, and 47 pf, were positioned between each end of the coil in parallel to effect impedance matching with the 50 W output of the rf generator. The coil applicator was fixed in place in a laboratory stand with the plane of the coil parallel with the floor of the laboratory. The output of the radiofrequency generator was monitored by a calibrationed directional-coupler, which was linked to a Hewlett-Packard power-sensor and Hewlett-Packard 438A power-meter. Different fusion compositioned were applied to waxed paper and positioned on the coil.

Radiofrequency power was applied to the coil at (1) 250 W continuous-wave (CW) power, (2) 50 W average power with a duty cycle of 20% and a pulse repetition rate of 1 Hz. The fusion compositions consisted of one of (a) 50% ovalbumin (OA) in water with 20% 325 mesh nickel (Ni) flake (b) 50% ovalbumin with 20% stainless steel (SS) powder (c) 50% ovalbumin with approximately 1% stainless steel powder (d) 50% ovalbumin with 20% CaCl (e) 50% ovalbumin with 20% MgCl or (f) 50% ovalbumin alone. Changes in the rheologic nature of the fusion composition, upon the application of rf energy to the applicator coil, was evident by a change in the visual appearance of the composition (usually a reduction in specular reflection and/or color change) when materials were held at a distance of approximately 2 mm from the surface of the coil. After the rf energy was terminated, the rheologic nature of the composition was tested by pressing the experimenter's fingertip on the surface of the composition. The results are shown in Table 2 below.

TABLE 2

| Fusion Composition | RF energy applied to coil: | |
|---|---|---|
| | 250 W CV | 50 W pulsed |
| | Approximate time (seconds) | |
| 50% OA/20% SS | 1 | 1 |
| 50% OA/1% SS | 20 | 15 |
| 50% OA/20% CaCl | 40 | 30 |
| 50% OA | >60 | >60 |

Example 11

Frequency and Power Effects on Curing of Fusion Composition

In series of pilot experiments, samples of the adhesive composition were cured at various frequencies, powers and times (see table below). Two samples of adhesive composition were prepared with either 20% nickel flake (120 mesh size) or 20% 316L stainless steel particles (80 mesh). Even thought nickel has been known to cause allergic responses in some individuals, it was tested in these experiments because it is a well-characterized ferromagnetic material. Samples were applied to a glass slide and placed approximately 2 mm from the surface of a 2 turn copper coil (1 cm diameter). The curing point was determined by a change from glossy to dull appearance, and confirmed by mechanically probing the material to assert that it had become solid. The results are shown in Table 3.

TABLE 3

| Sample | Frequency | Power | Approx. time to cure (sec) |
|---|---|---|---|
| 20% Ni/ | 256 KHz | 1000 W | 5-10 |
| 80% ovalbumin | 653 KHz | 1000 W | 1 |
| | 13.6 MHz | 1000 W | <<1 |
| 20% stainless steel/ | 400 KHz | 1000 W | 4-8 |
| 80% ovalbumin | 653 KHz | 1000 W | 2-4 |

The following references are cited herein:
1. Bass, et al, Laser Surg. Med. 17, 315-349 (1995).
2. Freid, et al, Lasers Surg. Med. 27, 55-65 (2000).
3. Davies E J. Conduction and Induction Heating. Inst. Elect. Engs. and P. Peregrinus:London (1990).
4. Orfeuil M. Electric Process Heating: Technologies/Equipment/Applications. Battelle Press: Columbus Ohio (1987).
5. Zinn S. and Semiatin S L. Elements of Induction Heating—Design, Control and Applications, Electric Power Research Institute: Palo Alto, Calif. (1988).
6. Stauffer et al, IEEE Trans. Biomed. Eng. BME-31, 235-251 (1984).
7. Jordan A. et al, Effects of magnetic fluid hyperthermia (MFH) on C3H mammary carcinoma in vivo. Int. J. Hyperthermia. 13(6):587-605 (1997).
8. Hamad-Schifferli K et al, Nature 415, 152-155 (2002).
9. Moran et al, Clinical Orthopaedics & Related Research. 381:248-55, (2000).
10. Damodaran S. Int. J. Biologic. Macromolec. 11, pp. 2-8 (1989).

Any patents or publications mentioned in this specification are indicative of the levels of those skilled in the art to which the invention pertains. These patents and publications are herein incorporated by reference to the same extent as if each individual publication was specifically and individually incorporated by reference.

One skilled in the art will readily appreciate that the present invention is well adapted to carry out the objects and obtain the ends and advantages mentioned, as well as those inherent therein. It will be apparent to those skilled in the art that various modifications and variations can be made in practicing the present invention without departing from the spirit or scope of the invention. Changes therein and other uses will occur to those skilled in the art which are encompassed within the spirit of the invention as defined by the scope of the claims.

What is claimed is:
1. A method of treatment for one or more substrates in an individual, comprising:
   securing said substrate(s) proximal to a susceptor, wherein said substrate is intact and said susceptor is a dissociable ion, or a mixture of dissociable ions;
   applying radiofrequency energy that generates a magnetic field to said substrate(s) or to said susceptor or to a combination thereof to inductively generate heat therein;
   affixing said substrate(s) via said heat thereby effecting treatment; and
   controlling the affixing of said substrate(s) via feedback monitoring of a property of said susceptor, said energy or a combination thereof.
2. The method of claim 1, wherein said substrate(s) is a tissue, an implant or a bandage.
3. The method of claim 1, wherein said substrate is secured by a surgical fastener, a laminate or a surgical fitting further comprised of a fusion composition.
4. The method of claim 3, wherein said surgical fastener is a staple, a clip or a suture.
5. The method of claim 1, wherein said substrate is secured by an adherend.
6. The method of claim 5, wherein said adherend is a protein or a polymer.
7. The method of claim 1, wherein said energy is applied in pulses.
8. The method of claim 1, wherein said radiofrequency energy has a frequency of about 20 kHz to about 40 GHz.
9. The method of claim 1, wherein said magnetic field is generated via a substantially flat antenna.
10. The method of claim 9, wherein said antenna comprises at least one coil of electrical conductor.
11. The method of claim 10, wherein said electrical conductor is a solid wire or hollow tubing.
12. The method of claim 9, wherein said antenna is a single coil antenna, or a double coil antenna.
13. The method of claim 1, wherein affixing said substrate(s) forms a scaffold or a lattice structure within said substrate or between substrates.
14. The method of claim 1, wherein affixing said substrate(s) seals a tissue, fills a tissue defect, or bonds tissues together.
15. The method of claim 1, wherein said property is heat, an electrical property, eddy currents, conductivity, or frequency changes or a combination thereof.
16. The method of claim 15, wherein heat is monitored via optical detection.
17. The method of claim 16, wherein said optical detection is infrared.

* * * * *